(12) United States Patent
Klagsbrun et al.

(10) Patent No.: US 6,635,421 B1
(45) Date of Patent: Oct. 21, 2003

(54) NEUROPILINS AND USE THEREOF IN METHODS FOR DIAGNOSIS AND PROGNOSIS OF CANCER

(75) Inventors: Michael Klagsbrun, Newton, MA (US); Shay Soker, Brookline, MA (US); Hua-Quan Miao, Brookline, MA (US); Seiji Takashima, Osaka (JP)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/583,638

(22) Filed: May 30, 2000

Related U.S. Application Data

(63) Continuation of application No. PCT/US98/26127, filed on Dec. 9, 1998.
(60) Provisional application No. 60/069,155, filed on Dec. 9, 1997, and provisional application No. 60/069,689, filed on Dec. 12, 1997.

(51) Int. Cl.$^7$ ................................................. C12Q 1/68

(52) U.S. Cl. ........................... 435/6; 435/7.1; 435/7.23; 436/501

(58) Field of Search ........................... 435/320.1, 326.1, 435/7.1, 7.23, 6; 530/351, 402, 387.1, 387.7; 536/23.5; 436/501

(56) References Cited

U.S. PATENT DOCUMENTS 5,639,856 A * 6/1997 Goodman et al. .......... 530/326
6,054,293 A * 4/2000 Tessier-Lavigne et al. . 435/69.1

FOREIGN PATENT DOCUMENTS

| WO | WO 94/11499 A | 5/1994 |
| WO | WO 97/08313 | 3/1997 |
| WO | WO 9930157 A2 * | 6/1999 |

OTHER PUBLICATIONS

Gagnon, ML, et al, Identification of a natural soluble neuropilin–1 that binds vascular endothelial growth factor: in vivo expression and antitumor activity, Proceedings of the National Academy of Sciences USA, vol. 97, No. 6, pp. 2573–2578.*
Uneda, S, et al, 2001, Expression of VEGF121 adn VEGF165 and their receptors (KDR, flt–1, neuropilin) in purified myeloma cells, Blood, vol. 98, No. 11, Pt. 1, pp. 637A–638A.*
Fujisawa, H, et al, 1995, Growth–associated expression of a membrane protein, neuropilin, in Xenopus optic nerve fibers, Developmental Neuroscience, vol. 17, No. 5–6, pp. 343–349.*
He, Z, et al, 1997, Neuropilin is a receptor for axonal chemorepellent semaphorin III, Cell, vol. 90, No. 4, pp. 739–751.*
Tockman, MS, et al, 1992, Considerations in bringing a cancer biomarker to clinical application, Cancer Research, vol. 52, Suppl., pp. 2711s–2718s.*
Kolodkin, AL, et al, Aug. 22, 1997, Neuropilin is a semaphorin III receptor, Cell, vol. 90, pp. 753–762.*
Giraudo, E, et al, 1998, Tumor necrosis factor–alpha regulates expression of vascular endothelial growth factor receptor–2 expression and its co–receptor neuropilin–1 [. . . ], Journal of Biological Chemistry, vol. 273, No. 34, pp. 22128–22135.*
Gura, T, 1997, Systems for identifying drugs are often faulty, Science, vol. 278, pp. 1041–1042.*
Miao, H–Q, et al, 2000, Neuropilin–1 expression by tumor cells promotes tumor angiogenesis and progression, FASEB Journal, vol. 14, pp. 2532–2539.*
Soker, S, et al, 1997, Inhibition of vascular endothelial growth factor (VEGF)–induced endothelial cell proliferation by a peptide corresponding to the exon 7–encoded domain of VEGF165, Journal of Biological Chemistry, vol. 272, No. 50, pp. 31582–31588.*
Fakhari, M, et al, 2002, Selective upregulation of vascular endothelial growth factor receptors neuropilin–1 and –2 in human neuroblastoma, Cancer, vol. 94, pp. 258–263.*
Xin, H, et al, 2000, Identification of a novel aspartic–like protease differentially expressed in human breast cancer cell lines, Biochemica et Biophysica Acta, vol. 1501, pp. 125–137.*
Wizigmann–Voos, S, et al, 1995, Up–regulation of vascular endothelial growth factor and its receptors in von Hippel––Lindau disease–associated and sporadic hemangioblastomas, Cancer Research, vol. 55, No. 6, pp. 1358–1364.*
Jackson, MW, et al, 1997, Vascular endothelial growth factor (VEGF) expression in prostate cancer and benign prostatic hyperplasia, Journal of Urology, vol. 157, No. 6, pp. 2323–2328.*
Ferrer, FA, et al, 1997, Vascular endothelial growth factor (VEGF) expression in human prostate cancer: in situ and in vitro expression of VEGF by human prostate cancer cells, Journal of Urology, vol. 157, No. 6, pp. 2329–2333.*
Latil, A, et al, 2000, VEGF overexpression in clinically localized prostate tumors and neuropilin–1 overexpression in metastatic forms, International Journal of Cancer, vol. 86, No. 3, pp. 167–171.*

(List continued on next page.)

*Primary Examiner*—Anthony C. Caputa
*Assistant Examiner*—Stephen Rawlings
(74) *Attorney, Agent, or Firm*—Nixon Peabody LLP

(57) ABSTRACT

The present invention relates to VEGF receptors (VEGFR) and neuropilins such as VEGF$_{165}$R/NP-1 and NP-2 that are associated with metastatic potential of a malignant cell and their use in the diagnosis and prognosis of cancer. Preferred ones are VEGF$_{165}$R/NP-1 and NP-2 but any neuropilin or VEGFR, where the constituents share at least about 85% homology with either of the above VEGF$_{165}$R/NP-1 and NP-2 can be used. More preferably, such constituent shares at least 90% homology. Still more preferably, each constituent shares at least 95% homology.

4 Claims, 28 Drawing Sheets

OTHER PUBLICATIONS

Lee, C, et al, 1993, In vivo and in vitro approaches to study metastasis in human prostatic cancer, Cancer Metastasis Reviews, vol. 12, No. 1, pp. 21–28.*

Phillips, RM, et al, 1990, A critical appraisal of the predictive value of in vitro chemosensitivity assays, Journal of the National Institutes of Health, vol. 82, No. 18, pp. 1457–1468.*

Roush, W, 1998, Receptor links blood vessels, axons, Science, vol. 279, No. 5359, pp. 2042.*

Pan, Q, et al, 2000, Neuropilins, ectopically expressed in relapsed childhood acute lymphobblastic leukemia, enhance lymphoid survival and promote tumorigenesis, Blood, vol. 96, No. 11, Pt. 1, pp. 500A (meeting abstract).*

Bange, J, et al, 2002, Cancer progression and tumor cell motility are associated with the FGFR4 Arg(388) allele, Cancer Research, vol. 62, No. 3, pp. 840–847.*

Feiner, L, et al, 1997, Secreted chick semphorins bind recombinant neuropilin with similar affinities but bind different subsets of neurons in situ, Neuron, vol. 19, No. 3, pp. 539–545.*

Barleon, B, et al, 1996, Migration of human monocytes in response to vascular endothelial growth factor (VEGF) is mediated via the VEGF receptor flt-1, Blood, vol. 87, No. 8, pp. 3336–3343.*

Ward, AM, 1985, Tumour Markers, Developmental Oncology, vol. 21, pp. 90–106.*

Soker et al (JBC, Mar. 1996, vol. 271:561–7).*

Bowie et al, Science, 247:1306–1310, 1990, p. 1306, col.2).*

Burgess et al. J. of Cell Bio. 111:2129–2138, 1990.*

Lazar et al. Molecular and Cellular Biology 8:1247–1252 (1988).*

T. Omura et al., "Identification of a 190 kDa Vascular Endothelial Growth Factor 165 Cell Surface Binding Protein on a Human Glioma Cell Line," *J. Biol. Chem.*, 272(37)23317–23322, 1997.

S. Soker et al., "Neuropilin–1 is expressed by endothelial and Tumor Cells as an Isoform–Specific Receptor for Vascular Endothelial Growth Factor," *Cell*, 92:735–745, 1998.

S. Soker et al., "Characterization of Novel Vascular Endothelial Growth factor (VEGF) Receptors on Tumor Cells that Bind VEGF165 Via it Exon 7–Encoded Domain," *J. Biol. Chem.*, 271(10) 5761–5767, 1996.

H. Chen et al., "Neuropilin–2, A Novel Member of the Neuropilin Family, is a High Affinity receptor for the Semaphorins sema E and sema IV but not sema III," *Neuron*, 19:547–559, 1997.

A.L. Kolodkin et al., "Neuropilin is a Semaphorin III Receptor," *Cell*, 90:753–762, 1997.

* cited by examiner

1    MERGLPLLCAVLALVLAPAGAFRNDKCGDTIKIESPGYLTSPGYPHSYHPSEKCEWLIQAPDPYQRIMIN    70
71   FNPHFDLEDRDCKYDYVEVFDGENENGHFRGKFCGKIAPPPVVSSGPFLFIKFVSDYETHGAGFSIRYEI   140
141  FKRGPECSQNYTTPSGVIKSPGFPPEKYPNSLECTYIVFAPKMSEIILEFESFDLEPDSNPPGGMFCRYDR  210
211  LEIWDGFPDVGPHIGRYCGQKTPGRIRSSSGILSMVFYTDSAIAKEGFSANYSVLQSSVSEDFKCMEALG   280
281  MESGEIHSDQITASSQYSTNWSAERSRLNYPENGWTPGEDSYREWIQVDLGLLRFVTAVGTQGAISKETK   350
351  KKYYVKTYKIDVSSNGEDWITIKEGNKPVLFQGNTNPTDVVVAVFPKPLITRFVRIKPATWETGISMRFE   420
421  VYGCKITDYPCSGMLGMVSGLISDSQITSSNQGDRNWMPENIRLVTSRSGWALPPAPHSYINEWLQIDLG   490
491  EEKIVRGIIIQGGKHRENKVFMRKFKIGYSNNGSDWKMIMDDSKRKAKSFEGNNYDTPELRTFPALSTR   560
561  FIRIYPERATHGGLGLRMELLGCEVEAPTAGPTTPNGNLVDECDDDQANCHSGTGDDFQLTGGTTVLATE  630
631  KPTVIDSTIQSEFPTYGFNCEFGWGSHKTFCHWEHDNHVQLKWSVLTSKTGPIQDHTGDGNFIYSQADEN  700
701  QKGKVARLVSPVVYSQNSAHCMTFWYHMSGSHVGTLRVKLRYQKPEEYDQLVWMAIGHQGDHWKEGRVLL  770
771  HKSLKLYQVIFEGEIGKGNLGGIAVDDISINNHISQEDCAKPADLDKKNPEIKIDETGSTPGYEGEGEGD  840
841  KNISRKPGNVLKTLDPILITIIAMSALGVLLGAVCGVVLYCACWHNGMSERNLSALENYNFELVDGVKLK  910
911  KDKLNTQSTYSEA 923

FIG. 3

COMPARATIVE DEDUCED AMINO ACID SEQUENCES
OF HUMAN VEGF$_{165}$R/NP AND VEGF$_{165}$R/NP-1

```
VEGF165R/NP-2    1 MDMF-PLTW-VFLALYFSRHQVRGQPOPPCGG-RLNSK--DA------GY       50
VEGF165R/NP-1      MERGLPLLCAV-LAL------VLA-PA---GAFR-NDKCGDTIKIESPGY

NP-2   51 ITSPGYPQDY-PSHQNCEW-IVYAPEPNQKIVLNFNPEFEIEKHDCKYDF      100
         NP-1      LTSPGYPHSYHPSEK-CEWLIQ-APDPYQRIMINFNPHFDLEDRDCXYDY

NP-2  101 IEIRDGDSESADLLGKHCGNIAPPTIISSGSMLYIKFTSDYARQGAGFSL     150
         NP-1      VEVFDGENENGHFRGKFCGKIAPPPVVSSGPFLFIKFVSDYETHGAGFSI

NP-2  151 RYEIFKTGSEDCSKNFTSPNGTIESPGFPEKYPHN-LDCTFTIL-AKPKM     200
         NP-1      RYEIFKRGPE-CSQNYTTPSGVIKSPGFPEKYP-NSLECTY-IVFA-PKM

NP-2  201 -EIILQFLIFDLEHD--PLQVGEGD-CKYDWLDIWDGIPHVGPLIGKYCG     250
         NP-1      SEIILEFESFDLEPDSNPP---G-GMFCRYDRLEIWDGFPDVGPHIGRYCG

NP-2  251 TKTPSELRSSTGILSLTFHTDMAVAKDGFSARYYLVHQEPL-ENFQCNVP     300
         NP-1      QKTPGRIRSSSGILSMVPYTDSAIAKEGFSANYS--VLQSSVSEDFKCMEA

NP-2  301 LGMESGAIANEQISASSTYSDGRWTPQQSRLHGDDNGWTPNLDSNKEYLQ     350
         NP-1      LGMESGEIHSDQITASSQYSTN-WSAERSRLNYPENGWTPGEDSYREWIQ

NP-2  351 VDL---RFLTMLTAIATQGAISRETQNGYYVKSYKLEVSTNGEDWMVYRH     400
         NP-1      VDLGLURFVT---AVGTQGAISKETKKKYYVKTYKIDVSSNGEDWITIKE

NP-2  401 GKNHK-V-FQAN-NDATEVVLN---KLHAPLLTRFVRIRPQTWHSGIALR     450
         NP-1      G-N-KPVLFQGNTNP-TDVVVAVFPK---PLITRFVRIKPATWETGISMR

NP-2  451 LELFGCRVTDAPCSMKLGMLSGLIADSQISASSTQEYL-WSPSAARLVSS     500
         NP-1      FEVYGCKITDYPCSGMLGMVSGLISDSQIT-SSNQGDRNWMPENIRLVTS
```

FIG. 4A

| FIG. 4A |
|---------|
| FIG. 4B |

FIG. 4

```
NP-2 501  RSGWF-PRIPQAQPGE---EWLQVDLGTPKTVKGVIIQGARGGDSITAVE 550
NP-1      RSGWALP--P-A-PHSYINEWLQIDLGEEKIVRGIIIQG--GKHRENKV-

NP-2 551  ARAFVRKFKVSYSLNGKDWEYIQDP--RTQQPKLFEGNMHYDTPDIRRFD 600
NP-1      ---FMRKFKIGYSNNGSDWKMIMDDSKRKA--KSFEGNNNYDTPELRTF-

NP-2 601  PIPAQYVRV---YPERWSPA--GI-GMRLEVLGCDWTDSKPTVE--TLGP 650
NP-1      P--ALSTRFIRIYPER---AFHGGLGLRMELLGCE-------VEAPTAGP

NP-2 651  TVKSEETTTPYPTEEEATECGE---NC-SFE-DDKDLQ-----L----P- 700
NP-1      T-----T--PNGNLVD--ECDDDQANCHSGTGDDFQLTGGTTVLATEKPT

NP-2 701  ---S---------GFNCNFD------FLEEPCGWMYD-BA--KW--LRTT 750
NP-1      VIDSTIQSEFPTYGFNCEFGWGSHKTF----CHWEHDNHVQLKNSVL-T-

NP-2 751  WASSSSPN-DRTFPDDRNFLRLQSDS-QREGQYARLISPPVHLPRSPVCM 800
NP-1      --SKTGPIQDHTG-DG-NFIYSQADENQK-GKVARLVSPVVYSQNSAHCM

NP-2 801  EFQYQATG---G--RGVAL--QVVREASQESKLLWV-IREDQGGEWKHGR 850
NP-1      TFWYHMSGSHVGTLR-VKLRYQKPEEYDQ---LVWMAIGH-QGDHWKEGR

NP-2 851  IILP-SYDMEYQ-IVFEGVIGKGRSGEIAIDOIRI----STDVPLENCME 900
NP-1      VLLHKSLKL-YQVI-FEGEIGKGNLGGIAVDDISINNHISQ----EDCAK

NP-2 901  PISAFAGENFKVDIPEIHERE-G----YEDEIDDEYEVDWSNSSSATSGS 950
NP-1      P--ADLDK--KN--PEIKIDETGSTPGYEGEG--EG--DK-NISRKP-GN

NP-2 951  GAPSTDKEKSWLYTLDPILITIIAMSSLGVLLGATCAGLLLYCTCSYSGL 1000
NP-1      VL----K------TLDPILITIIAMSALGVLLGAVC-GVVLYCACWHNGM

NP-2 1001  SSR--SCTTLENYNFELYDG--LKHKVKMNHQKCCSEA 1038
NP-1       SERNLSA--LENYNFELVDGVKLK-KDKLNTQSTYSEA
```

HUMN NEUROPILIN-2 AMINO ACID SEQUENCE:

MDMFPLTWVFLALYFSRHQVRGQPDPPCGGRLNSKDAGYITSPGYPQDYPSHQN
CEWIVYAPEPNQKIVLNFNPHFEIEKHDCKYDFIEIRDGDSESADLLGKHCGNIAPP
TIISSGSMLYIKFTSDYARQGAGFSLRYEIFKTGSEDCSKNFTSPNGTIESPGFPEK
YPHNLDCTFTILAKPKMEIILQFLIFDLEHDPLQVGEGDCKYDWLDIWDGIPHVGPL
IGKYCGTKTPSELRSSTGILSLTFHTDMAVAKDGFSARYYLVHQEPLENFQCNVP
LGMESGRIANEQISASSTYSDGRWTPQQSRLHGDDNGWTPNLDSNKEYLQVDLR
FLTMLTAIATQGAISRETQNGYYVKSYKLEVSTNGEDWMVYRHGKNHKVFQANN
DATEVVLNKLHAPLLTRFVRIRPQTWHSGIALRLELFGCRVTDAPCSNMLGMLS
GLIADSQISASSTQEYLWSPSAARLVSSRSGWFPRIPQAQPGEEWLQVDLGTPK
TVKGVIIGGARGGDSITAVEARAFVRKFKVSYSLNGKDWEYIQDPRTQQPKLFEG
NMHYDTPDIRRFDPIPAQYVRVYPERWSPAGIGMRLEVLGCDWTDSKPTVETLG
PTVKSEETTTPYPTEEEATECGENCSFEDDKDLQLPSGFNCNFDFLEEPCGWMYD
HAKWLRTTWASSSSPNDRTFPDDRNFLRLQSDSQREGQYARLISPPVHLPRSPV
CMEFQYQATGGRGVALQVVREASQESKLLWVIREDQGGEWKHGRIILPSYDMEYQ
IVFEGVIGKGRSGEIAIDDIRISTDVPLENCMEPISAFAGENFKVDIPEIHEREGYED
EIDDEYEVDWSNSSSATSGSGAPSTDKEKSWLYTLDPILITIIAMSSLGVLLGAT
GAGLLLYCTCSYSGLSSRSCTTLENYNFELYDGLKHKVKMNHQKCCSEA*

FIG. 12

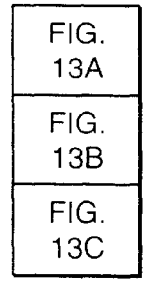

FIG. 13

```
gaattcggca cgaggggaaa ataaaagaga gaaaaacaca aagatttaaa caagaaacct    60
acgaacccag ctctggaaag agccacctc ttcaagacac tccaaaatgg atatgtttcc tctcacctgg   120
gttctcttag ccctctactt ttcaagacac caagtgagag gccaaccaga cccaccgtgc   180
ggagtcgtt tgaattccaa agatgctggc tatatcacct ctccgttta ccccaggac   240
tacccctccc accagaactg cgagtggatt gtttacgccc ccgaaccaa ccagaagatt   300
gtcctcaact tcaaccctca ctttgaaatc gagaagcacg actgcaagta tgacttatc   360
gagattcggg atggggacag tgaatccgca gacctcctgg gcaaacactg tgggaacatc   420
gccccgccca ccatcatctc ctcgggctcc atgctctaca tcagttcac ctccgactac   480
gccggcagg gggcaggctt ctctctgcgc tacgagatct tcaagacagg ctctgaagat   540
tgctcaaaaa acttcacaag ccccaacggg accatcgaat ctcctggtt tcctgagaag   600
tatccacaca acttggactg caccttttacc atcctgcca aacccaagat ggagatcatc   660
ctgcagttcc tgatctttga cctggagcat gacccctttgc agtgggaga ggggactgc   720
aagtacgatt ggctggacat ctgggatggc attccacatg ttgccccct gattggcaag   780
tactgtggga ccaaaacacc ctctgaactt cgttcatcga cgggatcct ctccctgacc   840
tttcacacgg acatggcggt ggccaaggat ggcttctctg cgcgttacta cctggtccac   900
caagagccac tagagaactt tcagtgcaat gttcctctgg gcatggagtc tggccggatt   960
gctaatgaac agatcagtgc ctcatctacc tactctgatg ggaggtggac ccctcaacaa  1020
agccggctcc atggtgatga caatgctgtt accccaact tggattccaa caaggagtat  1080
ctccaggtgg acctgcgctt tttaaccatg ctcacggcca tgcaacaca gggagcgatt  1140
tccagggaaa cacagaatgg ctactacgtc aaatcctaca agctgaagt cagcactaat  1200
```

FIG. 13A

```
ggagaggact ggatggtgta ccggcatggc aaaaaccaca aggtatttca agccaacaac  1260
gatgcaactg aggtggttct gaacaagctc ctcagccac  tgctgacaag gtttgttaga  1320
atccgccctc agacctggca ctcaggtatc gccctccggc tggagctctt cggctgccgg  1380
gtcacagatg ctccctgctc caacatgctg gggatgctct caggcctcat tgcagactcc  1440
cagatctccg cctcttccac ccaggaatac ctctggagcc ccagtgcagc ccgcctggtc  1500
agcagccgct cgggctggtt ccctcgaatc cctcaggccc agcccggtga ggagtggctt  1560
caggtagatc tgggaacacc caagacagtg aaaggtgtca tcatccaggg agcccgcgga  1620
ggagacagta tcactgctgt ggaagccaga gcatttgtgc gcaagttcaa agtctcctac  1680
agcctaaacg gcaaggactg ggaatacatt caggacccca ggaccagca gccaaagctg  1740
ttcgaaggga acatgcacta tgacacccct gacatccgaa ggtttgaccc cattccggca  1800
cagtatgtgc gggtataccc ggagaggtgg tcgccggcgg ggattgggat gcggctggag  1860
gtgctgggct gtgactggac agactggaac cccacggtag agacgctggg accactgtg   1920
aagagcgaag agacaaccac cccctacccc accgaagagg aggccacaga gtgtggggag  1980
aactgcagct ttgaggatga caaagatttg cagctccctt cgggattcaa ttgcaacttc  2040
gatttcctcg aggagccctg tggtttggat tatgaccatg ccaagtggct ccggaccacc  2100
tgggccagca gctccagccc aaacgaccgg acgtttccag atgacaggaa tttcttgcgg  2160
ctgcagagtg acagccagag agagggccag tatgcccggc tcatcagccc ccctgtccac  2220
ctgcccgaa gcccggtgtg catggagttc cagtaccagg ccacggggcgg ccgcggggtg  2280
gcgctgcagg tggtgcggga gcagccagag gagagcaagt tgctgtgggt catccgtgag  2340
gaccaggggcg gcgagtggaa gcacggggcgg atcatcctgc ccagctacga catggagtac  2400
```

FIG. 13B

```
cagattgtgt tcgagggagt gataggggaaa ggacgttccg gagagattgc cattgatgac    2460
attcgataa  gcactgatgt cccactggag aactgcatgg aacccatctc ggcttttgca    2520
ggtgagaatt ttaaagtgga catcccagaa atacatgaga gagaaggata tgaagatgaa    2580
attgatgatg aatacgaggt ggactggagc aattctttctt ctgcaacctc agggtctggc   2640
gccccctcga ccgacaaaga aaagagctgg ctgtacaccc tggatcccat cctcatcacc    2700
atcatcgcca tgagctcact gggcgtcctc ctggggcca cctgtgcagg cctcctgctc     2760
tactgcacct gttcctactc gggcctgagc tcccgaagct gcaccacact ggagaactac    2820
aacttcgagc tctacgatgg ccttaagcac aaggtcaaga tgaaccacca aaagtgctgc    2880
tccgaggcat gacggattgc acctgaatcc tatctgacgt ttcattccag caagaggggc    2940
tggggaagat tacattttt  tttcctttgg aaactgaatg ccataatctc gatcaaaccg    3000
atccagaata ccgaaggtat ggacaggaca gaaaagcgag tgcaggagg  aagggagatg    3060
cagccgcaca gggatgatt  acccctcctag gaccgcggtg gctaagtcat tgcaggaacg    3120
gggctgtgtt ctctgctggg acaaaacagg agctcatctc tttggggtca cagttctatt   3180
ttgtttgtga gtttgtatta ttattattat tattattatt atatttattt tcttttggtct  3240
gtgagcaact caaagaggca gaagaggaga atgacttttc cagaatagaa gtggagcagt   3300
gatcattatt ctccgctttc tcttttctaat caaacacttga aaagcaaaagt gtctttcag  3360
ccttctccatc tttacaaata.aaactcaaaa aagctgtcca gctt                   3404
```

FIG. 13C

| FIG. 14A | FIG. 14B | FIG. 14C | FIG. 14E | FIG. 14F |
|---|---|---|---|---|

```
ATG  GAG  247  GGG  CTG  256  CTC  CTC  265  GCC  GTG  274  GCC  CTC  283  CTC  GCC  292
 M    E   AGG   G    L   CCG   L    L   TGC   A    V   CTC   A    L   GTC   L    A   CCG
           R              P         C         L              V              P

GCC  GGC  301  TTT  CGC  310  GAT  AAA  319  GGC  ATA  328  GAT  AAA  337  GAA  AGC  346
 A    G   GCT   F    R   AAC   D    K   TGT   G    I   ACT   D    K   ATT   E    S   CCC
           A       →a1    N         C         T              I              P

GGG  TAC  355  ACA  TCT  364  TAT  CCT  373  CAT  ATA  382  TCT  AAA  391  GAA  AGC  400
 G    Y   CTT   T    S   CCT   Y    P   CCT   H    I   TAT   S    K   AGT   E    S   TGC
           L              P         P         Y              S              C

GAA  TGG  409  ATT  CAG  418  CCG  GAC  427  TAC  CAG  436  ATT  AAA  445  GAA  AAA  454
 E    W   CTG   I    Q   GCT   P    D   CCA   Y    Q   AGA   I    K   ATC   E    K   AAC
           L              A         P         R              I              N

CCT  CAC  463  GAT  TTG  472  GAC  CCG  481  CAT  ATG  490  AAG  ATG  499  GAA  AAA  508
 P    H   TTC   D    L   GAG   D    P   GAC   H    M   TAT   K    M   GTG   E    K   TTC
           F              E         D         Y              V              F

GAT  GAA  517  AAT  GGA  526  TCA  CAT  535  TTT  GGG  544  GAC  TAC  553  TGT  GTC  562
 D    E   GAA   N    G   AAT   S    H   TTT   F    G   AAG   D    Y   TGT   C    V   GCC
           E              N         P         K              C              A

CCT  CCT  571  GTT  GAA  580  TCT  AGA  589  CCA  TTT  598  TTC  ATC  607  AAA  AGG  616
 P    P   CTT   V    E   TCT   S    R   CCA   P    F   TTT   F    I   TTT   K    R   GAC
           L              S         P         F              F              D

TAC  GAA  625  CAT  GGT  634  TCT  GCA  643  ACA  TCC  652  ATA  CGT  661  ATT  AGG  670
 Y    E   ACA   H    G   GCA   S    A   TCC   T    S   TAT   I    R   TTC   I    R   GGT
           T              A         S         Y              F              G

CCT  TCC  679  TGT  CAG  688  AAC  TAC  697  ACA  CCT  706  GAA  GTG  715  ATA  CCC  724
 P    S   GAA   C    Q   AAC   N    Y   ACA   T    P   GGA   E    V   AAG   I    P   GGA
       E→a2  TGT            AAC         T              G              K              G
           C       ←a1
```

```
ATA GAC CTG GGG GAC GAG AAG ATC ATT AGG GGG ATC ATT CAG GGT AAG
 I   D   L   G   D   E   E   K   I   R   G   I   I   Q   G   X
                   1705        1714       1723  1732       1741  1750

CAC CGA GAG AAC AAG GTG GAG ATG AGG AAG TTC ATC AAG GGG TAC AAC
 R   R   E   N   K   V   E   M   R   K   F   I   K   G   Y   N
         1759            1768       1777       1786       1795  1804

GGC TCG GAC TGG AAG ATG ATC ATG GAT GAC AGC AAA CGC AAG TCT TTT
 G   S   D   W   K   M   I   M   D   D   S   K   R   K   S   F
     1813                1822       1831       1840       1849  1858

GAG GGC AAC AAC TAT GAT ACA CCT GAG AGC CTG CGG ACT CCA GCT TTT
 E   G   N   N   Y   D   T   P   E   S   L   R   T   P   A   F
     1867                1876       1885       1894       1903  1912

ACG TTC ATC AGG TAC CCC TAC CGG GAG AGA GCC ACT CAT TTT CTC TCC
 T   F   I   R   Y   P   Y   R   E   R   A   T   H   F   L   S
     1921                1930       1939       1948       1957  1966

AGA CGA CTG CTG TGT GGT GAA GTG GAA GCC CAT GGC ACA GGT GGG CTC
 R   R   L   L   C   G   E   V   E   A   H   G   T   G   G   L
     1975                1984       1993       2002       2011  2020

CCC AAC TTG GAT GAA TGT GAT GAC ACA GGT GCC AAC CCG ACC ACT
 P   N   L   D   E   C   D   D   -A  T   G   A   N   P   T   T
     2029                2038       2047       2056       2065  2074

GGA ACA GAT GAC CAG CTC ACA GGT GGC ACT GTG CTG GCC ACA CAC AGT
 G   T   D   D   Q   L   T   G   G   T   V   L   A   T   H   S
     2083                2092       2101       2110       2119  2128

AAG CCC ACG GTC ATA AGC AGC ACC ATA CAA TCA GAG TTT CCA ACA TAT GGT TTT
 K   P   T   V   I   S   S   T   I   Q   S   E   F   P   T   Y   G   F
     2137                2146       2155       2164       2173  2182
```

| | | | | | | | | |
|---|---|---|---|---|---|---|---|---|
| AAC | TGT | 2191 GAA | TTT | GGC | 2209 CAC | AGG | ACC | 2218 TTC | TGC | 2227 CAC | GAA | 2236 CAT | GAC |
| N | C | E | F | G | H | K | T | F | C | H | E | H | D |
| AAT | CAC | 2245 GTG | CAG | CTC | 2263 GTG | TTG | ACC | 2272 AGC | AAG | 2281 ACG | GGA | CCC | 2290 ATT | CAG |
| N | H | V | Q | L | V | L | T | S | K | T | G | P | I | Q |
| GAT | CAC | 2299 ACA | GGA | GAT | 2308 GGC | AAC | TTC | 2317 ATC | TAT | TCC | 2326 CAA | GCT | 2335 GAC | GAA | AAT | 2344 CAG | AAG |
| D | H | T | G | D | G | N | F | I | Y | S | Q | A | D | E | N | Q | K |
| GGC | AAA | 2353 GTG | GCT | CGC | 2362 CTG | GTG | AGC | 2371 CCT | GTG | TCC | 2380 TAT | GTC | 2389 AAC | GAC | TCT | 2398 CAG | CAC |
| G | K | V | A | R | L | V | S | P | V | S | Y | V | N | D | S | Q | H |
| TGC | ATG | 2407 ACC | TTC | TGG | 2416 TAT | CAC | GAT | 2425 TCT | ATG | GGG | 2434 CAC | TCC | 2443 ACA | CTC | CTC | 2452 AGG | GTC |
| C | M | T | F | W | Y | H | D | S | M | G | H | S | T | L | L | R | V |
| AAA | CTG | 2461 CGC | GCT | TTC | 2470 AAG | CCA | GAG | 2479 TCT | TAT | GAG | 2488 GAG | TCC | 2497 TGG | GGC | ATG | 2506 GCC | ATT |
| K | L | R | A | F | K | P | E | S | Y | E | E | S | W | G | M | A | I |
| AAA | CAA | 2515 GAC | CAG | CAG | 2524 CAC | TGG | AAG | 2533 GAA | GGG | CGT | 2542 GTC | TTG | 2551 CAC | AAG | TCT | 2560 CTG |
| K | Q | D | Q | Q | H | W | K | E | G | R | V | L | H | K | S | L |
| GGA | CAC | 2569 TAT | CAG | GTG | 2578 ATT | TTC | GAG | 2587 GGC | GAA | ATC | 2596 GGA | AAA | 2605 AAC | GGA | AAG | 2614 GGG |
| G | H | Y | Q | V | I | F | E | G | E | I | G | K | N | G | K | G |
| AAA | CTT | 2623 GTG | GAT | AGT | 2632 ATT | AAC | CAC | 2641 AAC | GGA | ATC | 2650 ATT | TCA | CAA | 2659 GAA | CTT | 2668 GGT | GCA |
| K | L | V | D | S | I | N | H | N | G | I | I | S | Q | E | L | G | A |
| ATT | GCT | 2623 GAT | GAC | | | | | | | | GAT | TGT | GCA |
| I | A | D | D | | | | | | | | D | C | A |

FIG 14E

| AAA | CCA | GCA | GAC | CTG | GAT | AAA | AAG | AAC | CCA | GAA | ATT | AAA | ATT | GAA | ACA | GGG |
|---|---|---|---|---|---|---|---|---|---|---|---|---|---|---|---|---|
| K | P | A | D | L | D | K | K | N | P | E | I | K | I | E | T | G |

| AGC | ACG | CCA | GGA | TAC | GAA | GGT | GAA | GGA | TAC | ATC | AAG | AAC | GAC | TCC | AGG | AAG |
|---|---|---|---|---|---|---|---|---|---|---|---|---|---|---|---|---|
| S | T | P | G | Y | E | G | E | G | Y | I | K | N | D | S | R | K |

| CCA | GGC | AAT | GTG | TTG | AAG | ACC | TTA | GAT | CCC | ATC | ATC | ACC | ATA | GCC | ATG |
|---|---|---|---|---|---|---|---|---|---|---|---|---|---|---|---|
| P | G | N | V | L | K | T | L | D | P | I | I | T | I | A | M |

(I→TM)

| AGT | GCC | CTG | GGG | GTC | CTC | CTG | GCT | GTC | TGT | GGG | TAC | TGT | GCC |
|---|---|---|---|---|---|---|---|---|---|---|---|---|---|
| S | A | L | G | V | L | L | A | V | C | G | Y | C | A |

| TGT | TGG | CAT | AAT | GGG | ATG | AAC | AGA | TCA | GAA | AAC | TTG | GCC | CTG | GAG | AAC | TAT | AAC |
|---|---|---|---|---|---|---|---|---|---|---|---|---|---|---|---|---|---|
| C | W | H | N | G | M | N | R | S | E | N | L | A | L | E | N | Y | N |

(C_TM←W)(H→cyto)

| TTT | GAA | CTT | GTG | GAT | GGT | GTG | AAG | TTG | AAA | GAC | AAA | CTG | AAT | ACA | CAG | AGT |
|---|---|---|---|---|---|---|---|---|---|---|---|---|---|---|---|---|
| F | E | L | V | D | G | V | K | L | K | D | K | L | N | T | Q | S |

| ACT | TAT | TCG | GAG | GCA | TGA | 3' (SEQ ID NO: 1) |
|---|---|---|---|---|---|---|
| T | Y | S | E | A | * | (SEQ ID NO: 2) |

(E_cyto←A)

FIG 14F

NEUROPILINS AND USE THEREOF IN METHODS FOR DIAGNOSIS AND PROGNOSIS OF CANCER

This application is a continuation of copending application International Application PCT/US98/26127 filed on Dec. 9, 1998 and which designated the U.S. which claims benefit of 60/069,155 filed Dec. 9, 1997 and 60/069,687 filed Dec. 12, 1997.

STATEMENT REGARD FEDERALLY SPONSORED RESEARCH

The work described herein was supported, in part, by National Institute of Health grants CA37392 and CA45548. The U.S. Government has certain rights to the invention.

FIELD OF THE INVENTION

The present invention provides methods for the diagnosis and prognosis of cancer, particularly metastatic cancer.

BACKGROUND OF THE INVENTION

Cancer, its development and treatment is a major health concern. The standard treatments available are few and directed to specific types of cancer, and provide no absolute guarantee of success. Most treatments rely on an approach that involves killing off rapidly growing cells in the hope that rapidly growing cancerous cells will succumb, either to the treatment, or at least be sufficiently reduced in numbers to allow the body's system to eliminate the remainder. However most, of these treatments are non-specific to cancer cells and adversely effect non-malignant cells. Many cancers although having some phenotype relationship are quite diverse. Yet, what treatment works most effectively for one cancer may not be the best means for treating another cancer. Consequently, an appreciation of the severity of the condition must be made before beginning many therapies. In order to most effective, these treatments require not only an early detection of the malignancy, but an appreciation of the severity of the malignancy. Currently, it can be difficult to distinguish cells at a molecular level as it relates to effect on treatment. Thus, methods of being able to screen malignant cells and better understand their disease state are desirable.

While different forms of cancer have different properties, one factor which many cancers share is that they can metastasize. Until such time as metastasis occurs, a tumor, although it may be malignant, is confined to one area of the body. This may cause discomfort and/or pain, or even lead to more serious problems including death, but if it can be located, it may be surgically removed and, if done with adequate care, be treatable. However, once metastasis sets in, cancerous cells have invaded the body and while surgical resection may remove the parent tumor, this does not address other tumors. Only chemotherapy, or some particular form of targeting therapy, then stands any chance of success.

The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., *Adv. Cancer Res.* 28, 149–250 (1978), Liotta, et al., *Cancer Treatment Res.* 40, 223–238 (1988), Nicolson, *Biochim. Biophy. Acta* 948, 175–224 (1988) and Zetter, V. *Eng. J. Med.* 322, 605–612 (1990)). Success in establishing metastatic deposits requires tumor cells to be able to accomplish these steps sequentially. Common to many steps of the metastatic process is a requirement for motility. The enhanced movement of malignant tumor cells is a major contributor to the progression of the disease toward metastasis. Increased cell motility has been associated with enhanced metastatic potential in animal as well as human tumors (Hosaka, et al., *Gann* 69, 273–276 (1978) and Haemmerlin, et al., *Int. J. Cancer* 27, 603–610 (1981)).

Identifying factors that are associated with onset of tumor metastasis is extremely important. In addition, to using such factors for diagnosis and prognosis, those factors are an important site for identifying new compounds that can be used for treatment and as a target for treatment identifying new modes of treatment such as inhibition of metastasis is highly desirable.

Tumor angiogenesis is essential for both primary tumor expansion and metastatic tumor spread, and angiogenesis itself requires ECM degradation (Blood et al., *Biochim. Biophys. Acta* 1032:89–118 (1990)). Thus, malignancy is a systemic disease in which interactions between the neoplastic cells and their environment play a crucial role during evolution of the pathological process (Fidler, I. *J. Cancer Metastasis Rev.* 5:29–49 (1986)).

There is mounting evidence that VEGF may be a major regulator of angiogenesis (reviewed in Ferrara, et al., *Endocr. Rev.*, 13, 18–32 (1992); Klagsbrun, et al., *Curr. Biol.*, 3, 699–702 (1993); Ferrara, et al., *Biochemi. Biophjs. Res. Commun.*, 161, 851–858 (1989) ). VEGF was initially purified from the conditioned media of folliculostellate cells (Ferrara, et al., *Biochem. Biophjs. Res. Common.*, 161, 851–858 (1989)) and from a variety of tumor cell lines (Myoken, et al., *Proc. Natl. Acad. Sci. USA*, 88:5819–5823 (1991); Plouet. et al., *EMBO. J.*, 8:3801–3806 (1991)). VEGF was found to be identical to vascular permeability factor, a regulator of blood vessel permeability that was purified from the conditioned medium of U937 cells at the same time (Keck, et al., *Science*, 246:1309–1312 (1989)). VEGF is a specific mitogen for endothelial cells (EC) in vitro and a potent angiogenic factor in vivo. The expression of VEGF is up-regulated in tissue undergoing vascularization during embryogenesis and the female reproductive cycle (Brier, et al., *Development*, 114:521–532 (1992); Shweiki, et al., *J. Clin. Invest.*, 91:2235–2243 (1993)). High levels of VEGF are expressed in various types of tumors, but not in normal tissue, in response to tumor-induced hypoxia (Shweiki, et al., *Nature* 359:843–846 (1992); Dvorak et al., *J. Exp. Med.*, 174:1275–1278 (1991); Plate, et al., *Cancer Res.*, 53:5822–5827; Ikea, et al., *J. Biol. Chem.*, 270:19761–19766 (1986)). Treatment of tumors with monoclonal antibodies directed against VEGF resulted in a dramatic reduction in tumor mass due to the suppression of tumor angiogeneis (Kim, et al., *Nature*, 382:841–844 (1993)). VEGF appears to play a principle role in many pathological states and processes related to neovascularization. Regulation of VEGF expression in affected tissues could therefore be key in treatment or prevention of VEGF induced neovascularization/angiogenesis.

VEGF exists in a number of different isoforms that are produced by alternative splicing from a single gene containing eight exons (Ferrara, et al., *Endocr. Rev.*, 13:18–32 (1992); Tischer, et al., *J. Biol. Chem.*, 806:11947–11954 (1991); Ferrara, et al., *Trends Cardio Med.*, 3:244–250 (1993); Polterak, et al., *J. Biol. Chem.*, 272:7151–7158 (1997)). Human VEGF isoforms consists of monomers of 121, 145, 165, 189, and 206 amino acids, each capable of making an active homodimer (Polterak et al., *J. Biol. Chem*, 272:7151–7158 (1997); Houck, et al., *Mol. Endocrinol.*, 8:1806–1814 (1991)). The $VEGF_{121}$ and $VEGF_{165}$ isoforms are the most abundant. $VEGF_{121}$ is the only VEGF isoforms that does not bind to heparin and is totally secreted into the culture medium. $VEGF_{165}$ is functionally different than $VEGF_{121}$ in that it binds to heparin and cell surface heparin sulfate proteoglycans (HSPGs) and is only partially released into the culture medium (Houck. et al., *J. Biol. Chem.*, 247:28031–28037 (1992): Park, et al., *Mol. Biol. Chem.*, 4:1317–1326 (1993)). The remaining isoforms are entirely associated with cell surface and extracellular matrix HSPGs (Houck, et al., *J. Biol. Chem.*, 247:28031–28037 (1992); Park, et al., *Mol. Biol. Chem.*, 4:1317–1326 (1993)).

VEGF receptor tyrosine kinases, KDR/Flk-1 and/or Flt-1, are mostly expressed by EC (Terman, et al., *Biochem. Biophys. Res. Commun.*, 187:1579–1586 (1992); Shibuya, et al., *Oncogene*, 5:519–524 (1990); De Vries, et al., *Science*, 265:989–991 (1992); Gitay-Goran, et al., *J. Biol. Chem.*, 287:6003–6096 (1992); Jakeman, et al., *J. Clin. Invest.*, 89:244–253 (1992)). It appears that VEGF activities such as mitogenicity, chemotaxis, and induction of morphological changes are mediated by KDR/Flk-1 but not Flt-1, even though both receptors undergo phosphorylation upon binding of VEGF (Millauer, et al., *Cell*, 72:835–846 (1993); Waltenberger, et al., *J. Biol. Chem.*, 269:26988–26995 (1994); Seetharam, et al., *Oncogene*, 10:135–147 (1995); Yoshida, et al., *Growth Factors*, 7:131–138 (1996)). Recently, Soker et al., identified a new VEGF receptor which is expressed on EC and various tumor-derived cell lines such as breast cancer-derived MDA-MB-231 (231) cells (Soker, et al., *J. Biol. Chem.*, 271:5761–5767 (1996)). This receptor requires the VEGF isoform to contain the portion encoded by exon 7. For example, although both $VEGF_{121}$ and $VEGF_{165}R$ bind to KDR/Flk-1 and Flt-1, only $VEGF_{165}$ binds to the new receptor. Thus, this is an isoform-specific receptor and has been named the $VEGF_{165}$ receptor ($VEGF_{165}R$). It will also bind the 189 and 206 isoforms. $VEGF_{165}R$ has a molecular mass of approximately 130 kDa, and it binds $VEGF_{165}$ with a Kd of about $2 \times 10^{-10}M$, compared with approximately $5 \times 10^{-12}M$ for KDR/Flk-1. In structure-function analysis, it was shown directly that $VEGF_{165}$ binds to $VEGF_{165}R$ via its exon 7-encoded domain which is absent in $VEGF_{121}$ (Soker, et al., *J. Biol. Chem.*, 271:5761–5767 (1996)). However, the function of the receptor was unclear.

Identifying the alterations in gene expression which are associated with malignant tumors, including those involved in tumor progression and angiogenesis, is clearly a prerequisite not only for a full understanding of cancer, but also to develop new rational therapies against cancer.

A further problem arises, in that the genes characteristic of cancerous cells are very often host genes being abnormally expressed. It is quite often the case that a particular protein marker for a given cancer while expressed in high levels in connection with that cancer is also expressed elsewhere throughout the body, albeit at reduced levels.

Prostatic carcinoma is the most prevalent form of cancer in males and the second leading cause of cancer death among older males (Boring, et al., *Cancer J. Clinicians*, 7–26 (1994)). Clinically, radical prostatectomy offers a patient with locally contained disease an excellent chance for cure. Unfortunately, if diagnosed after metastases are established, prostatic cancer is a fatal disease for which there is no effective treatment to significantly increase survival. Recent advances in prostatic cancer diagnosis has allowed the earlier detection of human prostate cancer by use of the PSA test (Catalona, et al., *J. Urol.*, 151, 1283–1290 (1994)). Unfortunately, this early detection has not been accompanied by an improvement in determining which tumors may progress to the metastatic stage (Cookson, et al., *J. Urology* 154, 1070–1073 (1995) and Aspinall, et al., *J. Urology* 154, 622–628 (1995)). Since many individuals having prostate cancer are not adversely effected by the cancer, considerable controversy has arisen as to the use of such tests. Thus, methods for early detection and early appreciation of the potential for or of the severity of the cancer, that can be taken into account in treatment of, for example, metastatic disease, as well as treatment of such diseases are desirable.

SUMMARY OF THE INVENTION

We have isolated a cDNA encoding the $VEGF_{165}$ R gene (SEQ ID NO:1) and have deduced the amino acid sequence of the receptor (SEQ ID NO:2) We have discovered that this novel VEGF receptor is structurally unrelated to Flt-1 or KDR/Flk-1 and is-expressed not only by endothelial cells but by non-endothelial cells, including surprisingly tumor cells.

In ascertaining the function of the $VEGF_{165}R$ we have further discovered that this receptor has been identified as a cell surface mediator of neuronal cell guidance and called neuropilin-1. Kolodkin et al., *Cell* 90:753–762 (1997). We refer to the receptor as $VEGF_{165}R/NP$-1.

In addition to the expression cloning of $VEGF_{165}R/NP$-1 cDNA we isolated another human cDNA clone whose predicted amino acid sequence was 47% homologous to that of $VEGF_{165}R/NP$-1 and over 90% homologous to rat neuropilin-2 (NP-2) which was recently cloned (Kolodkin, et al., *Cell* 90, 753–762 (1997)). NP-2 binds members of the collapsin/semaphorin family selectively (Chen, et al., *Neuron* 19, 547–559 (1997)).

Our results indicate that $VEGF_{165}R/NP$-1 and NP-2 are expressed by both endothelial and tumor cells. (FIG. 19) We have shown that endothelial cells expressing both KDR and $VEGF_{165}R/NP$-1 respond with increased chemotaxis towards $VEGF_{165}$, not $VEGF_{121}$, when compared to endothelial cells expressing KDR alone. While not wishing to be bound by theory, we believe that $VEGF_{165}R/NP$-1 functions in endothelial cells to mediate cell motility as a co-receptor for KDR.

We have also shown in the Boyden chamber motility assay that $VEGF_{165}$ stimulates 231 breast carcinoma cell motility in a dose-response manner (FIG. 15A). $VEGF_{121}$ had no effect motility of these cells (FIG. 15B). Since tumor cells such as, 231 cells, do not express the VEGF receptors, KDR or Flt-1, while not wishing to be bound by theory, we believe that tumor cells are directly responsive to $VEGF_{165}$ via $VEGF_{165}R/NP$-1.

We have also analyzed two variants of Dunning rat prostate carcinoma cells, AT2.1 cells, which are of low motility and low metastatic potential, and AT3.1 cells, which are highly motile and metastatic. Cross-linking and Northern blot analysis show that AT3.1 cells express abundant $VEGF_{165}R/NP$-1, capable of binding $VEGF_{165}$, while AT2.1 cells don't express $VEGF_{165}R/NP$-1 (FIG. 18). Immunostaining of tumor sections confirmed the expression of $VEGF_{165}R/NP$-1 in AT3.1, but not AT2.1 tumors (FIG. 17). Additionally, immunostaining showed that in subcutaneous AT3.1 and PC3 tumors, the tumor cells expressing $VEGF_{165}R/NP$-1 were found preferentially at the invading front of the tumor/dermis boundary (FIG. 17). Furthermore, stable clones of AT2.1 cells overexpressing $VEGF_{165}R/NP$-1 had enhanced motility in the Boyden chamber assay. These results indicate that $VEGF_{165}R/NP$-1 expression on tumor cells is associated with the motile, metastatic phenotype.

These results indicate that enhanced transcripts (mRNA) and expression of the $VEGF_{165}R/NP-1$ and NP-2 receptors have a high correlation to disease state in a number of cancers, such as prostate, hemangioendothelioma and breast, particularly metastatic cancers. Accordingly, assaying for enhanced levels of transcript or gene product can be used in not only a diagnostic manner, but in a prognostic manner for particular cancers. Additionally, by blocking such receptors or inhibiting their occurrence, one can inhibit metastasis.

The present invention provides a method of diagnosing cancer, especially prostate cancer, breast cancer, and hemanyioendothelioma in a patient by measuring levels of $VEGF_{165}R/NP-1$ or NP-2 in a biological specimen obtained from the patient. Levels of $VEGF_{165}R/NP-1$ or NP-2 in the sample greater than a base line level for that type of specimen is indicative of cancer. Biological specimens include, for example, blood, tissue, serum, stool, urine, sputum, cerebrospinal fluid and supernatant from cell lysate. The determination of base lines and comparison levels is by standard modes of analysis based upon the present disclosure.

In another aspect, the present invention provides a method of prognosis in an individual having cancer, the method comprising:

a. obtaining a tumor sample from said individual;

b. measuring $VEGF_{165}R/NP-1$ or NP-2 amounts to obtain an $VEGF_{165}R/NP-1$ level in said sample;

c. correlating said $VEGF_{165}R/NP-1$ levels with a baseline level; and correlating levels of $VEGF_{165}R/NP-1$ or NP-2 higher than the baseline with an indication of unfavorable prognosis and levels of $VEGF_{165}R/NP-1$ or NP-2 at the baseline or less with a favorable prognosis. $VEGF_{165}R/NP-1$ mRNA or protein may be measured to obtain $VEGF_{165}R/NP-1$ levels.

In accordance with the present invention, expression of $VEGF_{165}R/NP-1$ or NP-2 in a tumor sample greater than a base line level for that particular tissue indicates a higher risk of tumor metastasis.

In yet another aspect, the present invention provides a method for determining the metastatic potential of a tumor by measuring the level of $VEGF_{165}R/NP-1$ or NP-2 expression in the tumor. Expression of $VEGF_{165}R/NP-1$ or NP-2 in said tumor greater than a base line level for that particular tissue indicates an increased metastatic potential.

In yet another embodiment, changes in condition can be monitored by comparing changes in $VEGF_{165}R/NP-1$ or NP-2 expression levels in the tumor in that subject over time.

In the methods of the present invention, levels of $VEGF_{165}R/NP-1$ or NP-2 can be ascertained by measuring the protein directly or indirectly by measuring transcript (mRNA) encoding $VEGF_{165}R/NP-1$ or NP-2. mRNA levels can be measured, for example, using an RNA dependent polymerase chain reaction. e.g., reverse transcriptase PCR or Northern blot analysis. DNA chip technology may also be used to measure mRNA levels.

Base line levels can readily be determined by measuring levels of $VEGF_{165}R/NP-1$ or NP-2.in sample of disease free individuals.

The present invention also provides of a method for measuring $VEGF_{165}R/NP-1$ or NP-2 levels in non-neuronal tissues which comprises the steps of:

a. contacting a biological specimen with an antibody or antibody fragment which selectively binds $VEGF_{165}R/NP-1$ or NP-2, and b. detecting whether said antibody or said antibody fragment is bound by said sample and thereby measuring the levels of $VEGF_{165}R/NP-1$ or NP-2.

In still another embodiment of this invention, the receptor can serve as a target for compounds that disrupt its function. Such compounds include, for example, VEGF antagonists, compounds that bind to NP-1 or NP-2 and antibodies that specifically binds the receptor at a region that inhibits receptor function. For example, one can add an effective amount of a compound that binds to NP-1 to disrupt receptor and thus inhibit metastasis. In another embodiment, one can use such $VEGF_{165}R/NP-1$ or NP-2 cells in an assay to discover compounds that bind to or otherwise interact with these receptors in order to discover compounds that can be used to inhibit metastasis.

Other aspects of the invention are disclosed infra.

BRIEF DESCRIPTION OF THE DRAWINGS

FIG. 2A shows COS 7 cells were transfected with a primary plasmid pool (#55 of the 231 cell library) representing approximately $3 \times 10^3$ clones and one COS 7 cell binding $^{125}I$-VEGF165 in the first round of screening is shown.

FIG. 2 shows several COS 7 cells transfected with a single positive cDNA clone (A2) binding $^{125}I$-$VEGF_{165}$ after the third round of screening.

FIG. 3 shows the Deduced Amino Acid Sequence of Human $VEGF_{165}R/NP-1$ (SEQ ID NO:3). The deduced 923 amino acid sequence of the open reading frame of $VEGF_{165}R/NP-1$, clone A2 (full insert size of 6.5 kb) is shown. The putative signal peptide sequence (amino acids 1–21) and the putative transmembrane region (amino acids 860–883) are in boxes. The amino acid sequence obtained by N-terminal amino acid sequencing (FIG. 3, amino acids 22–39) is underlined. The arrow indicates where the signal peptide has been cleaved and removed, based on comparison of the N-terminal sequence of purified $VEGF_{165}R/NP-1$ and the cDNA sequence. The sequence of human $VEGF_{165}R/NP-1$ reported here differs from that reported by He et at. (He and Tessier-Lavigne, *Cell* 90, 739–751 (1997)) in that we find $Lys_{26}$ rather than $Glu_{26}$, and $Asp_{855}$ rather than $Glu_{855}$ $Lys_{26}$ and $Asp_{855}$ are found, however, in mouse and rat $VEGF_{165}R/NP-1$ (Kwakami et al., *J. Neuroiol.* 29, 1–17 (1995): He and Tessier-Lavigne, *Cell* 90, 739–751 1997).

FIGS. 4A and 4B show the Comparison of the Deduced Amino Acid Sequence of Human $VEGF_{165}R/NP-1$ (SEQ ID NO:2) and NP-2 (SEQ ID NO.:4). The deduced open reading frame amino acid sequences of VEGF$_{165}$R/NP-1 and NP-2 are aligned using the DNASIS program. Amino acids that are identical in both open reading frames are shaded. The overall homology between the two sequences is 43%.

FIG. 7A. Increasing amounts of $^{125}$I-VEGF$_{165}$ (0.1–50 ng/ml) were added to subconfluent cultures of PAE cells transfected with human VEGF$_{165}$R/NP-1 cDNA (PAE/NP-1 cells) in 48 well dishes. Non-specific binding was determined by competition with a 200-fold excess of unlabeled VEGF$_{165}$. After binding, the cells were washed lysed and the cell-associated radioactivity was determined using a γ counter.

FIG. 7B. The binding data shown in FIG. 7A were analyzed by the method of Scatchard, and a best fit plot was obtained with the LIGAND program (Munson and Rodbard, 1980). PAE/NP-1 cells express approximately $3 \times 10^5$ VEGF$_{165}$ binding sites per cell and bind $^{125}$I-VEGF$_{165}$ with a $K_d$ of $3.2 \times 10^{-10}$ M.

A single KDR receptor or a KDR-VEGF$_{165}$R/NP-1 pair is shown in top portion. An expanded view showing several receptors is shown in the bottom portion. VEGF$_{165}$ binds to KDR via exon 4 and to VEGF$_{165}$R/NP-1 via exon 7 (Keyt et al. *J. Biol. Chem.* 271,5638–5646 (1996b); Soker et al., *J. Biol. Chem.* 271, 5761–5767 (1996)). A rectangular VEGF165 molecule represents a suboptimal conformation that doesn't bind to KDR efficiently while a rounded VEGF$_{165}$ molecule represents one that fits better into a binding site. In cells expressing KDR alone, VEGF$_{165}$ binds to KDR in a sub-optimal manner. In cells co-expressing KDR and VEGF$_{165}$R/NP-1, the binding efficiency of VEGF$_{165}$ to KDR is enhanced. It may be that the presence of VEGF$_{165}$R/NP-1 increases the concentration of VEGF$_{165}$ on the cell surface, thereby presenting more growth factor to KDR. Alternatively, VEGF$_{165}$R/NP-1 may induce a change in VEGF$_{165}$ conformation that allows better binding to KDR, or both might occur. In the presence of GST-Ex 7+8, VEGF$_{165}$ binding to VEGF$_{165}$R/NP-1 is competitively inhibited and its binding to KDR reverts to a sub-optimal manner.

FIG. 12 shows the human NP-2 amino acid sequence (SEQ ID NO:4).

FIGS. 13A–13C show the human NP-2 DNA sequence (SEQ ID NO:3).

Figure 14B:
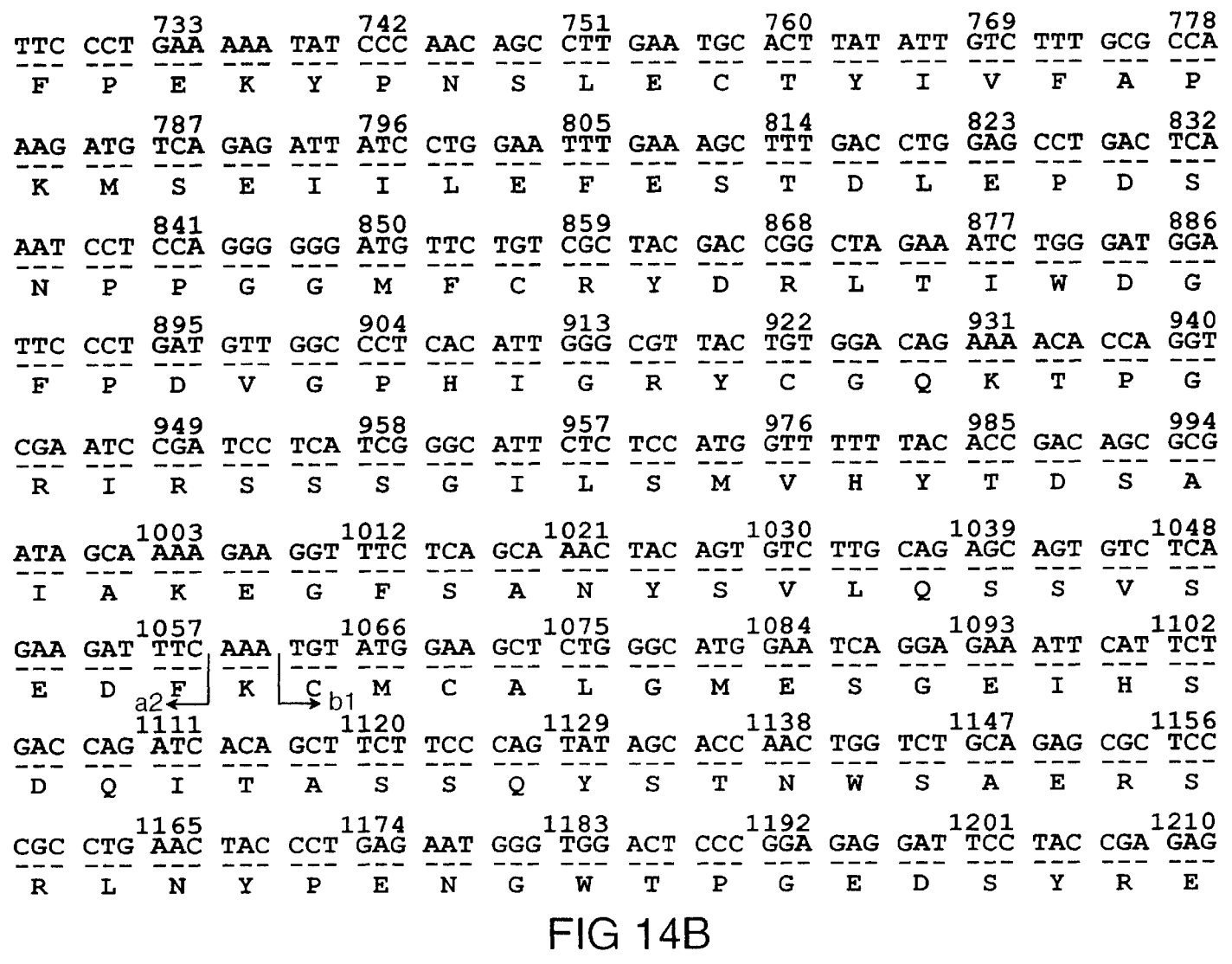
Figure 14C:
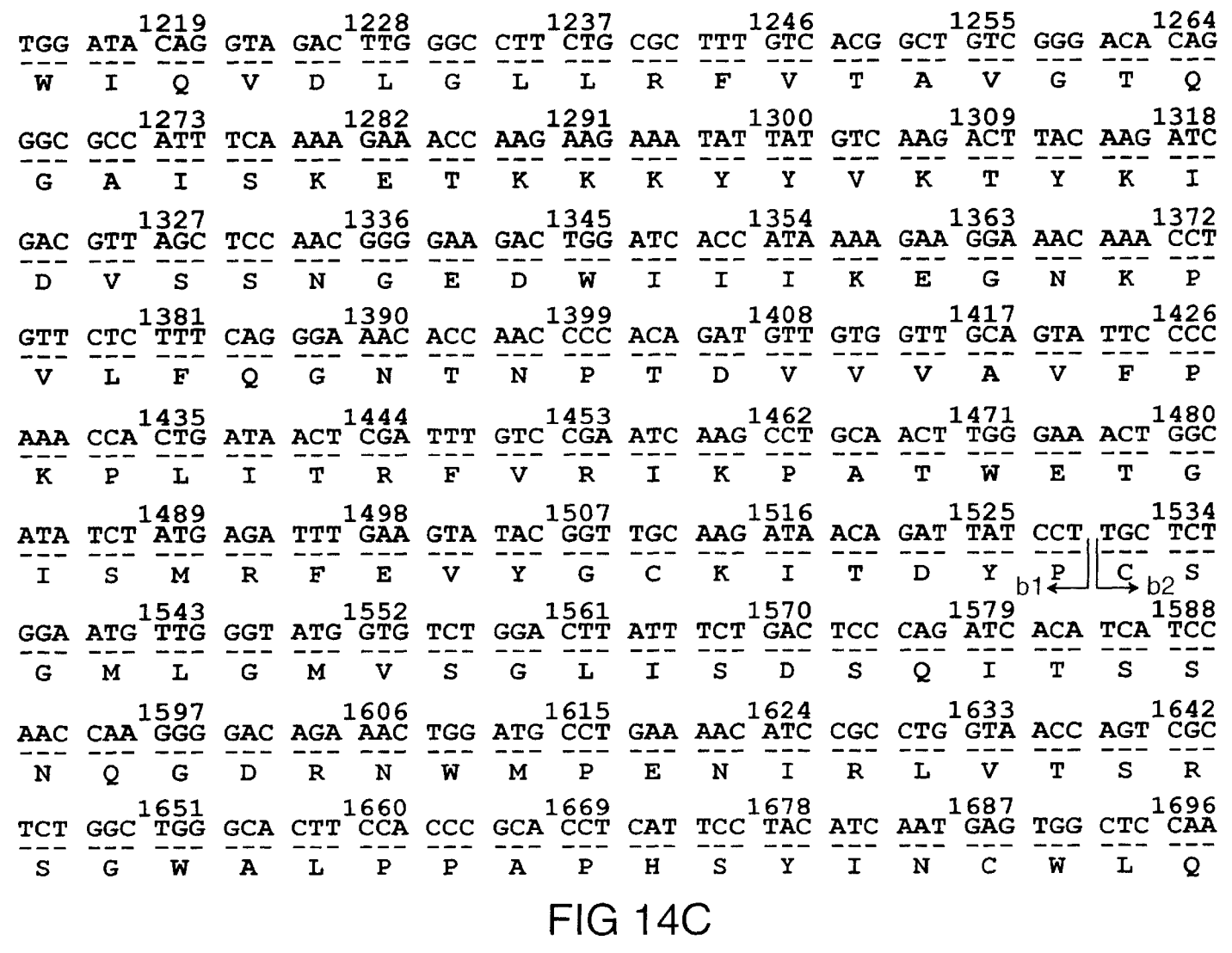

FIGS. 14A–14F show the nucleotide (SEQ ID NO:1) and amino acid sequences (SEQ ID NO:2) of VEGF$_{165}$R/NP-1.

Figure 15A:
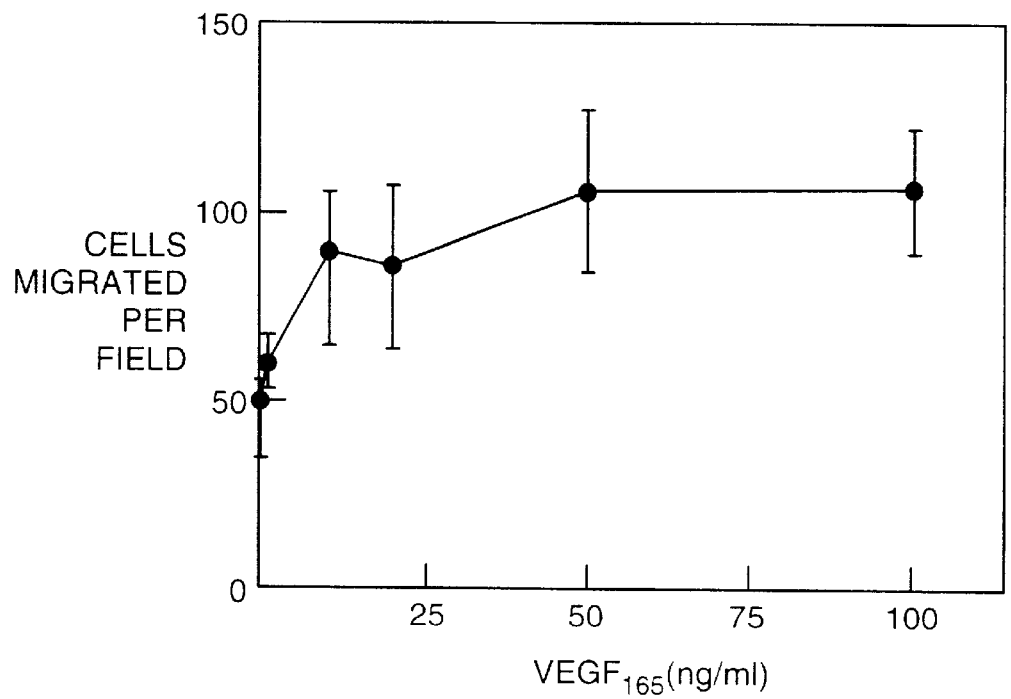
Figure 15B:
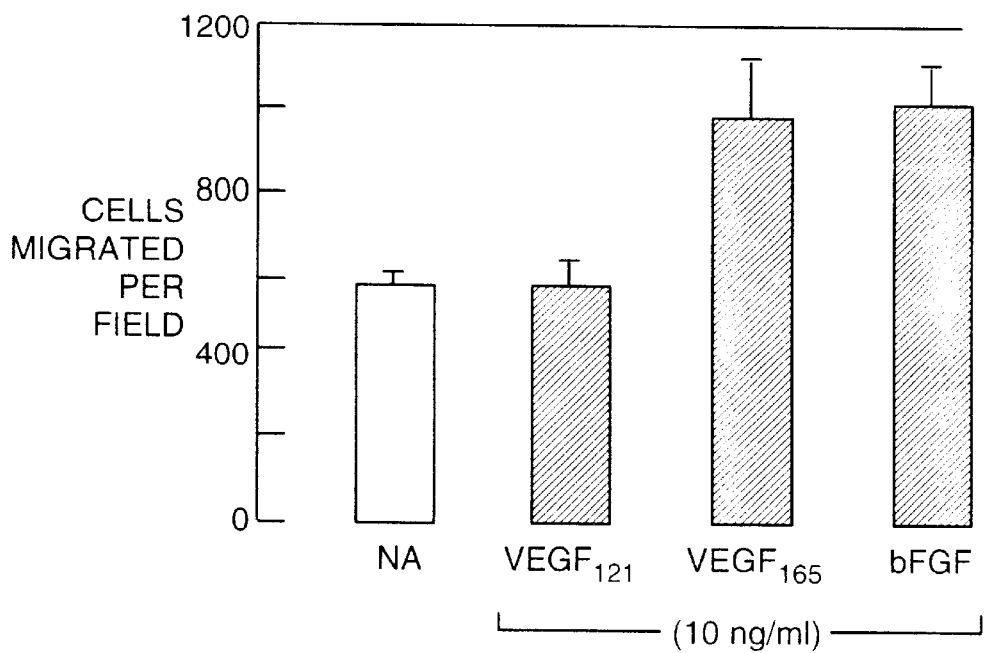

FIGS. 15A and 15B show VEGF$_{165}$ stimulation of MDA MB 231 cell motility. (FIG. 15A) Dose response of VEGF$_{165}$ motility activity. (FIG. 15B) Both VEGF$_{165}$ and bFGF stimulate motility but VEGF$_{121}$ does not.

Figure 16A:
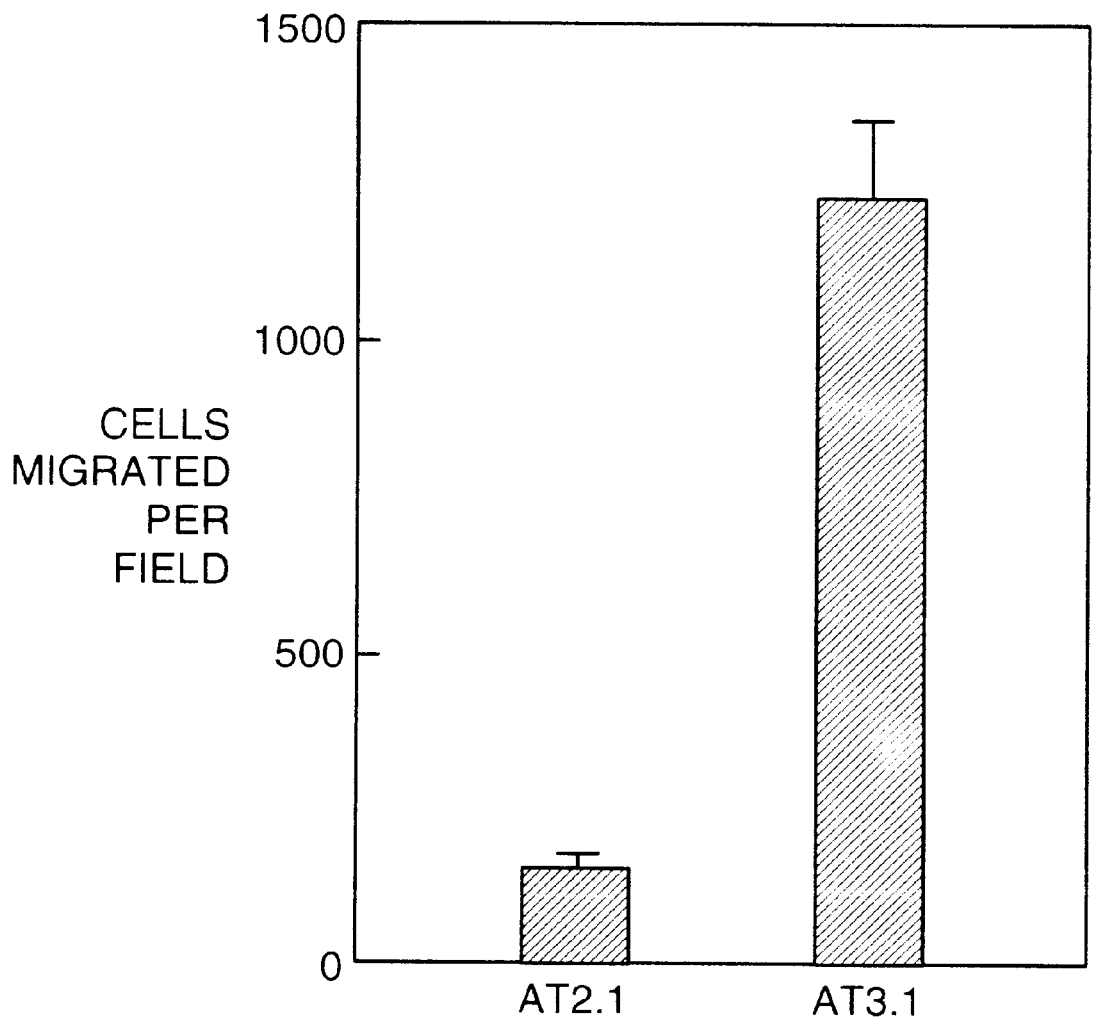
Figures 16B, 16C:
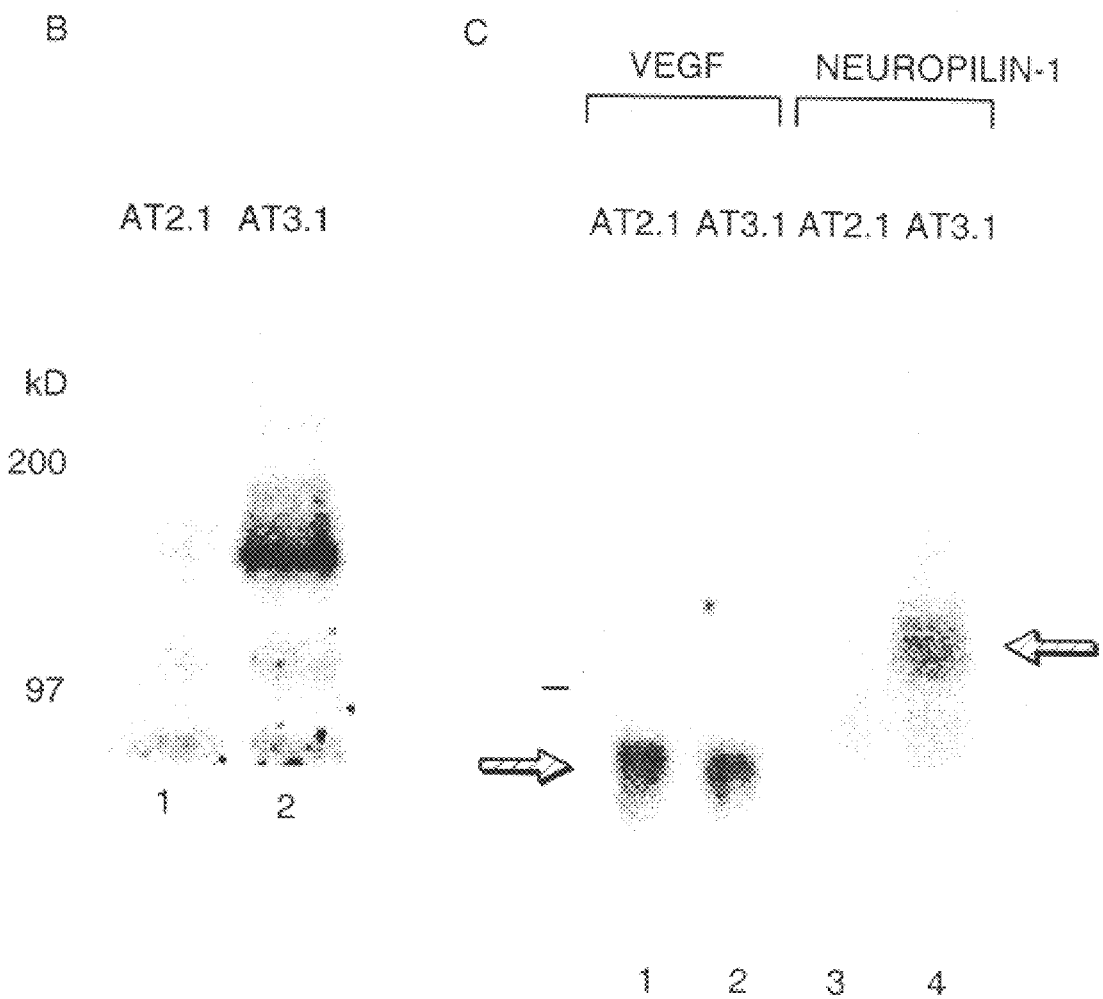

FIGS. 16A, 16B and 16C show motility and neuropilin-1 expression of Dunning rat prostate carcinoma cell lines AT3-1 (high motility, high metastatic potential) and AT2.1 (low motility, low metastatic potential) cells. (FIG. 16A) AT3.1 cells are more motile than AT2.1 cells in a Boyden chamber assay. (FIG. 16B) $^{125}$I-VEGF$_{165}$ cross-links neuropilin-1 on AT3.1 cells but does not cross-link to AT2.1 cells. (FIG. 16C) AT3.1 but not AT2.1 cells express neuropilin-1, while both cell types express VEGF.

Figure 17A:
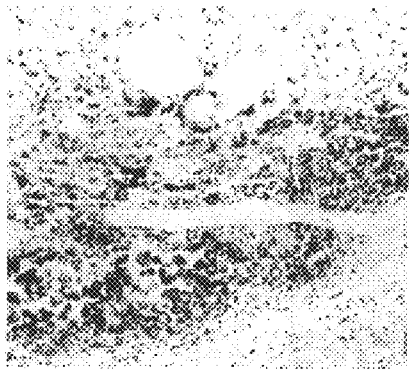
Figure 17B:
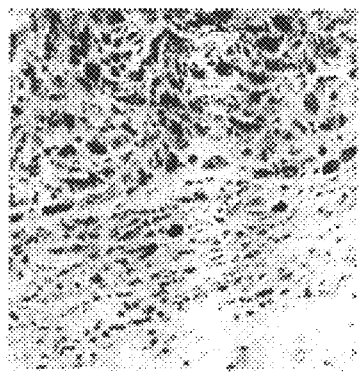
Figure 17C:
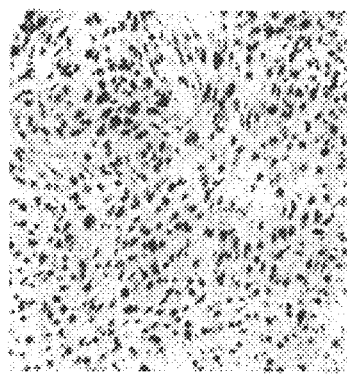

FIGS. 17A, 17B and 17C show immunostaining of (FIG. 17A) a PC3 subcutaneous tumor in a nude mouse, (FIG. 17B) an AT3.1 tumor in a rat, (FIG. 17C) an AT2.1 tumor in rat with anti-neuropilin-1 antibodies. Neuropilin immunostaining is preferentially associated with PC3 and AT3.1 tumor cells at the tumor/dermis boundary. Some of these cells cluster around blood vessels. AT2.1 cells do not express neuropilin-1.

Figure 18A:
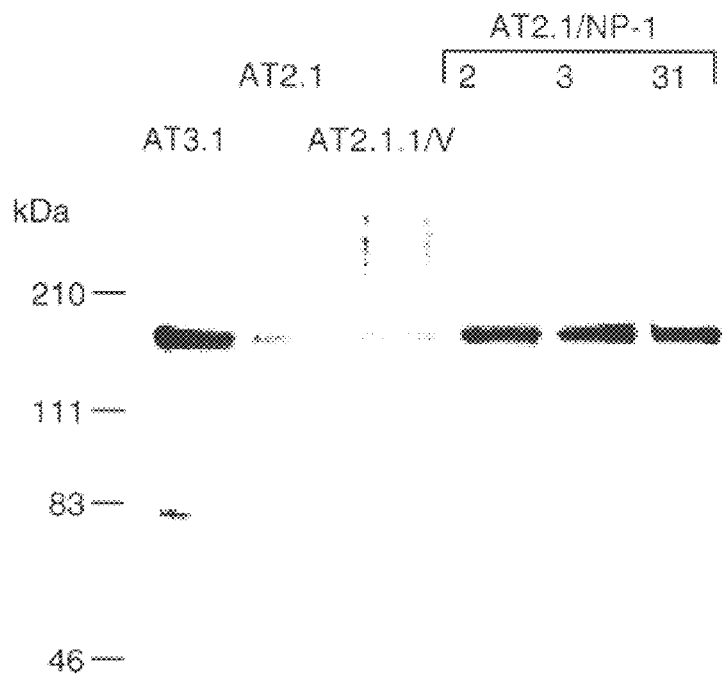
Figure 18B:
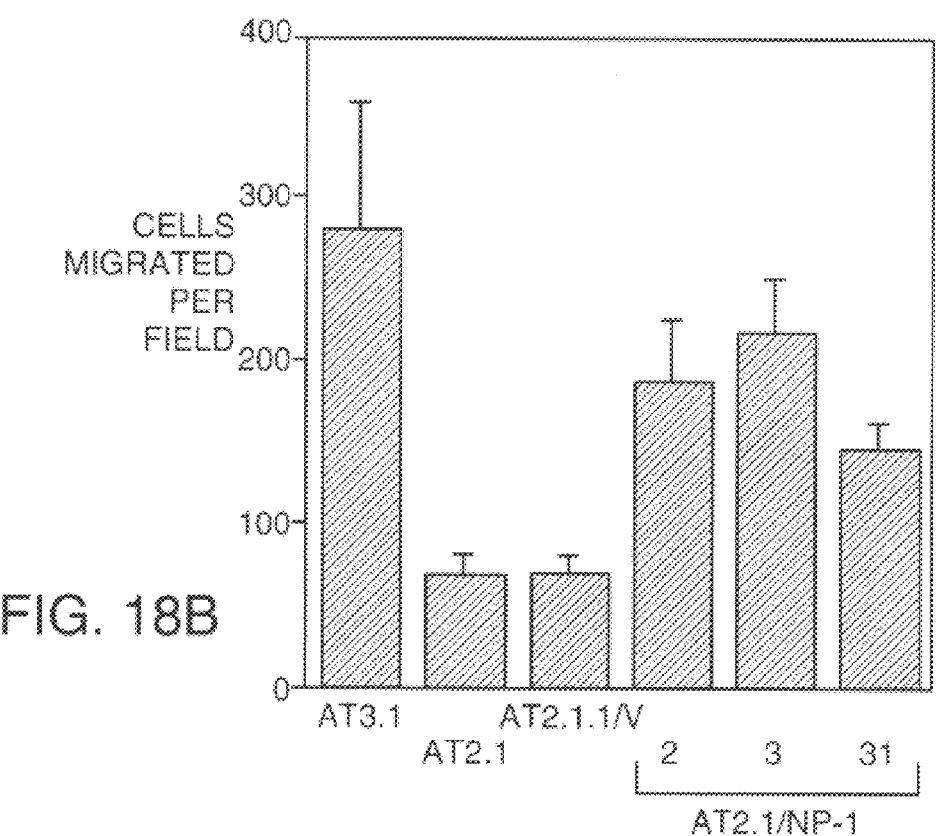

FIGS. 18A and 18B show overexpression of neuropilin-1 in AT2.1 cells. (FIG. 18A) Western blot, (FIG. 18B) motility activity. Three AT2.1 clones (lanes 4,5,6) express higher amounts of neuropilin-1 protein and are more motile compared to parental AT2.1 cells or AT2.1 vector (AT2.1/V) controls and approach AT3.1 cell neuropilin-1 levels and migration activity.

Figure 19:
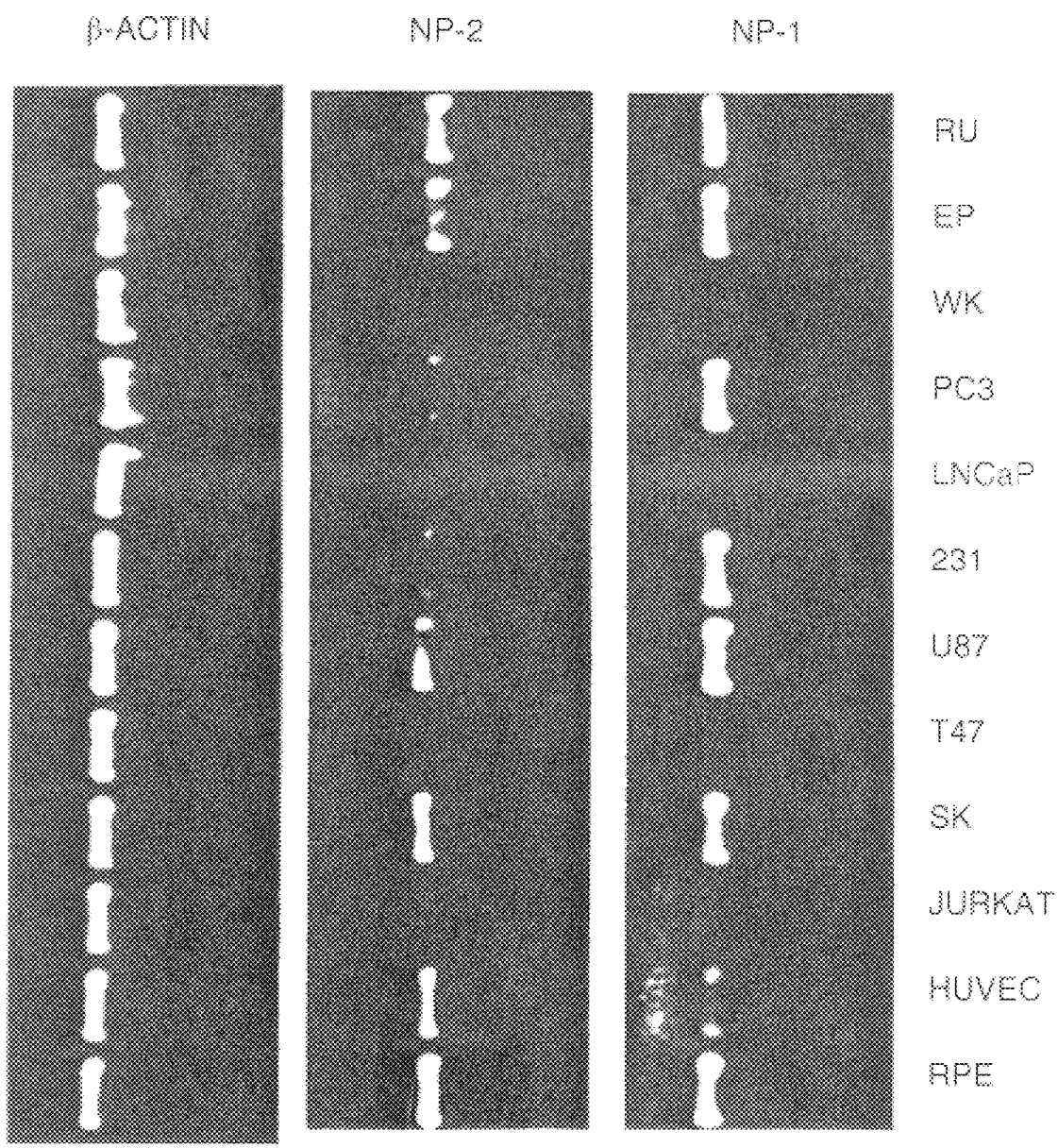

FIG. 19 shows expression of NP-1, NP-2 and β-actin in cancer cell lines and endothelial cells using reverse transcriptase PCR following primers:

Human NP-1
Forward (328–351): 5'TTTCGCAACGATAAATGTGGC-GAT 3' (SEQ ID NO:7)
Reverse (738–719): 5'TATCACTCCACTAGGTGTTG 3' (SEQ ID NO:8)

Human NP-2
Forward (513–532): 5'CCAACCAGAAGATTGTCCTC 3' (SEQ ID iNO:9)
Reverse (1181–1162): 5'GTAGGTAGATGAGGCACTGA 3' (SEQ ID NO:10)

DETAILED DESCRIPTION OF THE INVENTION

We have discovered that there are VEGF receptors (VEGFR) and neuropilins such as $VEGF_{165}R$/NP-1 and NP-2 that are associated with metastatic potential of a malignant cell. Preferred ones are $VEGF_{165}R$/NP-1 and NP-2 but any neuropilin or VEGFR, where the constituents share at least about 85% homology with either of the above $VEGF_{165}R$/NP-1 and NP-2 can be used. More preferably, such constituent shares at least 90% homology. Still more preferably, each constituent shares at least 95% homology.

Homology is measured by means well known in the art. For example % homology can be determined by any standard algorithm used to compare homologies.

These include, but are not limited to BLAST 2.0 Registered Trademark such as BLAST 2.0.4 and i. 2.0.5 available from the National Institutes of Health (Altschul, S. F., et al. Nucleic Acids Res. 25: 3389–3402 (1997)) and DNASIS Registered Trademark (HitachiSoftware Engineering America, Ltd.). These programs should preferably be set to an automatic setting such as the standard default setting for homology comparisons. As explained by the NIH, the scoring of gapped results tends to be more biologically meaningful than ungapped results.

For ease of reference, this disclosure will generally talk about $VEGF_{165}R$/NP-1 and NP-2 and/or homologs thereof but all teaching are applicable to the above-described homologs.

In another embodiment a VEGFR can be used as long as it binds to a sequence having at least 90%, more preferably 95% homology to exon 7 of $VEGF_{165}$.

These VEGF receptors and neuropilins, e.g., $VEGF_{165}R$/NP-1 and NP-2, are associated with both tumor metastases and angiogenesis. We have shown that expression of $VEGF_{165}R$/NP-1 and NP-2 is upregulated in highly metastatic prostate cancer cell lines relative to poorly metastatic or nonmetastatic lines. Thus, expression of $VEGF_{165}R$/NP-1 and NP-2 can be used to determine metastatic potential. In addition, the receptor and the component provide a target for treatments to inhibit the metastasis process.

Accordingly, the evaluation and comparison of levels of transcript (mRNA) or gene product, either normal or mutated, in non-neuronal tissue can be both diagnostic and prognostic of particular cancer. For example, an elevated level is indicative of a greater tendency for metastatic activity. Conversely, lower levels than certain baselines can also be used to indicate the metastatic potential of the tumor. Further, by monitoring a particular neoplastic growth over a period of time and comparing changes in level one can evaluate changes in metastatic activity.

The present invention provides a method of diagnosing cancer, preferably prostate and breast cancer, in a patient by measuring levels of $VEGF_{165}R$/NP-1 or NP-2 in a biological specimen obtained from the patient. Levels of $VEGF_{165}R$/NP-1 or NP-2 in the sample greater than a base line level is indicative of cancer. Baseline levels can readily be determined by measuring levels of $VEGF_{165}R$/NP-1 or NP-2 in a sample of disease free individuals. Additionally, baselines can be obtained by measuring individuals having cancer over the course of the malignancy.

Biological specimens include, for example, blood, tissue, serum, stool, urine, sputum, cerebrospinal fluid and supernatant from cell lysate. Preferably,-one uses tissue specimens. The determination of base lines and comparison levels is by standard modes of analysis based upon the present disclosure.

The present invention also provides a method of prognosis in an individual having cancer, preferable prostate, breast cancer and melanoma by measuring levels of $VEGF_{165}R$/NP-1 or NP-2 in a tumor sample obtained from a patient to be tested. Expression of $VEGF_{165}R$/NP-1 or NP-2 in said tumor sample greater than a base line level for that particular tissue indicates a higher risk of tumor metastasis. This information can be used by the physician in determining the most effective course of treatment.

Changes in a patients condition can be monitored using the methods of the present invention by comparing changes in $VEGF_{165}R$/NP-1 or NP-2 expression levels in the tumor in that subject over time. For example, determining whether the level stabilizes or preferably declines.

The present invention further provides a method for determining the metastatic potential of a tumor by measuring the level of $VEGF_{165}R$/NP-1. or NP-2 expression in the tumor. Expression of $VEGF_{165}R$/NP-1 or NP-2 in said tumor greater than a base line level for that particular tissue indicates an increased metastatic potential.

Standard detection techniques well known in the art for detecting RNA, DNA, proteins and peptides can readily be applied to detect $VEGF_{165}R$/NP-1 or NP-2 or its transcript to diagnose cancer, especially metastatic cancer or to confirm that a primary tumor has, or has not, reached a particular metastatic phase.

Such techniques may include detection with nucleotide probes or may comprise detection of the protein by, for example, antibodies or their equivalent. Preferably, the nucleotide probes hybridize to the sequence shown in SEQ ID NO:1 for $VEGF_{165}R$/NP-1. and SEQ ID NO:3 for NP-2. A VEGFR/NP-1 homolog has at least about 85% homology to the amino acid sequence encoded by SEQ ID NO:1, whereas a VEGFR/NP-2 homolog has at least about 85% homology to the amino acid sequence encoded by SEQ ID NO:3.

Types of probe include cDNA, riboprobes, synthetic oligonucleotides and genomic probes. The type of probe used will generally be dictated by the particular situation, such as riboprobes for in situ hybridization, and cDNA for Northern blotting, for example. The most preferred probes are those which correspond to the cytoplasmic domain of the receptor. Most preferably, the probe is directed to nucleotide regions unique to the receptor. Detection of the $VEGF_{165}R/NP\text{-}1$ or NP-2 encoding gene, per se, will be useful in screening for mutations associated with enhanced expression. Other forms of assays to detect targets more readily associated with levels of expression—transcripts and other expression products will generally be useful as well. The probes may be as short as is required to differentially recognize $VEGF_{165}R/NP\text{-}1$ or NP-2 mRNA transcripts, and may be as short as, for example, 15 bases, however, probes of at least 17 bases, more preferably 18 bases and still more preferably 20 bases are preferred.

A probe may also be reverse-engineered by one skilled in the art from the amino acid sequence of SEQ ID NO:2 ($VEGF_{165}R/NP\text{-}1$) or SEQ ID NO:4 (NP-2). However use of such probes may be more limited than the native DNA sequence, as it will be appreciated that any one given reverse-engineered sequence will not necessarily hybridize well, or at all with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases. Other forms of labeling may include enzyme or antibody labeling such as is characteristic of ELISA.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes, radiolabeled cDNA or RNA is then hybridized to the preparation, washed and analyzed by autoradiography.

In situ hybridization visualization may also be employed, wherein a radioactively labeled antisense cRNA probe is hybridized with a thin section of a biopsy sample, washed, cleaved with RNase and exposed to a sensitive emulsion for autoradiography. The samples may be stained with haematoxylon to demonstrate the histological composition of the sample, and dark field imaging with a suitable light filter shows up the developed emulsion. Non-radioactive labels such as digoxicenin may also be used.

Immunohistochemistry may be used to detect expression of human $VEGF_{165}R/NP\text{-}1$ or NP-2 in a biopsy sample. A suitable antibody is brought into contact with, for example, a thin layer of cells, washed, and then contacted with a second, labeled antibody. Labeling may be by enzyme, such as peroxidase, avidin or by radiolabelling. Chromogenic labels are generally preferable, as they can be detected under a microscope.

More generally preferred is to detect the protein by immunoassay, for example by ELISA or RIA, which can be extremely rapid. Thus, it is generally preferred to use antibodies, or antibody equivalents, to detect $VEGF_{165}R/NP\text{-}1$ or NP-2.

It may not be necessary to label the substrate, provided that the product of the enzymatic process is detectable and characteristic in its own right (such as hydrogen peroxide for example). However, if it is necessary to label the substrate, then this may also comprise enzyme labeling, labeling with radioisotopes, antibody labeling, fluorescent marker labeling or any other suitable form which will be readily apparent to those skilled in the art.

Antibodies may be prepared as described below, and used in any suitable manner to detect expression of $VEGF_{165}R/NP\text{-}1$ or NP-2. Antibody-based techniques include ELISA (enzyme linked immunosorbent assay) and RIA (radioimmunoassay). Any conventional procedures may be employed for such immunoassays. The procedures may suitably be conducted such that a $VEGF_{165}R/NP\text{-}1$ or NP-2 standard is labeled with a radioisotope such as $^{125}I$ or $^{35}S$, or an assayable enzyme, such as horseradish peroxidase or alkaline phosphatase and, together with the unlabelled sample, is brought into contact with the corresponding antibody, whereon a second antibody is used to bind the first and radioactivity or the immobilized enzyme assayed (competitive assay), alternatively. $VEGF_{165}R/NP\text{-}1$ or NP-2 in the sample is allowed to react with the corresponding immobilized antibody, radioisotope- or enzyme-labeled anti-receptor antibody is allowed to react with the system and radioactivity or the enzyme assayed (ELISA-sandwich assay). Other conventional methods may also be employed as suitable.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radio-labeling of receptor and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect VEGF$_{165}$R/NP-1 or NP-2 according to a practitioner's preference based upon the present disclosure. One such technique is Western blotting (Towbin et at., *Proc. Nat. Acad. Sci.* 76:4350 (1979)), wherein a suitably treated sample is run on an SDS-PAGE gel before being transferred to a solid support, such as a nitrocellulose filter. Anti-receptor antibodies (unlabelled) are then brought into contact with the support and assayed by a secondary immunological reagent, such as labeled protein A or anti-immunoglobulin (suitable labels including $^{125}$I, horseradish peroxidase and alkaline phosphatase).

Samples for diagnostic purposes may be obtained from any number of sources. A sample obtained direct from the tumor, such as the stroma or cytosol, may be used to determine the metastatic potential of the tumor. It may also be appropriate to obtain the sample from other biological specimens, such as blood or urine. Such diagnosis may be of particular importance in monitoring progress of a patient, such as after surgery to remove a tumor. If a reference reading is taken after the operation, then another taken at regular intervals, any rise could be indicative of a relapse, or possibly a metastasis. Preferably, the sample is from the tumor itself.

The antibodies may be raised against either a peptide of the receptor or the whole molecule. Such a peptide may be presented together with a carrier protein, such as an KLH, to an animal system or, if it is long enough, say 25 amino acid residues, without a carrier.

Polyclonal antibodies generated by the above technique may be used direct, or suitable antibody producing cells may be isolated from the animal and used to form a hybridoma by known means (Kohler and Milstein, *Nature* 256:795. (1975)). Selection of an appropriate hybridoma will also be apparent to those skilled in the art, and the resulting antibody may be used in a suitable assay to identify VEGF$_{165}$R/NP-1 or NP-2.

This invention provides a convenient kit for measuring human VEGF$_{165}$R/NP-1 or NP-2 and their homologs. This kit includes antibodies or antibody fragments which selectively bind human VEGF$_{165}$R/NP-1 or a set of DNA oligonucleotide primers that allow synthesis of cDNA encoding the receptors. Preferably, the primers comprise at least 17 nucleotides and hybridizes under stringent conditions to a DNA fragment having the nucleotide sequence set forth in SEQ ID NO:1 (VEGF$_{165}$R/NP-1) or SEQ ID NO:3 (NP-2). As herein used, the term "stringent conditions" means hybridization will occur only if there is at least 95% and preferably at least 97% identity between the sequences.

DNA encoding human VEGF$_{165}$R/NP-1 or NP-2 and recombinant human VEGF$_{165}$R/NP-1 or NP-2 may be produced according to the methods set forth in the Examples.

The receptors are preferably produced by recombinant methods. A wide variety of molecular and biochemical methods are available for generating and expressing the polypeptides of the present invention; see e.g. the procedures disclosed in *Molecular Cloning, A Laboratory Manual* (2nd Ed.. Sambrook, Fritsch and Maniatis, Cold Spring Harbor), *Current Protocols in Molecular Biology* (Eds. Aufubel, Brent, Kingston, More, Feldman, Smith and Stuhl, Greene Publ. Assoc., Wiley-Interscience, NY, N.Y. 1992) or other procedures that are otherwise known in the art. For example, the polypeptides of the invention may be obtained by chemical synthesis, expression in bacteria such as *E. coli* and eukaryotes such as yeast, baculovirus, or mammalian cell-based expression systems, etc., depending on the size, nature and quantity of the polypeptide.

The term "isolated" means that the polypeptide is removed from its original environment (e.g., the native VEGF molecule). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

Where it is desired to express the receptor or a fragment thereof, any suitable system can be used. The general nature of suitable vectors, expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (*Proc. Natl. Acad. Sci. USA* 74:5463–7 (1977)).

A DNA fragment encoding the receptor or fragment thereof, may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired polypeptide or protein may be expressed. The extent of expression may be analyzed by SDS polyacrylamide gel electrophoresis-SDS-PAGE (Lemelli, *Nature* 227:680–685 (1970)).

Suitable methods for growing and transforming cultures etc. are usefully illustrated in, for example, Maniatis (Molecular Cloning, A Laboratory Notebook, Maniatis et al. (eds.), Cold Spring Harbor Labs. N.Y. (1989)).

Cultures useful for production of polypeptides or proteins may suitably be cultures of any living cells, and may vary from prokaryotic expression systems up to eukaryotic expression systems. One preferred prokaryotic system is that of *E. coli*, owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line and the baculovirus system.

Other expression systems which may be employed include streptomycetes, for example, and yeasts, such as Saccharomyces spp., especially *S. cerevisiae*. Any system may be used as desired, generally depending on what is required by the operator. Suitable systems may also be used to amplify the genetic material, but it is generally convenient to use *E. coli* for this purpose when only proliferation of the DNA is required.

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Additionally, the DNA encoding $VEGF_{165}R/NP-1$ or NP-2 can be used to treat ischemia, e.g., heart and limb. The DNA can be used as an adjunct to gene therapy with VEGF (See, e.g., Isner, J., WO 97/14307). For example, the DNA can be delivered to the vicinity of the area to be treated either prior to, or along with, the VEGF or DNA encoding the VEGF.

The present invention also provides binding assays using $VEGF_{165}R/NP-1$ or NP-2 that permit the ready screening for compounds which affect the binding of the receptor and its ligands. e.g., $VEGF_{165}$. These assays can be used to identify compounds that modulate, preferably inhibit metastasis. However, it is also important to know if a compound enhances metastasis so that its use can be avoided. For example, in a direct binding assay the compound of interest can be added before or after the addition of the labeled ligand, e.g., $VEGF_{165}$ and the effect of the compound on binding or metastasis can be determined by comparing the degree of binding in that situation against a base line standard with that ligand, not in the presence, of the compound. The assay can be adapted depending upon precisely what is being tested.

The preferred technique for identifying molecules which bind to the $VEGF_{165}R/NP-1$ receptor utilizes a receptor attached to a solid phase, such as the well of an assay plate. The binding of the candidate molecules, which are optionally labeled (e.g., radiolabeled), to the immobilized receptor can be measured. Alternatively, competition for binding of a known, labeled receptor ligand, such as $I^{-125}$ $VEGF_{165}$, can be measured. For screening for antagonists, the $VEGF_{165}R/NP-1$ receptor can be exposed to a receptor ligand, e.g., $VEGF_{165}$ followed by the putative antagonist, or the ligand and antagonist can be added to the $VEGF_{165}R/NP-1$ receptor simultaneously, and the ability of the antagonist to block receptor activation can be evaluated. For example, VEGF antagonist activity may also be determined by inhibition of binding of labeled $VEGF_{165}$ to $VEGF_{165}R$ as disclosed in the Examples.

The ability of discovered antagonists to influence angiogenesis or metastasis can also be determined using a number of know in vivo and in vitro assays. Such assays are disclosed in Jain et al., *Nature Medicine* 3, 1203–1208 (1997), and the examples.

The present invention further provides use of the $VEGF_{165}R/NP-1$ for intracellular or extracellular targets to affect binding. Intracellular targeting can be accomplished through the use of intracellularly expressed antibodies referred to as intrabodies. Extracellular targeting can be accomplished through the use of receptor specific antibodies. Additionally, the soluble form of the receptor can be used as a receptor decoy to inhibit binding.

These methods can be used to inhibit metastasis in malignant cells as we have found that the presence of these receptors is positively correlated with metastasis. One can treat a range of afflictions or diseases associated with expression of the receptor by directly blocking the receptor. This can be accomplished by a range of different approaches. For example, antibodies, decoys, small molecules, antagonists, etc. One preferred approach is the use of antibodies that specifically block VEGF binding to the receptor. For example, an antibody to the VEGF binding site. Antibodies to these receptors can be prepared by standard means. For example, one can use single chain antibodies to target these-binding sites.

One type of decoy can be obtained by deleting or otherwise changing the transmembrane portion of the molecule. The cytoplasmic tail can also be deleted in one embodiment, or retained in another.

In accordance with yet another aspect of the present invention, there are provided isolated antibodies or antibody fragments which selectively binds the receptor. The antibody fragments include, for example, Fab, Fab', F(ab')2 or Fv fragments. The antibody may be a single chain antibody, a humanized antibody or a chimeric antibody.

Antibodies, or their equivalents, or other receptor antagonists may also be used in accordance with the present invention for the treatment or prophylaxis of cancers. Administration of a suitable dose of the antibody or the antagonist may serve to block the receptor and this may provide a crucial time window in which to treat the malignant growth.

Prophylaxis may be appropriate even at very early stages of the disease, as it is not known what specific event actually triggers metastasis in any given case. Thus, administration of the antibodies, their equivalents, intrabodies, decoys or antagonists which interfere with receptor activity, may be effected as soon as cancer is diagnosed, and treatment continued for as long as is necessary, preferably until the threat of the disease has been removed. Such treatment may also be used prophylactically in individuals at high risk for development of certain cancers, e.g., prostate or breast.

A method of treatment involves attachment of a suitable toxin to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')2 and Fv; idiotopes; or the results of allotope grafting (where the recognition region of an animal antibody is grafted into the appropriate region of a human antibody to avoid an immune response in the patient), for example. Single chain antibodies may also be used. Other suitable modifications and/or agents will be apparent to those skilled in the art.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81,6851 (1985); Takeda, et al., Nature 314,452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad Sci. U.S.A., 80, 7308–7312 (1983); Kozbor et al., Immunology Today, 4, 7279 (1983); Olsson et al., Meth. Enzymol., 92, 3–16 (1982)), and are preferably made according to the teachings of PCT Publication WO 92/06193 or EP 0239400. Humanized antibodies can be commercially produced by, for example, Scotgen Limited, 2 Holly Road, Twickenham, Middlesex, Great Britain.

The antibody can be administered by a number of methods. One preferred method is set forth by Marasco and Haseltine in PCT WO 94/02610, which is incorporated herein by reference. This method discloses the intracellular delivery of a gene encoding the antibody. One would preferably use a gene encoding a single chain antibody. The antibody would preferably contain a nuclear localization sequence. One preferably uses an SV40 nuclear localization signal. By this method one can intracellularly express an antibody, which can block $VEGF_{165}R$/NP-1 or NP-2 functioning in desired cells.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are one preferred mode of administration.

$VEGF_{165}R$/NP-1 expression may also be inhibited in vivo by the use of antisense technology. Antisense technology can be used to control gene expression through triple-helix formation or antisense DNA or RNA, both of which methods are based on binding of a polynucleotide to DNA or RNA. An antisense nucleic acid molecule which is complementary to a nucleic acid molecule encoding receptor can be designed based upon the isolated nucleic acid molecules encoding the receptor provided by the invention. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO:1 ($VEGF_{165}R$/NP-1) or SEQ ID NO:3/NP-2). A nucleic acid is designed which has a sequence complementary to a sequence of the coding or untranslated region of the shown nucleic acid. Alternatively, an antisense nucleic acid can be designed based upon sequences of a $VEGF_{165}R$ gene, which can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1) 1986.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antibodies or nucleic acids of the invention are administered orally, topically, or by parenteral means, including subcutaneous and intramuscular injection, implantation of sustained release depots, intravenous injection, intranasal administration, and the like. Accordingly, antibodies or nucleic acids of the invention may be administered as a pharmaceutical composition comprising the antibody or nucleic acid of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered TM, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene Registered TM (Marion), Aquaphor Registered TM (Duke Laboratories), and the like. Other topical formulations include aerosols, bandages, and other wound dressings. Alternatively one may incorporate or encapsulate the compounds such as a VEGF antagonist in a suitable polymer matrix or membrane, thus providing a sustained-release delivery device suitable for implantation near the site to be treated locally. Other devices include indwelling catheters and devices such as the Alzet Registered TM minipump. Ophthalmic preparations may be formulated using commercially available vehicles such as Sorbi-care Registered TM (Allergan), Neodecadron Registered TM (Merck, Sharp & Dohme), Lacrilube Registered TM, and the like, or may employ topical preparations such as that described in U.S. Pat. No. 5,124,155, incorporated herein by reference. Further, one may provide a VEGF antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of antibody or nucleic acid required to treat any particular disorder will of course vary depending upon the nature and severity of the disorder, the age and condition of the subject, and other factors readily determined by one of ordinary skill in the art.

All references cited above or below are herein incorporated by reference.

The present invention is further illustrated by the following Examples. These Examples are provided to aid in the understanding of the invention and are not construed as a limitation thereof.

EXAMPLE 1

Experimental procedures

Materials

Cell culture media, lipofectin and lipofectamin reagents for transfection were purchased from Life Technologies. Human recombinant $VEGF_{165}$ and $VEGF_{121}$ were produced in Sf-21 insect cells infected with recombinant baculovirus vectors encoding either human $VEGF_{165}$ or $VEGF_{121}$ as previously described (Cohen et al., Growth Factors, 7, 131–138 (1992); Cohen et al., J. Biol. Chem., 270, 11322–11326 (1995)). GST VEGF exons 7+8 fusion protein was prepared in E. Coli and purified as previously described (Soker et al., J. Biol. Chem., 271, 5761–5767 (1996)). Heparin, hygromycin B and protease inhibitors were purchased from Sigma (St. Louis, Mo.).

$^{125}$I-sodium $^{32}$P-dCTP, and GeneScreen-Plus Registered Trademark hybridization transfer membrane were purchased from DuPont NEN (Boston, Mass.). Disuccinimidyl suberate (DSS)and IODO-BEADS Registered Trademark were purchased from Pierce Chemical Co. (Rockford, Ill.). Con A Sepharose Registered Trademark was purchased from Pharmacia LKB Biotechnology Inc. (Piscataway, N.J.). InRNAzol-B Registered Trademark was purchased from TEL-TEST Inc. (Friendswood, Tex.). Silver Stain Registered Trademark kit and Trans-Blot Registered Trademark PVDF membranes were purchased from Bio-Rad Laboratories (Hercules, Calif.). Multiple tissue northern blot membranes were purchased from Clontech (Palo Alto, Calif.). PolyATract Registered Trademark mRNA isolation kits were purchased from Promega (Madison, Wisc.). RediPrime Registered Trademark DNA labeling kits and molecular weight markers were purchased from Amersham (Arlington Heights, Ill.). Plasmids: pcDNA3.1 was purchased from Invitrogen (Carlsbad, Calif.), and pCPhygro Registered Trademark, containing the CMV promoter and encoding hygromycin B phosphorylase, was kindly provided by Dr. Urban Deutsch (Max Plank Institute, Bad Nauheim, Germany). Restriction endonucleases and Ligase Registered Trademark were purchased from New England Biolabs, Inc (Beverly, Mass.). NT-132 Registered Trademark photographic emulsion and x-ray film were purchased from the Eastman Kodak company (Rochester N.Y.).

Cell culture

Human umbilical vein EC (HUVEC) were obtained from American Type Culture Collection (ATCC) (Rockville, Md.), and grown on gelatin coated dishes in M-199 medium containing 20% fetal calf serum (FCS) and a mixture of glutamine, penicillin and streptomycin (GPS). Basic FGF (2 ng/ml) was added to the culture medium every other day. Parental porcine aortic endothelial (PAE) cells and PAE cells expressing KDR (PAE/KDR) (Waltenberger et al., J. Biol. Chem. 269, 26988–26995 (1994)) were kindly provided by Dr. Lena Claesson-Welsh and were grown in F12 medium containing 10% FCS and GPS. MDA-MB-231 cells and MDA-MB-453 cells were obtained from ATCC, and grown in DMEM containing 10% FCS and GPS. The human melanoma cell lines, RU-mel, EP-mel and WK-mel were kindly provided by Dr. Randolf Byer (Boston University Medical School, Boston, Mass.), and grown in DMEM containing 2% FCS, 8% calf serum and GPS. Human metastatic prostate adenocarcinoma, LNCaP and prostate carcinoma, PC3 cells were kindly provided by Dr. Michael Freeman (Children's Hospital, Boston, Mass.), and grown in RPMI 1640 containing 5% FCS and GPS.

Purification and protein sequencing

Approximately $5 \times 10^8$ MDA-MB-231 cells grown in 150 cm dishes were washed with PBS containing 5 mM EDTA, scraped and centrifuged for 5 min at 500 g. The cell pellet was lysed with 150 ml of 20 mM HEPES, pH 8.0, 0.5% triton X-100 and protease inhibitors including 1 mM AEBSF, 5 µg/ml leupeptin and 5 µg/ml aprotinin for 30 min on ice, and the lysate was centrifuged at 30,000 x g for 30 min. $MnCl_2$ and $CaCl_2$ were added to the supernatant to obtain a final concentration of 1 mM each. The lysate was absorbed onto a Con A Sepharose column (7 ml) and bound proteins were eluted with 15 ml 20 mM HEPES, pH 8.0, 0.2M NaCl, 0.1% triton X-100 and 1M methyl-α-D-mannopyranoside at 0.2 ml/min. The elution was repeated twice more at 30 minute intervals. The Con A column eluates were pooled and incubated for 12 h at 4° C. with 0.5 ml of $VEGF_{165}$-Sepharose beads, containing about 150 µg $VEGF_{165}$, prepared as described previously (Wilchek and Miron, Biochem. Int. 4, 629–635 (1982)). The $VEGF_{165}$-Sepharose beads were washed with 50 ml of 20 mM HEPES, pH 8.0, 0.2M NaCl and 0.1% triton X-100 and then with 25 ml of 20 mM HEPES, pH 8.0. The beads were boiled in SDS-PAGE buffer and bound proteins were separated by 6% SDS-PAGE. Proteins were transferred to a TransBlot PVDF membrane using a semi-dry electric blotter (Hoeffer Scientific), and the PVDF membrane was stained with 0.1% Coomassie Brilliant Blue in 40% methanol. The two prominent proteins in a 130–140 kDa doublet were cut out separately and N-terminally sequenced using an Applied Biosystems model 477A microsequenator as a service provided by Dr. William Lane of the Harvard Microchemistry facility (Cambridge, Mass.).

Expression cloning and DNA sequencing

Complementary DNA (cDNA) was synthesized from 5 μg 231 mRNA. Double-stranded cDNA was ligated to EcoRI adaptors, and size-fractionated on a 5–20% potassium acetate gradient. DNA fragments larger than 2 kb were ligated to an eukaryotic expression plasmid, pcDNA3.1. The plasmid library was transfected into E.coli to yield a primary library of approximately $1 \times 10^7$ individual clones. A portion of the transformed bacteria was divided into 240 pools, each representing approximately $3 \times 10^3$ individual clones. DNA prepared from each pool was used to transfect COS-7 cells seeded in 12 well dishes, using the LIPOFECTIN reagent according to the manufacturer's instructions. Three days after transfection, the cells were incubated on ice for 2 h with $^{125}$I-VEGF$_{165}$ (10 ng/ml) in the presence of 1 μg/ml heparin, washed and fixed with 4% paraformaldehyde in PBS. $^{125}$I-VEGF$_{165}$ binding to individual cells was detected by overlaying the monolayers with photographic emulsion, NT-B2, and developing the emulsion after two days as described (Gearing et al., 1989). Seven positive DNA pools were identified and DNA from one of the positive pools was used to transform E. Coli. The E. coli were sub-divided into 50 separate pools and plated onto 50 LB ampicillin dishes, with each pool representing approximately 100 clones. DNA made from these pools was transfected into COS-7 cells which were screened for $^{125}$I-VEGF$_{165}$ binding as described above. Twenty positive pools were detected at this step, and their corresponding DNAs were used to transform E. Coli. Each pool was plated onto separate LB ampicillin dishes and DNA was prepared from 96 individual colonies and screened in a 96-well two dimensional grid for $^{125}$I-VEGF$_{165}$ binding to tranfected COS-7 cells as described above. Seven single clones were identified as being positive at this step. The seven positive plasmid clones were amplified and their DNA was analyzed by restriction enzyme digestion. Six clones showed an identical digestion pattern of digest and one was different. One clone from each group was submitted for automated DNA sequencing.

Northern Analysis

Total RNA was prepared from cells in culture using RNAzol according to the manufacturer's instructions. Samples of 20 μg RNA were separated on a 1% formaldehyde-agarose gel, and transferred to a GENE-SCREEN PLUS membrane. The membrane was hybridized with a $^{32}$P labeled fragment of human VEGF$_{165}$R/NP-1 cDNA, corresponding to nucleotides 63–454 in the ORF, at 63° C. for 18 h. The membrane was washed and exposed to an x-ray film for 18 h. A commercially-obtained multiple human adult tissue mRNA blot (Clentech 2 μg/lane) was probed for human NP-1 in a similar manner. The multiple tissue blot was stripped by boiling in the presence of 0.5% SDS and re-probed with a $^{32}$P labeled fragment of KDR cDNA corresponding to nucleotides 2841–3251 of the ORF (Terman et al., Oncogene 6, 1677–1683 (1991)).

Transfection of PAE cells

Parental PAE cells and PAE cells expressing KDR (PAE/KDR) (Waltenberger et al., 1994) were obtained from Dr. Lena Claesson-Welsh. Human NP-1 cDNA was digested with XhoI and XbaI restriction enzymes and subcloned into the corresponding sites of pCPhygro, to yield pCPhyg-NP-1. PAE and PAE/KDR cells were grown in 6 cm dishes and transfected with 5 μg of pCPhyg-NP-1 using LIPOFECTIN, according to the manufacturer's instructions. Cells were allowed to grow for an additional 48 h and the medium was replaced with fresh medium containing 200 μg/ml hygromycin B. After 2 weeks, isolated colonies (5–10×10$^3$ cell/colony) were transferred to separate wells of a 48 well dish and grown in the presence of 200 μg /ml hygromycin B. Stable PAE cell clones expressing VEGF$_{165}$R/NP-1 (PAE,/NP-1) or co-expressing VEGF$_{165}$R/NP-1 and KDR (PAE/KDR/NP-1) were screened for VEGF$_{165}$ receptor expression by binding and cross linking of $^{125}$-VEGF$_{165}$. For transient transfection, PAE/KDR cells were transfected with VEGF$_{165}$R/NP-1 as described above and after three days $^{125}$I-VEGF$_{165}$ cross-linking analysis was carried out.

Radio-iodination of VEGF, binding and cross-linking experiments.

The radio-iodination of VEGF$_{165}$ and VEGF$_{121}$ using IODO-BEADS was carried out as previously described (Soker et al., J. Biol. Chem. 272, 31582–31588 (1997)). The specific activity ranged from 40,000–100,000 cpm/ng protein. Binding and cross-linking experiments using $^{125}$-I-VEGF$_{165}$ and $^{125}$I-VEGF$_{121}$ were performed as previously described (Gitay-Goren et al., J. Biol. Chem. 267, 6093–6098 (1992); Soker et al., J. Biol. Chem. 271, 5761–5767 (1996)). VEGF binding was quantitated by measuring the cell-associated radioactivity in a γ-counter (Beckman, Gamma 5500). The counts represent the average of three wells. All experiments were repeated at least three times and similar results were obtained. The results of the binding experiments were analyzed by the method of Scatchard using the LIGAND program (Munson and Rodbard, 1980). $^{125}$I-VEGF$_{165}$ and $^{125}$I-VEGF$_{121}$ cross linked complexes were resolved by 6% SDS/PAGE and the gels were exposed to an X-Ray film. X-ray films were subsequently scanned by using an IS-1000 digital imaging system (Alpha Innotech Corporation)

Purification of VEGF$_{165}$R

Figure 1:
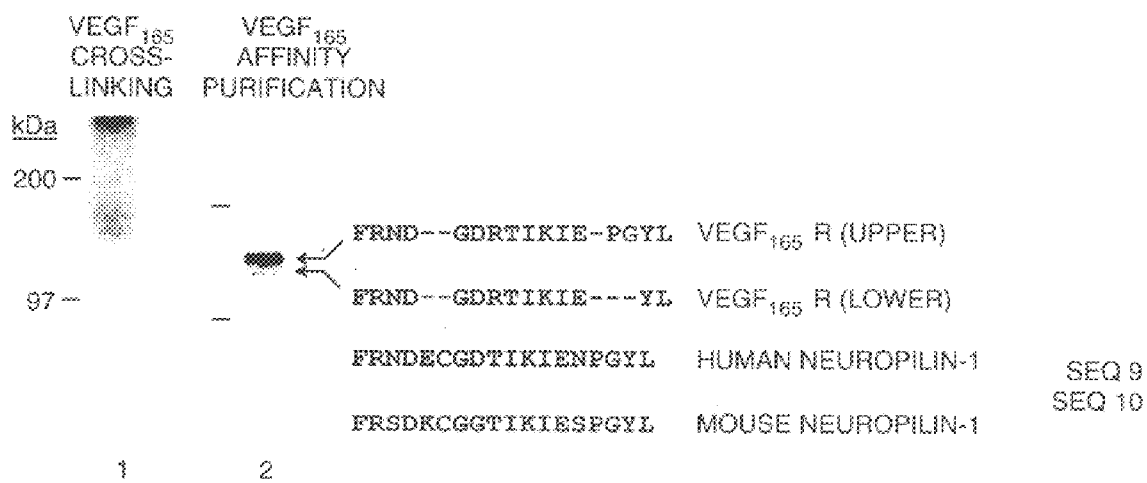
FIG. 1 shows purification of $VEGF_{165}R$ From 231 Cells. $^{125}I$-$VEGF_{165}$ (5 ng/ml) was bound and cross-linked to receptors on 231 cells and analyzed by SDS PAGE and autoradiography (lane 1). $VEGF_{165}R$ was purified by Con A and $VEGF_{165}$ affinity column chromatography and analyzed by SDS-PAGE and silver stain (lane 2). Two prominent bands were detected (arrows) and N-terminally sequenced separately. Their N-terminal 18 amino acid sequences are shown to the right of the arrows. The published N-terminal sequences of human and mouse neuropilin (Kawakami et al., *J. Neurobiol.*, 29, 1–17 (1995); He and Tessier-Lavigne, *Cell* 90, 739–751 1997) are shown below (SEQ ID NOS: 5 and 6).
Figure 9:
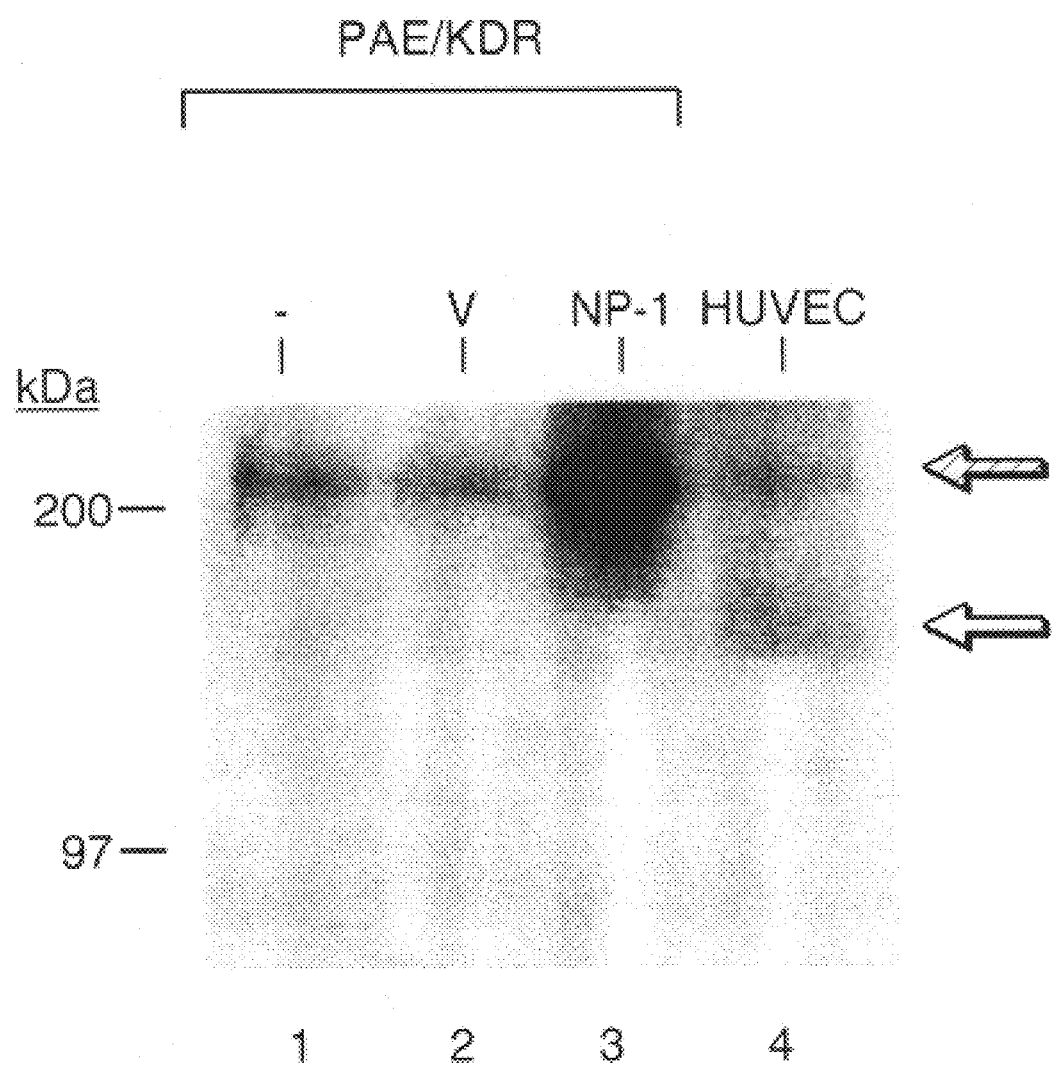
FIG. 9 shows cross linking of VEGF$_{165}$ to PAE/KDR Cells Co-expressing VEGF$_{165}$R/NP-1 Transiently. PAE/KDR cells were transfected with pCPhygro or pCPhyg-NP-1 plasmids as described in "Experimental Procedures", and grown for 3 days in 6 cm dishes. $^{125}$I-VEGF$_{165}$ (5 ng/ml) was bound and cross linked to parental PAE/KDR cells (lane 1), to PAE/KDR cells transfected with pCPhygro vector control (V) (lane 2), to PAE/KDR cells transfected with pCPhyg-VEGF$_{165}$R/NP-1 plasmids (VEGF$_{165}$R/NP-1) (lane 3), and to HUVEC (lane 4).). The binding was carried out in the presence of 1 μg/ml heparin. The cells were lysed and proteins were resolved by 6% SDS-PAGE as in FIG. 8. Solid arrows denote radiolabeled complexes containing $^{125}$I-VEGF$_{165}$ and KDR. Open arrows denote radiolabeled complexes containing $^{125}$I-VEGF$_{165}$ and VEGF$_{165}$R/PN-1.

Cross-linking of $^{125}$I-VEGF$_{165}$ to cell surface receptors of 231 cells results in formation of a 165–175 kDa labeled complex (Soker et al., J. Biol. Chem. 271, 5761–5767 (1996)). These cells have about $1-2 \times 10^5$ VEGF$_{165}$ binding sites/cell. In contrast to VEGF$_{165}$, VEGF$_{121}$ does not bind to the 231 cells and does not form a ligand-receptor complex (Soker et al., J. Biol. Chem. 271, 5761–5767 (1996)). The relatively high VEGF$_{165}$R number and the lack of any detectable KDR or Flt-1 mRNA in 231 cells (not shown) suggested that these cells would be a useful source for VEGF$_{165}$R purification. Preliminary characterization indicated that VEGF$_{165}$R is a glycoprotein and accordingly, a 231 cell lysate prepared from approximately $5 \times 10^8$ cells was absorbed onto a Con A Sepharose column. Bound proteins, eluted from the Con A column, were incubated with VEGF$_{165}$-Sepharose and the VEGF$_{165}$ affinity purified proteins were analyzed by SDS-PAGE and silver staining (FIG. 9, lane 2). A prominent doublet with a molecular mass of about 130–135 kDa was detected. This size is consistent with the formation of a 165-175 kDa complex of 40–45 kDa VEGF$_{165}$ bound to receptors approximately 130–135 kDa in size (FIG. 9, lane 1). The two bands were excised separately and N-terminal amino acid sequencing was carried out (FIG. 1, right). Both the upper and lower bands had similar N-terminal amino acid sequences which showed high degrees of sequence homology to the predicted amino acid sequences in the N-terminal regions of mouse (Kawakami et al., J. Neurobiol, 29, 1–17 (1995)) and human neuroplilin-1 (NP-1) (He and Tessier-Lavigne, Cell 90739–751 (1997)).

Figure 2A:
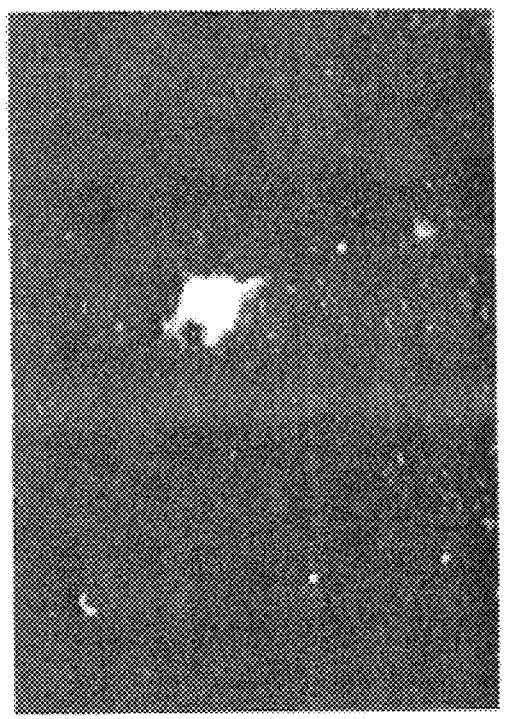
FIGS. 2A and 2B show isolation of $VEGF_{165}R$ cDNA by Expression Cloning. Photomicrographs (dark field illumination) of COS 7 cells binding $^{125}$-I-$VEGF_{165}$. $^{125}I$-$VEGF_{165}$ was bound to transfected COS 7 cells which were then washed, fixed, and overlayed with photographic emulsion that was developed as described in the example, infra.
Figure 2B:
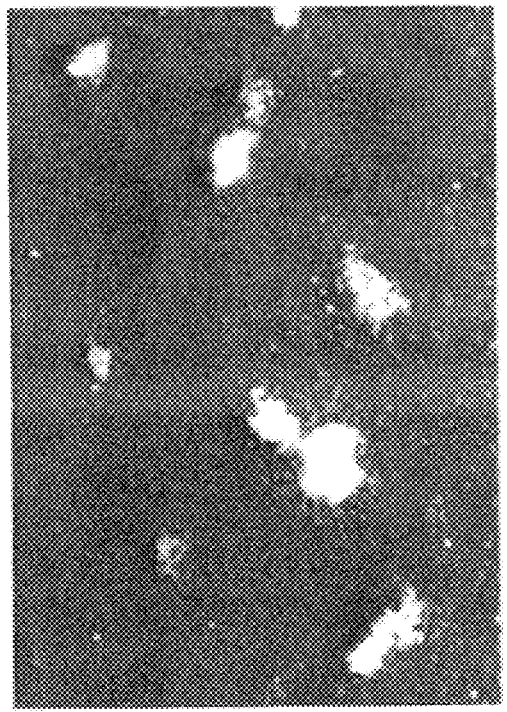

Expression cloning of VEGF$_{165}$R from 231 cell-derived mRNA Concomitant with the purification, VEGF$_{165}$R was cloned by expression cloning (Aruffo and Seed, *Proc. Natl. Acad. Sci. USA* 84, 8573–8577 (1987a); Aruffo and Seed, *EMBO J.* 6, 3313–3316 (1987b); Gearing et al., *EMBO J.* 8,3667–3676 (1989)). For expression cloning, 231 cell mRNA was used to prepare a cDNA library of approximately $10^7$ clones in a eukaryotic expression plasmid. *E. coli* transformed with the plasmid library were divided into pools. The DNA prepared from each pool were transfected into COS-7 cells in separate wells and individual cells were screened for the ability to bind $^{125}$-VEGF$_{165}$ as detected by autoradiography of monolayers overlayed with photographic emulsion (FIG. 2A). After three rounds of subpooling and screening, seven single positive cDNA clones were obtained. FIG. 2B shows binding of 125I-VEGF$_{165}$ to COS-7 cells transfected with one of these single positive clones (clone A2).

Restriction enzyme analysis revealed that six of the seven positive single clones had identical restriction digestion patterns but that one clone had a pattern that was different (not shown). Sequencing of one of these similar cDNA clones, clone A2 (FIG. 3), showed it to be identical to a sequence derived from a human-expressed sequence tag data bank (dbEST). This sequence also showed a high percentage of homology to the sequence of mouse neuropilin, NP-1 (Kawakami et al., *J. Neurobiol* 29, 1–17 (1995)). After we had cloned human VEGF$_{165}$R, two groups reported the cloning of rat and human receptors for semaphorin III and identified them to be NP-1 (He and Tessier-Lavigne, *Cell* 90, 739–751 (1997); Kolodkin et al., *Cell* 90, 753–762 (1997)). The 231 cell-derived VEGF$_{165}$R cDNA sequence is virtually identical (see figure legend 3 for exceptions) to the human NP-1 sequence (He and Tessier-Lavigne, *Cell* 90, 739–751 (1997)). Significantly, the predicted amino acid sequence obtained by expression cloning (FIG. 3) confirmed the identification of VEGF$_{165}$R as NP-1 that was determined by N-terminal sequencing (FIG. 1), and we have therefore named this VEGF receptor, VEGF$_{165}$R/NP-1.

The human VEGF$_{165}$R/NP-1 cDNA sequence predicts an open reading frame (ORF) of 923 amino acids with two hydrophobic regions representing putative signal peptide and transmembrane domains (FIG. 3). Overall, the sequence predicts ectodomain, transmembrane and cytoplasmic domains consistent with the structure of a cell surface receptor. The N-terminal sequence obtained via protein purification as shown in FIG. 1 is downstream of a 21 amino acid putative hydrophobic signal peptide domain, thereby indicating directly where the signal peptide domain is cleaved and removed. The short cytoplasmic tail of 40 amino acids is consistent with results demonstrating that soluble VEGF$_{165}$R/NP-1 released by partial trypsin digestion of 231 cells is similar in size to intact VEGF$_{165}$R/NP-1 (not shown).

Sequence analysis of the one clone obtained by expression cloning that had a different restriction enzyme profile predicted an open reading frame of 931 amino acids with about a 47% homology to VEGF$_{165}$R/NP-1 (FIGS. 4A and 4B). This human cDNA has a 93% sequence homology with rat neuropilin-2 (NP-2) and is identical to the recently cloned human NP-2 (Chen et al., *Neuron*, 19, 547–559 (1997)).

Expression of VEGF$_{165}$R/NP-1 in adult cell lines and tissues

Figure 5:
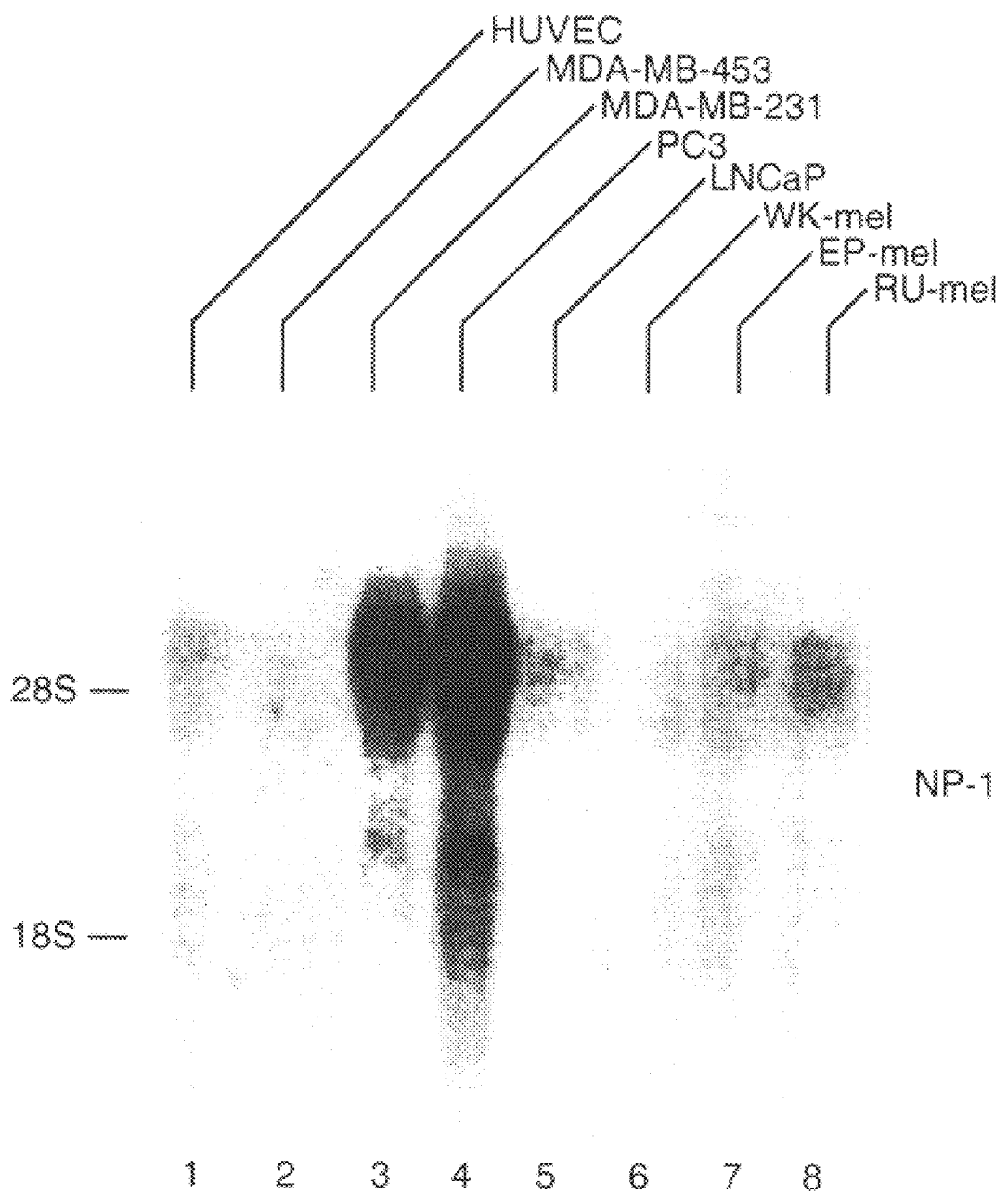
FIG. 5 shows a Northern Blot Analysis of VEGF$_{165}$R/NP-1 Expression in Human EC and Tumor-Derived Cell Lines. Total RNA samples prepared from HUVEC (lane 1) and tumor-derived breast carcinoma, prostate carcinoma and melanoma cell lines as indicated (lanes 2–8) were resolved on a 1% agarose gel and blotted onto a GeneScreen nylon membrane. The membrane was probed with $^{32}$P-labeled VEGF$_{165}$R/NP-1 cDNA and exposed to X-ray film. Equal RNA loading was demonstrated by ethydium bromide staining of the gel prior to blotting. A major species of VEGF$_{165}$R/NP-1 mRNA of approximately 7 kb was detected in several of the cell lines.

Reports of NP-1 gene expression have been limited so far to the nervous system of the developing embryo (Takagi et al., *Dev. Biol.* 122, 90–100 (1987); Kawakami et al., *J. Neurobiol.* 29, 1–17 (1995); Takagi et al., *Dev. Biol.* 170, 207–222 (1995)). Cell surface VEGF$_{165}$R/NP-1, however, is associated with non-neuronal adult cell types such as EC and a variety of tumor-derived cells (Soker et al., *J. Biol. Chem.* 271, 5761–5767 (1996)). Northern blot analysis was carried out to determine whether cells that crossed-linked $^{125}$I-VEGF$_{165}$ also synthesized VEGF$_{165}$P/NP-1 mRNA. (FIG. 5). VEGF$_{165}$R/NP-1 mRNA levels were highest in 231 and PC3 cells. VEGF$_{165}$R/NP-1 mRNA was detected to a lesser degree in HUVEC, LNCaP, EP-mel and RU-mel cells. There was little if any expression in MDA-MB-453 and WK-mel cells. The VEGF$_{165}$R/NP-1 gene expression patterns were consistent with our previous results showing that HUVEC, 231, PC3, LNCaP, EP-mel and RU-mel cells bind $^{125}$I VEGF$_{165}$ to cell surface VEGF$_{165}$R/NP-1 but that MDA-MB453 and WK-mel cells do not (Soker et al., *J. Biol. Chem.* 271, 5761–5767 (1996)).

Figure 6:
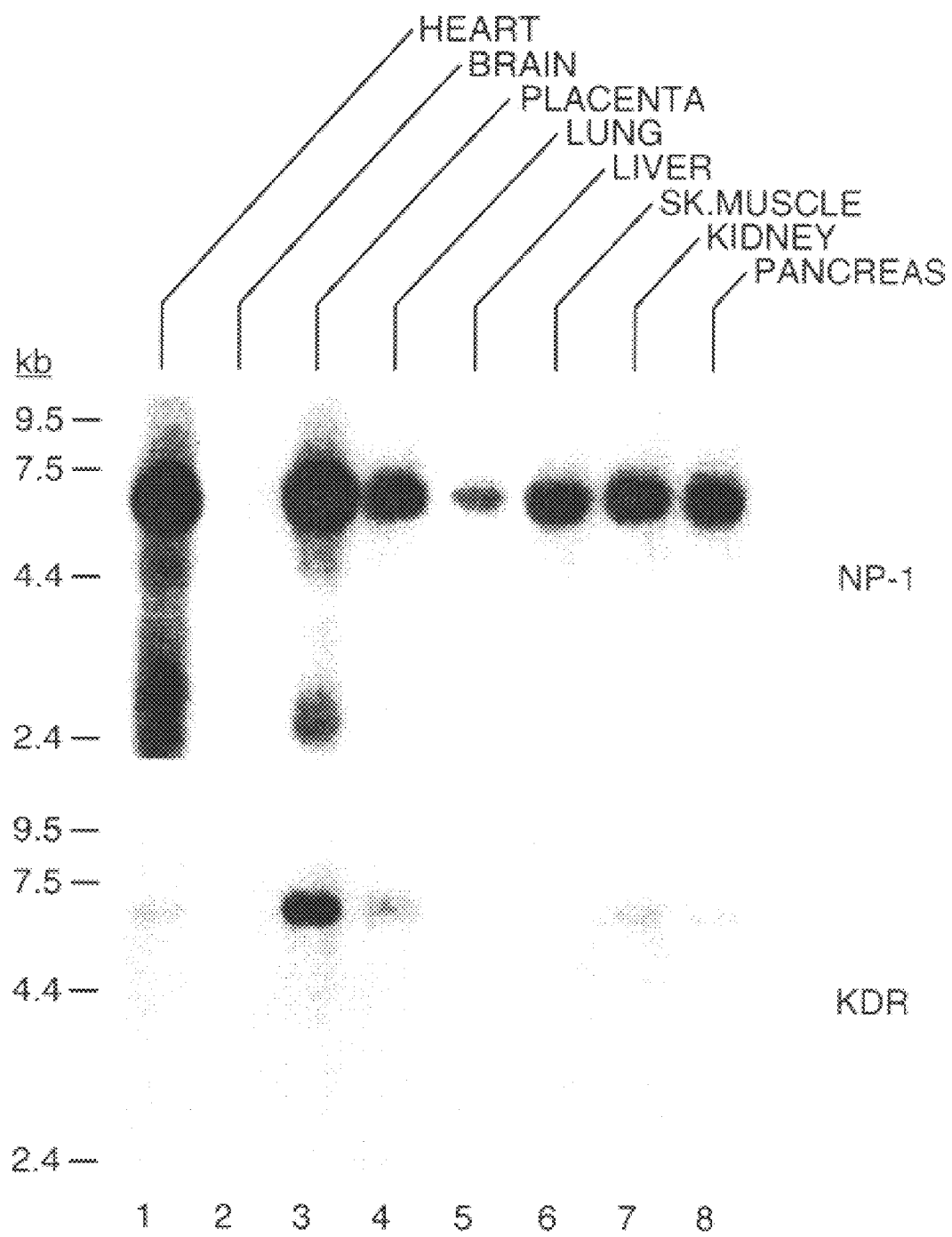
FIG. 6 shows a Northern Blot Analysis of VEGF$_{165}$R/NP-1 and KDR mRNA in Adult Human Tissues. A pre-made Northern blot membrane containing multiple samples of human mRNA (Clonetech) was probed with $^{32}$P-labeled VEGF$_{165}$R/NP-1 cDNA (top) as described in FIG. 5, and then stripped and reprobed with $^{32}$P-labeled KDR cDNA (bottom).

VEGF$_{165}$R/NP-1 gene expression was analyzed also by Northern blot in a variety of adult tissues in comparison to KDR gene expression (FIG. 6). VEGF$_{165}$R/NP-1 mRNA levels were relatively highly in adult heart and placenta and relatively moderate in lung, liver, skeletal muscle, kidney and pancreas. A relatively low level of VEGF$_{165}$R/NP-1 mRNA was detected in adult brain. Interestingly, previous analysis of NP-1 gene expression in mouse and chicken brain suggested that this gene was expressed primarily during embryonic development and was greatly diminished after birth (Kawakami et al., *J. Neurobiol.* 29, 1–17 (1995); Takagi et al., *Dev. Biol.* 170, 207–222 (1995)). The tissue distribution of KDR mRNA was similar to that of VEGF$_{165}$R/RP-1 with the exception that it was not expressed highly in the heart. These results indicate that VEGF$_{165}$R/NP-1 is expressed widely in adult non-neuronal tissue, including tissues in which angiogenesis occurs such as heart and placenta.

Characterization of VEGF$_{165}$ binding to VEGF$_{165}$R/NP-1

Figure 7A:
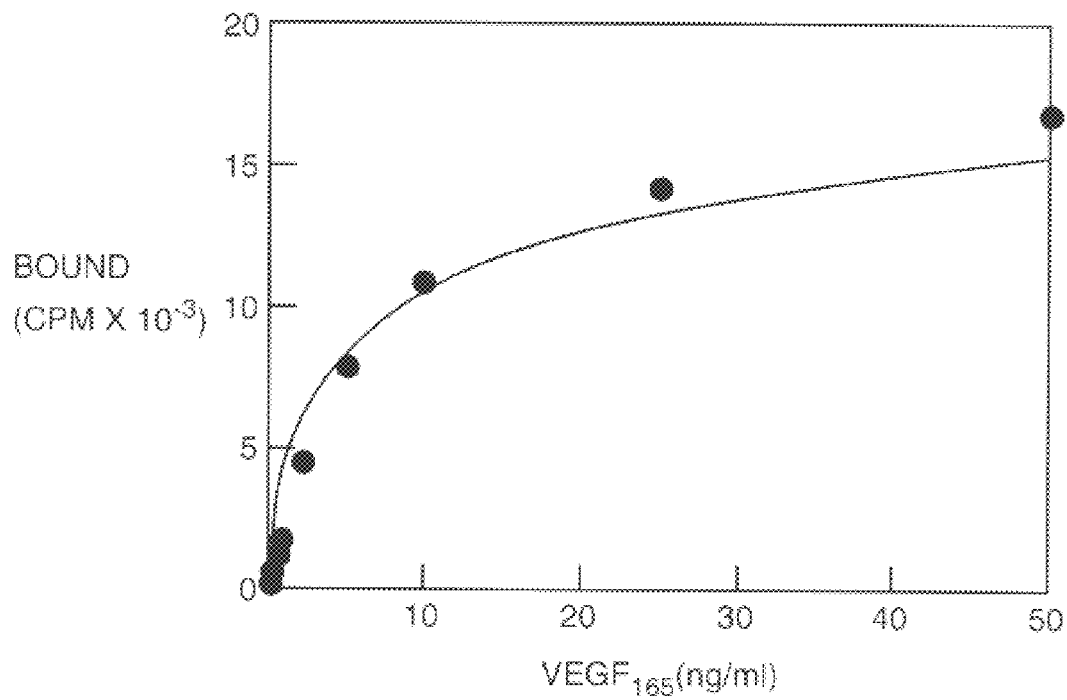
FIGS. 7A and 7B show a Scatchard Analysis of VEGF$_{165}$ binding to VEGF$_{165}$R/NP-1.
Figure 7B:
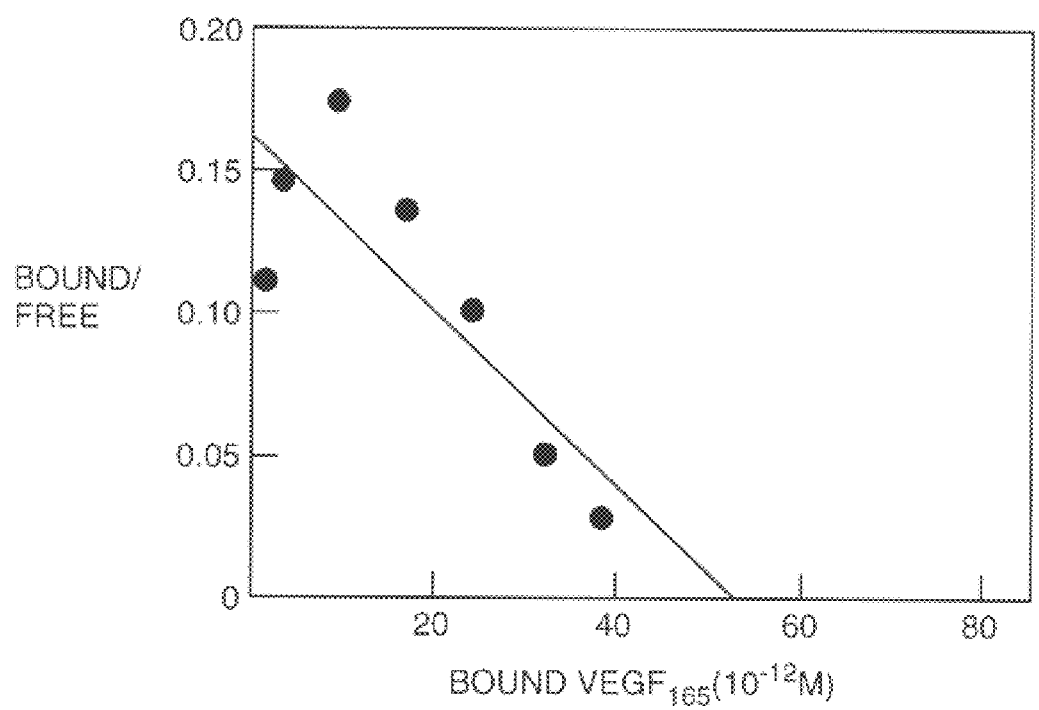

In order to characterize the binding properties of VEGF$_{165}$R/NP-1, porcine aortic endothelial (PAE) cells were transfected with the cDNA of VEGF$_{165}$R/NP-1. The PAE cells were chosen for these expression studies because they express neither KDR, Flt-1 (Waltenberger et al.,*J. Biol. Chem.* 269, 26988–26995 (1994)) nor VEGF$_{165}$R. Stable cell lines synthesizing VEGF$_{165}$R/NP-1 (PAE/NP-1) were established and $^{125}$-VEGF$_{165}$ binding experiments were carried out (FIG. 7). $^{125}$I-VEGF$_{165}$ binding to PAE/NP-1 cells increased in a dose-dependent manner and reached saturation at approximately 30 ng/ml demonstrating that VEGF$_{165}$R/NP-1 is a specific VEGF$_{165}$ receptor (FIG. 7A). Scatchard analysis of VEGF$_{165}$ binding revealed a single class of VEGF$_{165}$ binding sites with a $K_d$ of approximately $3.2 \times 10^{-}$M and approximately $3 \times 10^5$ $^{125}$I-VEGF$_{165}$ binding sites per cell (FIG. 7B). Similar $K_d$ values were obtained for several independently-generated PAE/NP-1 clones, although the receptor number varied from clone to clone (not shown). The $K_d$ of $3 \times 10^{-10}$ M for the PAE/NP-1 cell lines is consistent with the $2$–$2.8 \times 10^{-10}$M $K_d$ values obtained for VEGF$_{165}$R/NP-1 expressed naturally by HUVEC and 231 cells (Gitay-Goren et al., *J. Biol. Chem.* 267, 6093–6098 (1992); Soker et al., *J. Biol. Chem.* 271, 5761–5767 (1996)). The binding of 125I-VEGF$_{165}$ to PAE/NP-1 cells was enhanced by 1 µg/ml heparin (not shown), consistent with previous studies showing that heparin enhances $^{125}$I-VEGF$_{165}$ binding to VEGF$_{165}$R/NP-1 on HUVEC and 231 cells (Gitay-Goren et al., *J. Biol. Chem.* 267, 6093–6098 (1992); Soker et al., *J. Biol. Chem.* 271, 5761–5767 (1996)).

Isoform-specific binding of VEGF to cells expressing VEGF$_{165}$R/NP-1

Figure 8:
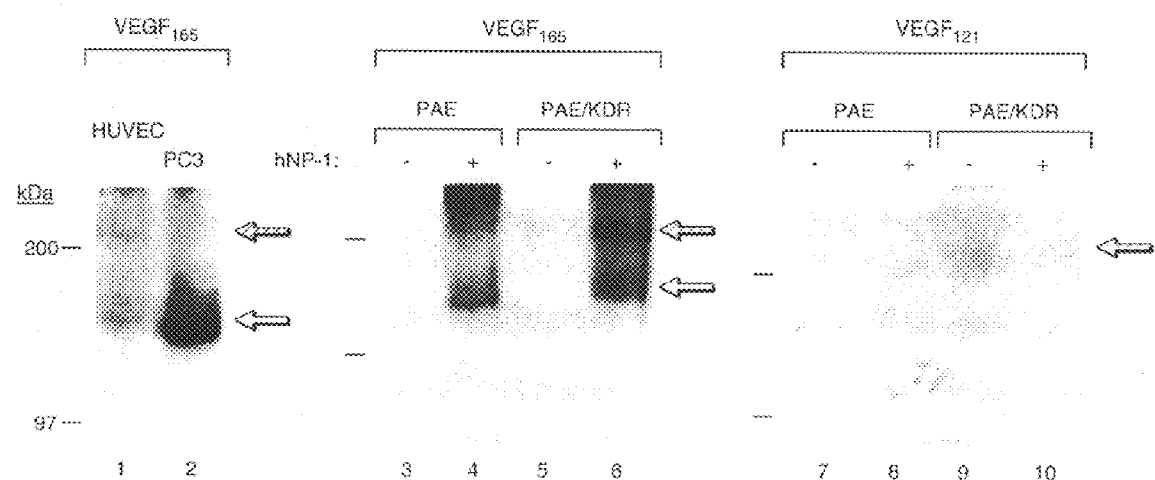
FIG. 8 shows cross-linking of VEGF$_{165}$ and VEGF$_{121}$ to PAE cells Expressing VEGF$_{165}$R/NP-1 and/or KDR. $^{125}$I-VEGF$_{165}$ (5 ng/ml) (lanes 1–6) or $^{125}$-VEGF$_{121}$ (10 ng/ml) (lanes 7–10) were bound to subconfluent cultures of HUVEC (lane 1), PC3 (lane 2), PAE (lanes 3 and 7), a clone of PAE cells transfected with human VEGF$_{165}$R/NP-1 cDNA (PAE/NP-1) (lanes 4 and 8), a clone of PAE cells transfected with KDR (PAE/KDR) (lanes 5 and 9), and a clone of PAE/KDR cells transfected with human VEGF$_{165}$R/NP-1 cDNA (PAE/KDR/NP-1) (lanes 6 and 10). The binding was carried out in the presence of 1 μg/ml heparin. At the end of a 2 hour incubation, each $^{125}$I-VEGF isoform was chemically cross-linked to the cell surface. The cells were lysed and proteins were resolved by 6% SDS-PAGE. The polyacrylamide gel was dried and exposed to X-ray film. Solid arrows denote radiolabeled complexes containing $^{125}$I-VEGF and KDR, open arrows denote radiolabeled complexes containing $^{125}$I-VEGF and VEGF$_{165}$R/NP-1.

VEGF$_{165}$, but not VEGF$_{121}$, binds to VEGF$_{165}$R/NP-1 on HUVEC and 231 cells (Gitay-Goren et al., *J. Biol. Chem.* 271, 5519–5523 (1992); Soker et al., *J. Biol. Chem.* 271, 5761–5767 (1996)). To ascertain whether cells transfected with VEGF$_{165}$R/NP-1 had the same binding specificity. PAE/NP-1 cells were incubated with $^{125}$I-VEGF$_{165}$ or $^{125}$I-VEG$_{121}$ followed by cross-linking (FIG. 8). $^{125}$I-VEGF$_{165}$ did not bind to parental PAE cells (FIG. 8, lane 3) but did bind to PAE/NP-1 cells via VEGF$_{165}$R/NP-1 (FIG. 8, lane 4). The radiolabeled complexes formed with VEGF$_{165}$R/NP-1 were similar in size to those formed in HUVEC (FIG. 8, lane 1) and PC3 cells (FIG. 8, lane 2). On the other hand, $^{125}$I-VEGF$_{121}$, did not bind to either parental PAE (FIG. 8, lane 7) or to PAE/NP-1 cells (FIG. 8, lane 8). These results demonstrate that the VEGF isoform-specific binding that occurs with cells expressing endogenous VEGF$_{165}$R/NP-1 such as HUVEC, 231 and PC3 cells, can be replicated in cells transfected with VEGF$_{165}$R/NP-1 cDNA and support the finding that VEGF$_{165}$R and NP-1 are identical.

Co-expression of VEGF$_{165}$R/NP-1 and KDR modulates VEGF$_{165}$ binding to KDR To determine whether expression of VEGF$_{165}$R/NP-1 had any effect on VEGF$_{165}$ interactions with KDR, PAE cells that were previously transfected with KDR cDNA to produce stable clones of PAE/KDR cells (Waltenberger et al., *J. Biol. Chem.* 269, 26988–26995 (1994)), were transfected with VEGF$_{165}$R/NP-1 cDNA and stable clones expressing both receptors (PAE/KDR/NP-1) were obtained. These cells bound $^{125}$I-VEGF$_{165}$ to KDR (FIG. 8, lane 6, upper complex) and to VEGF$_{165}$R/NP-1 (FIG. 8, lane 6, lower complex) to yield a cross-linking profile similar to HUVEC (FIG. 8, lane 1). On the other hand, the PAE/KDR/NP-1 cells bound $^{125}$I-VEGF$_{12}$ to form a complex only with KDR (FIG. 8, lanes 9 and 10), consistent with the inability of VEGF$_{121}$ to bind VEGF$_{165}$R/NP-1.

It appeared that in cells co-expressing KDR and VEGF$_{165}$R/NP-1 (FIG. 8, lane 6), the degree of I$^{25}$1-VEGF$_{165}$-KDR 240 kDa complex formation was enhanced compared to the parental PAE/KDR cells (FIG. 8, lane 5). These results were reproducible and the degree of $^{125}$I-VEGF$_{165}$-KDR 240 kDa complex formation in different clones was correlated positively with the levels of VEGF$_{165}$R/NP-1 expressed (not shown). However, it could not be ruled out definitively that these differential KDR binding results were possibly due to clonal selection post-transfection. Therefore, parental PAE/KDR cells were transfected with VEGF$_{165}$R/NP-1 cDNA and $^{125}$-VEGF$_{165}$ was bound and cross-linked to the cells three days later in order to avoid any diversity of KDR expression among individual clones (FIG. 9). A labeled 240 kDa complex containing KDR was formed in parental PAE/KDR cells (FIG. 9, lane 1) and PAE/KDR cells transfected with the expression vector (FIG. 9, lane 2). However, when $^{125}$I-VEGF165 was cross-linked to PAE/KDR cells transiently expressing VEGF$_{165}$R/NP-1, a more intensely labeled 240 kDa complex, about 4 times greater, was observed (FIG. 9, lane 3), compared to parental PAE/KDR cells (FIG. 9, lane 1) and PAE/KDR cells transfected with expression vector (FIG. 9, lane 2). These results suggest that co-expression of KDR and VEGF$_{165}$R/NP-1 genes in the same cell enhances the ability of VEGF$_{165}$ to bind to KDR.

Figure 10:
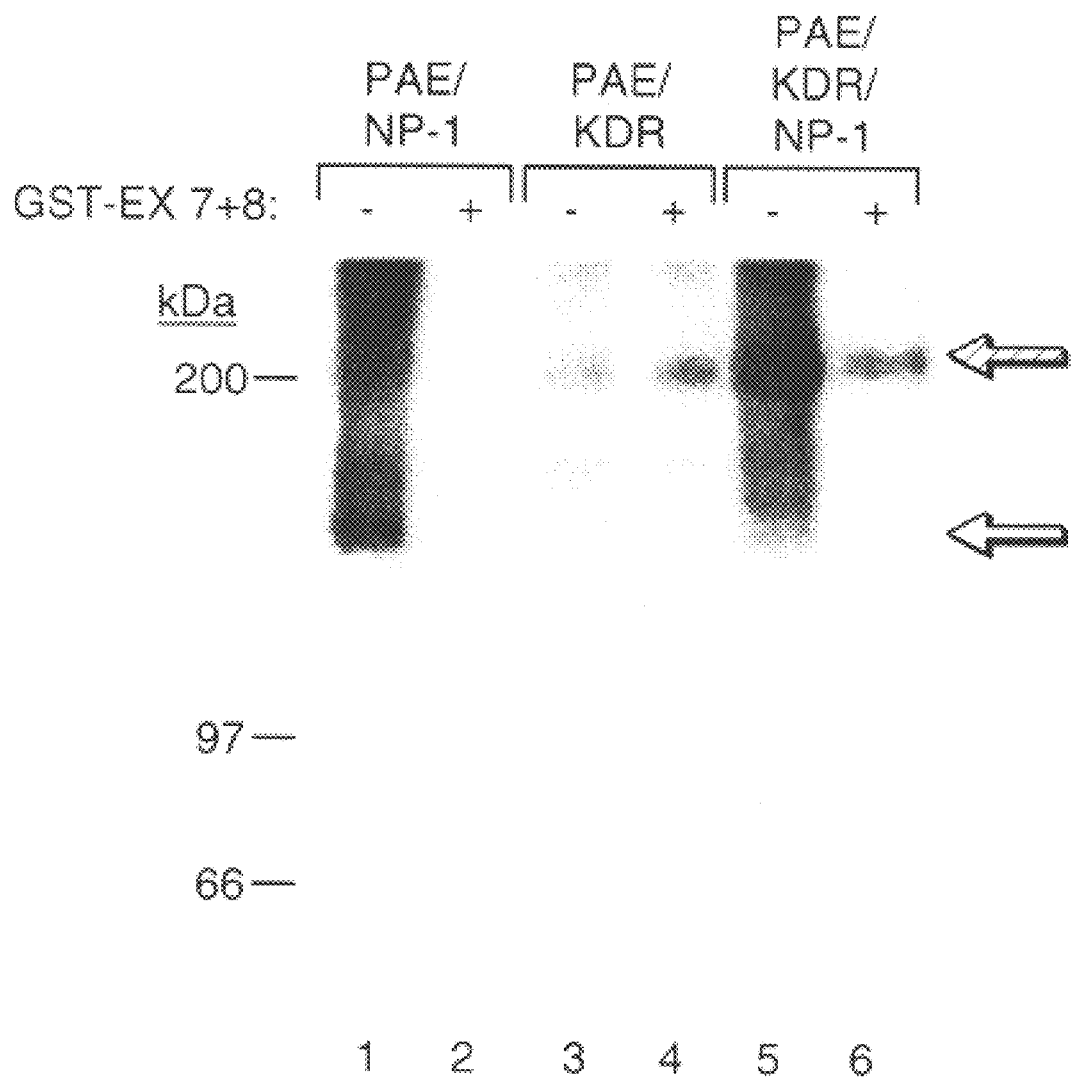
FIG. 10 shows inhibition of $^{125}$I-VEGF$_{165}$ binding to VEGF$_{165}$R/NP-1 interferes with its binding to KDR. $^{125}$I-VEGF$_{165}$ (5 ng/ml) was bound to subconfluent cultures of PAE transfected with human VEGF$_{165}$R/NP-1 cDNA (PAE/NP-1) (lanes 1 and 2), PAE/KDR cells (lanes 3 and 4), and PAE/KDR cells transfected with human VEGF$_{165}$R/NP-1 cDNA (PAE/KDR/NP-1) (lanes 5 and 16) in 35 mm dishes. The binding was carried out in the presence (lanes 2, 4, and 6) or the absence (lanes 1, 3, and 5) of 25 μg/ml GST-Ex 7+8. Heparin (1 μg/ml) was added to each dish. At the end of a 2 hour incubation, $^{125}$I-VEGF$_{165}$ was chemically cross-linked to the cell surface. The cells were lysed and proteins were resolved by 6% SDS-PAGE as in FIG. 9. Solid arrows denote radiolabeled complexes containing $^{125}$I-VEGF$_{165}$ and KDR, open arrows denote radiolabeled complexes containing $^{125}$I-VEGF$_{165}$ and VEGF$_{165}$R/NP-1.

A GST-VEGF Exon 7+8 fusion protein inhibits VEGF$_{165}$ binding to VEGF$_{165}$R/NP-1 and KDR We have shown that $^{125}$-VEGF$_{165}$ binds to VEGF$_{165}$R/NP-1 through its exon 7-encoded domain (Soker et al., *J. Biol. Chem.* 271, 5761–5767 (1996)). In addition, a GST fusion protein containing the peptide encoded by VEGF exon 7+8 (GST-Ex 7+8), inhibits completely the binding of $^{125}$I-VEGF$_{165}$ to VEGF$_{165}$R/NP-1 associated with 231 cells and HUVEC (Soker et al.. *J. Biol. Chem.* 271, 5761–5767 (1996); Soker et al., *J. Biol. Chem.* 272, 31582–31588 (1997)). When, added to PAE/NP-1 cells, the fusion protein completely inhibited binding to VEGF$_{165}$R/NP-1 (FIG. 10, lane 2 compared to lane 1). On the other hand, it did not inhibit $^{125}$I-VEGF$_{165}$ binding at all to KDR (FIG. 10, lane 4 compared to lane 3). Thus, these results demonstrate that GST-Ex 7+8 binds directly to VEGF$_{165}$R/NP-1 but does not bind to KDR. The effects of GST-Ex 7+8 are different, however, in cells co-expressing both VEGF$_{165}$R/NP-1 and KDR (PAE/KDR/NP-1). Consistent with the results in FIGS. 8 and 9, the degree of $^{125}$I-VEGF$_{165}$ binding to KDR in PAE/KDR/NP-1 cells (FIG. 10, lane 5) was greater than to the parental PAE/KDR cells (FIG. 10, lane 3). Interestingly, in PAE/KDR/NP-1 cells, GST-Ex 7+8 inhibited not only $^{125}$I-VEGF$_{165}$ binding to VEGF$_{165}$R/NP-1 completely as expected, but it also inhibited binding to KDR substantially which was unexpected (FIG. 10, lane 6 compared to lane 5). In the presence of GST-Ex 7+8, binding of $^{125}$I-VEGF$_{165}$ to KDR in these cells was reduced to the levels seen in parental PAE/KDR cells not expressing VEGF$_{165}$R/NP-1 (FIG. 10, lane 6 compared to lanes 3 and 4). Since the fusion protein does not bind directly to KDR, these results suggest that inhibiting the binding of $^{125}$I-VEGF$_{165}$ to VEGF$_{165}$R/NP-1 directly, inhibits its binding to KDR indirectly. Taken together, the results in FIGS. 8, 9 and 10 suggest that interactions of VEGF$_{165}$ with VEGF$_{165}$R/NP-1 enhance VEGF interactions with KDR.

Neuropilin-1 is an isoform-specific VEGF$_{165}$ receptor

Recently, we described a novel 130–135 kDa VEGF cell surface receptor that binds VEGF$_{165}$ but not VEGF$_{121}$ and that we named, accordingly, VEGF$_{165}$R (Soker et al., *J. Biol Chem.* 271, 5761–5767 (1996)). We have now purified VEGF$_{165}$R, expression cloned its cDNA, and shown it to be identical to human neuropilin-1 (NP-1) (He and Tessier-Lavigne, *Cell* 90 739–751 (1997)). The evidence that VEGF$_{165}$R is identical to NP-1 and that NP-1 serves as a receptor for VEGF$_{165}$ is as follows: i) purification of VEGF$_{165}$R protein from human MDA-MB-231 (231) cells using VEGF affinity, yielded a 130–140 kDa doublet upon SDS-PAGE and silver stain. N-terminal sequencing of both proteins yielded the same N-terminal sequence of 18 amino acids that demonstrated a high degree of homology to mouse NP-1 (Kawakami et al., *J. Neurobiol.* 29, 1–17 (1995)); ii) After we purified VEGF$_{165}$R from human 231 cells, the cloning of human NP-1 was reported (He and Tessier-Lavigne, *Cell* 90, 739–751 (1997)) and the N-terminal sequence of human VEGF$_{165}$R was found to be identical to a sequence in the N-terminal region of human NP-1; iii) Expression cloning using a 231 cell cDNA library resulted in isolation of several cDNA clones and their sequences were identical to the human NP-1 cDNA sequence (He and Tessier-Lavigne, *Cell* 90, 739–751 (1997)). The combination of purification and expression cloning has the advantage over previous studies where only expression cloning was used (He and Tessier-Lavigne, *Cell* 90, 739–751 (1997); Kolodkin et al., *Cell* 90, 753–762 (1997)), in allowing unambiguous identification of the NP-1 protein N-terminus; iv) Northern blot analysis of NP-1 gene expression was consistent with previous $^{125}$I-VEGF$_{165}$ cross-linking experiments (Soker et al., *J. Biol. Chem.* 271, 5761–5767 (1996)). Cells that bound VEGF$_{165}$ to VEGF$_{165}$R synthesized relatively abundant NP-1 mRNA while cells that showed very little if any VEGF$_{165}$ binding, did not synthesize much if any NP-1 mRNA; v) when NP-1 was expressed in PAE cells, the transfected, but not the parental cells, were able to bind VEGF$_{165}$ but not VEGF$_{121}$, consistent with the isoform specificity of binding previously shown for HUVEC and 231 cells (Soker et al., *J. Biol. Chem.* 271, 5761–5767 (1996)). Furthermore, the K$_d$ of $^{125}$I-VEGF$_{165}$ binding of to PAE expressing NP-1 was about 3×10$^{-10}$M, consistent with previous K$_d$ binding values of 2–2.8×10$^{-10}$M for 231 cells and HUVEC (Soker et al., *J. Biol. Chem.* 271, 5761–5767 (1996)); and vi) The binding of VEGF$_{165}$ to cells expressing NP-1 post-transfection was more efficient in the presence of heparin as was the binding of this ligand to HUVEC and 231 cells (Gitay-Goren et al., *J. Biol. Chem.* 267, 6093–6098 (1992); Soker et al., *J. Biol. Chem.* 271, 5761–5767 (1996)). Taken together, these results show not only that VEGF$_{165}$R is identical to NP-1 but that it is a functional receptor that binds VEGF$_{165}$ in an isoform-specific manner. Accordingly, we have named this VEGF receptor VEGF$_{165}$R/NP-1.

In addition to the expression cloning of VEGF$_{165}$R/NP-1 cDNA, another human cDNA clone was isolated whose predicted amino acid sequence was 47% homologous to that of VEGF$_{165}$R/NP-1 and over 90% homologous to rat neuropilin-2 (NP-2) which was recently cloned (Kolodkin et al., *Cell* 90, 753–762 (1997)). NP-2 binds members of the collapsin/semaphorin family selectively (Chen et al., *Neuron* 19, 547–559 (1997)).

The discovery that NP-1 serves as a receptor for VEGF$_{165}$ was a surprise since NP-1 had previously been shown to be associated solely with the nervous system during embryonic development (Kawakami et al., *J. Neurobiol.* 29, 1–17 (1995); Takagi et al., *Dev. Biol.* 170, 207–222 (1995)) and more recently as a receptor for members of the collapsin/semaphorin family (He and Tessier-Lavigne, *Cell* 90 739–751 (1997); Kolodkin et al., *Cell* 90, 753–762 (1997)). NP-1 is a 130–140 kDa transmembrane glycoprotein first identified in the developing Xenopus optic system (Takagi et al., *Dev. Biol.* 122, 90–100 (1987); Takagi et al., *Neuron* 7, 295–307 (1991)). NP-1 expression in the nervous system is highly regulated spatially and temporally during development and in particular is associated with those developmental stages when axons are actively growing to form neuronal connections. (Fujisawa et al., *Dev. Neurosci* 17, 343–349 (1995); Kawakami et. al., *J. Neurobiol* 29, 1–17 (1995); Takagi et al., *Dev. Biol.* 170, 207–222 (1995)). The NP-1 protein is associated with neuronal axons but not the stomata (Kawakami et al., *J. Neurobiol* 29, 1–17 (1995)). Functionally, neuropilin has been shown to promote neurite outgrowth of optic nerve fibers in vitro (Hirata et al., *Neurosci. Res.* 17, 159–169 (1993)) and to promote cell adhesiveness (Tagaki et al., *Dev. Biol.* 170, 207–222 (1995)). Targeted disruption of NP-1 results in severe abnormalities in the trajectory of efferent fibers of the peripheral nervous system (Kitsukawa et al., *Neuron* 19, 995–1005 (1997)). Based on the these studies, it has been suggested that NP-1 is a neuronal cell recognition molecule that plays a role in axon growth and guidance (Kawakami et al., *J. Neurobiol.* 29, 1–17 (1995); He and Tessier-Lavigne, *Cell* 90, 739–751 (1997); Kitsukawa et al., *Neuron* 19, 995–1005 1997; Kolodkin et al., *Cell* 90, 753–762 (1997)).

Our results are the first to show that VEGF$_{165}$N/RP-1 is also expressed in adult tissues, in contrast to the earlier studies that have shown that NP-1 expression in Xenopus, chicken and mouse is limited to the developmental and early post-natal stages (Fujisawa et al., *Dev. Neurosci.* 17, 343–349 (1995); Kawakami et al., *J. Neurobiol.* 29, 1–17 (1995); Takagi et al., *Dev. Biol.* 170, 207–222 (1995)). For example, in mice, NP-1 is expressed in the developing nervous system starting in the dorsal root ganglia at day 9 and ceases at day 15 (Kawakami et al., *J. Neurobiol.* 29, 1–17 (1995). Our Northern blot analysis of human adult tissue demonstrates relatively high levels of VEGF$_{165}$R/NP-1 mRNA transcripts in heart, placenta, lung, liver, skeletal muscle, kidney and pancreas. Interestingly, there is very little relative expression in adult brain, consistent with the mouse nervous system expression studies (Kawakami et al., *J. Neurobiol.* 29, 1–17 (1995)). VEGF$_{165}$R/NP-1 is also expressed in a number of cultured non-neuronal cell lines including EC and a variety of tumor-derived cells. A possible function of VEGF$_{165}$R/NP-1 in these cells is to mediate angiogenesis as will be discussed below.

In addition, NP-1 has been identified as a receptor for the collapsin/semaphorin family by expression cloning of a cDNA library obtained from rat E14 spinal cord and dorsal root ganglion (DRG) tissue (He and Tessier-Lavigne, *Cell* 90, 739–751 (1997); Kolodkin et al., *Cell* 90, 753–762 (1997)). The collapsin/semaphorins (collapsin-D-1/Sema III/Sem D) comprise a large family of transmembrane and secreted glycoproteins that function in repulsive growth cone and axon guidance (Kolodkin et al., *Cell* 75, 1389–1399 (1993)). The repulsive effect of sema III for DRG cells was blocked by anti-NP-1 antibodies (He and Tessier-Lavigne, *Cell* 90, 739–751 (1997); Kolodkin et al., *Cell* 90, 753–762 (1997)). The K$_d$ of sema III binding to NP-1, 0.15–3.25×10$^{-10}$M (He and Tessier-Lavigne, *Cell* 90, 739–751 (1997); Kolodkin et al., *Cell* 90, 753–762 (1997)) is similar to that of VEGF$_{165}$ binding VEGF$_{165}$/NP-1, which is about 3×10$^{-10}$M. These results indicate that two structurally different ligands with markedly different biological activities, VEGF-induced stimulation of EC migration and proliferation on one hand, and sema III-induced chemorepulsion of neuronal cells, on the other hand, bind to the same receptor and with similar affinity. An interesting question is whether the two ligands bind to the same site on VEGF$_{165}$R/NP-1 or to different sites. VEGF165R/NP-1 has five discrete domains in its ectodomain, and it has been suggested that this diversity of protein modules in NP-1 is consistent with the possibility of multiple binding ligands for NP-1 (Takagi et al., *Neuron* 7, 295–307 (1991); Feiner et al., *Neuron* 19 539–545 (1997); He and Tessier-Lavigne, *Cell* 90 739–751 (1997). Preliminary analysis does not indicate any large degree of sequence homology between sema III and VEGF exon 7 which is responsible for VEGF binding to VEGF$_{165}$R/NP-1 (Soker et al., *J. Biol. Chem.* 271, 5761–5767 (1996)). However there may be some 3-dimensional structural similarities between the two ligands. Since both neurons and blood vessels display branching and directional migration, the question also arises as to whether VEGF$_{165}$ displays any neuronal guidance activity and whether sema III has any EC growth factor activity. These possibilities have not been examined yet. However, it may be that VEGF requires two receptors, KDR and NP-1 for optimal EC growth factor activity (Soker et al., *J. Biol. Chem.* 272, 31582–31588 (1997)) and that sema III requires NP-1 and an as yet undetermined high affinity receptor for optimal chemorepulsive activity (Feiner et al., *Neuron* 19, 539–545 (1997;) He and Tessier-Lavigne, *Cell* 90, 739–751 (1997); Kitsukawa et al., *Neuron* 19, 995–1005 (1997)), so that the presence of NP-1 alone might not be sufficient for these ligands to display novel biological activities. Future studies will determine whether there are any connections between the mechanisms that regulate neurogenesis and angiogenesis.

VEGF$_{165}$R/NP-1 role in angiogenesis

Figure 11C:
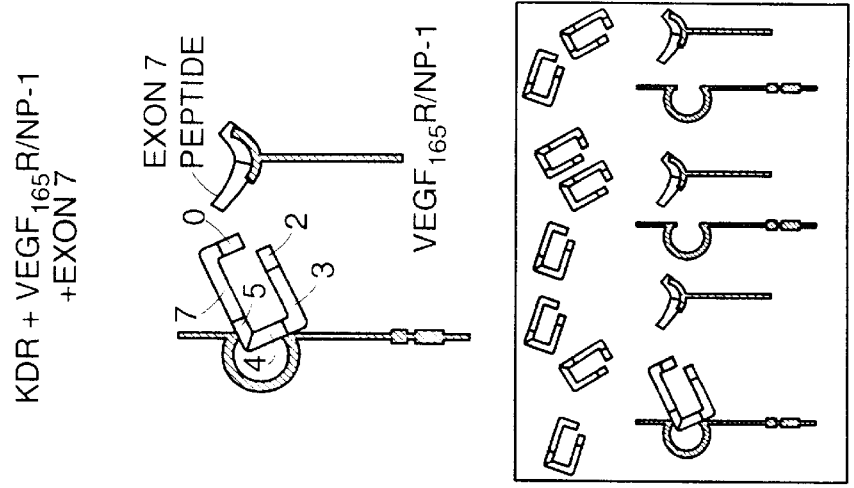
FIGS. 11A–C show a model for VEGF$_{165}$R/NP-1 modulation of VEGF$_{165}$ Binding to KDR. 11A. Cells expressing KDR alone. 11B. Cells co-expressing KDR and VEGF$_{165}$R/NP-1. 11C. Cells co-expressing KDR and VEGF$_{165}$R/NP-1 in the presence of GST-Ex 7+8 fusion protein.
Figure 11B:
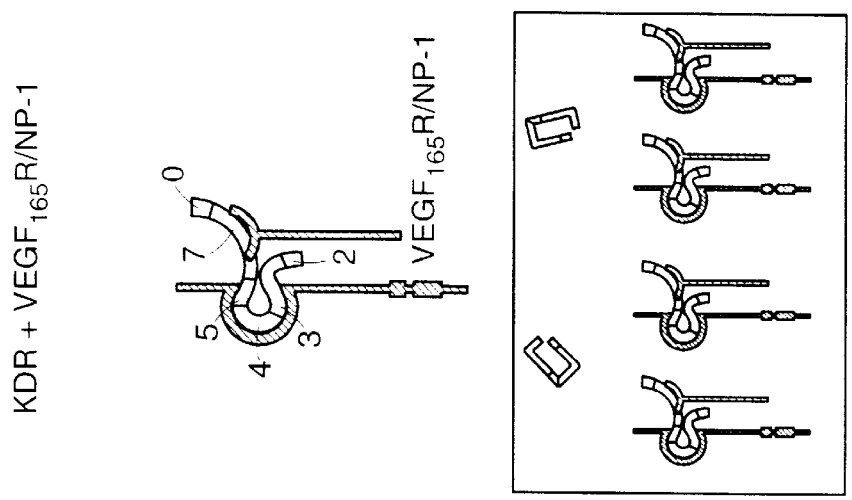
Figure 11A:
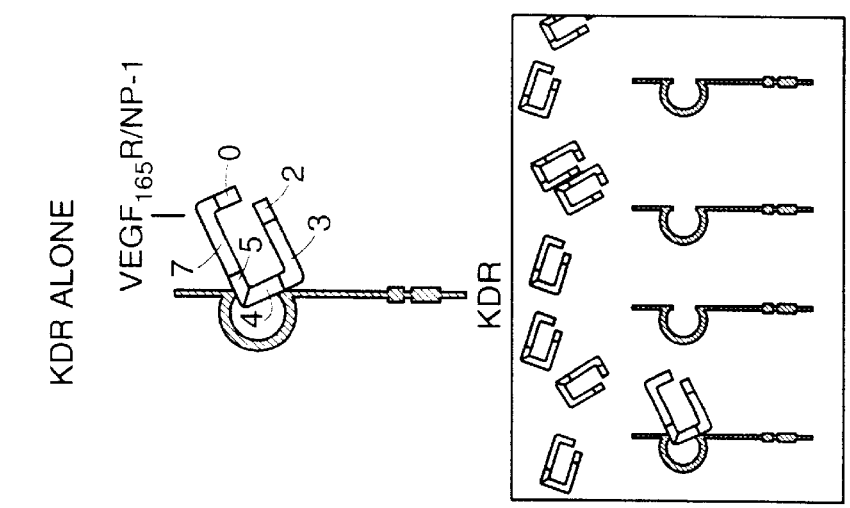

VEGF$_{165}$R/NP-1 modulates the binding of VEGF$_{165}$ to KDR, a high affinity RTK that is an important regulator of angiogenesis as evidenced by KDR knock out experiments in mice (Shalaby et al., *Nature* 376, 62–66 (1995). The affinity of KDR for VEGF$_{165}$ is about 50 times greater than for VEGF$_{165}$R/NP-1 (Gitay-Goren et al., *J. Biol. Chem.* 287, 6003–6096 (1992); Waltenberger et al., *J. Biol. Chem.* 269, 26988–26995 (1994)). When VEGF$_{165}$R/NP-1 and KDR are co-expressed, the binding of $^{125}$I-VEGF$_{165}$ to KDR is enhanced by about 4-fold compared to cells expressing KDR alone. The enhanced binding can be demonstrated in stable clones co-expressing VEGF$_{165}$R/NP-1 and KDR (PAE/KDR/NP-1 cells), and also in PAE/KDR cells transfected transiently with VEGF$_{165}$R/NP-1 cDNA where clonal selection does not take place. Conversely, when the binding of $^{125}$I-VEGF$_{165}$ to VEGF$_{165}$R/NP-1 in PAE/KDRP/NP-1 cells is inhibited completely by a GST fusion protein containing VEGF exons 7+8 (GST-Ex 7+8), the binding to KDR is inhibited substantially, down to the levels observed in cells expressing KDR alone. The fusion protein binds to VEGF$_{165}$R/NP-1 directly but is incapable of binding to KDR directly (Soker et al., *J. Biol. Chem.* 272, 31582–31588 (1997)). Although, not wishing to be bound by theory, we believe that VEGF$_{165}$ binds to VEGF$_{165}$R/NP-1 via the exon 7-encoded domain and facilitates VEGF$_{165}$ binding to KDR via the exon 4-encoded domain (FIG. 11). VEGF$_{165}$R/NP-1, with its relatively high receptor/cell number, about $0.2$–$2 \times 10^5$ (Gitay-Goren et al., *J. Biol. Chem.* 287, 6003–6096 (1992); Soker et al., *J. Biol. Chem.* 271, 5761–5767 (1996)), appears to serve to concentrate VEGF$_{165}$ on the cell surface, thereby providing greater access of VEGF$_{165}$ to KDR. Alternatively, binding to VEGF$_{165}$R/NP-1, VEGF$_{165}$ undergoes a conformational change that enhances its binding to KDR. The end result would be elevated KDR signaling and increased VEGF activity. Although we can demonstrate enhanced binding to KDR, to date we have not been able to demonstrate enhanced VEGF mitogenicity for PAE/KDR/NP-1 cells compared to PAE/KDR cells. One reason is that these cell lines do not proliferate readily in response to VEGF as do HUVEC (Waltenberger et al., *J. Biol. Chem.* 269, 26988–26995 (1994). Nevertheless, we have shown that VEGF$_{165}$, which binds to both KDR and VEGF$_{165}$R/NP-1, is a better mitogen for HUVEC than is VEGF$_{121}$, which binds only to KDR (Keyt et al., *J. Biol. Chem.* 271, 5638–5646 (1996b); Soker et al., *J. Biol. Chem.* 272, 31582–31588 (1997). Furthermore, inhibiting VEGF$_{165}$ binding to VEGF$_{165}$R/NP-1 on HUVEC by GST-EX 7+8, inhibits binding to KDR and also inhibits VEGF$_{165}$-induced HUVEC proliferation, down to the level induced by VEGF$_{121}$ (Soker et al., *J. Biol. Chem* 272, 31582–31588 (1997)). Taken together, these results suggest a role for VEGF$_{165}$R/NP-1 in mediating VEGF$_{165}$, but not VEGF$_{121}$ mitogenic activity. The concept that dual receptors regulate growth factor binding and activity has been previously demonstrated for TGF-β, bFGF and NGF (Lopez-Casillas et al., *Cell* 67, 785–795 (1991); Yayon et al., *Cell* 64,841–848 (1991; Barbacid, *Curr. Opin. Cell Biol.* 7, 148–155 (1995)).

Another connection between VEGF$_{165}$R/NP-1 and angiogenesis comes from studies in which NP-1 was overexpressed ectopically in transgenic mice (Kitsuskawa et al., *Develop.* 121, 4309–4318 (1995)). NP-1 overexpression resulted in embryonic lethality and the mice died in utero no later than on embryonic day 15.5 and those that survived the best had lower levels of NP-1 expression. Mice overexpressing NP-1 displayed morphologic abnormalities in a limited number of non-neural tissues such as blood vessels, the heart and the limbs. NP-1 was expressed in both the EC and in the mesenchymal cells surrounding the EC. The embryos possessed excess and abnormal capillaries and blood vessels compared to normal counterparts and in some cases dilated blood vessels as well. Some of the chimeric mice showed hemorrhaging, mainly in the head and neck. These results are consistent with the possibility that ectopic overexpression of VEGF$_{165}$R/NP-1 results in inappropriate VEGF$_{165}$ activity, thereby mediating enhanced and/or aberrant angiogenesis. Another piece of evidence for a link between NP-1 and angiogenesis comes from a recent report showing that in mice targeted for disruption of the NP-1 gene, the embryos have severe abnormalities in the peripheral nervous system but that their death in utero at days 10.5–12.5 is most probably due to anomalies in the cardiovascular system (Kitsukawa et al., *Neutron* 19, 995–1005 (1997))

VEGF$_{165}$R/NP -1 is associated with tumor-derived cells

The greatest degree of VEGF$_{165}$R/NP-1 expression that we have detected so far occurs in tumor-derived cells such as 231 breast carcinoma cells and PC3 prostate carcinoma cells, far more than occurs in HUVEC. The tumor cells express abundant levels of VEGF$_{165}$R/NP-1 mRNA and about 200,000 VEGF$_{165}$ receptors/cell (Soker et al., *J. Biol. Chem.* 271, 5761–5767 (1996)). On the other hand, these tumor cells do not express KDR or Flt-1 so that VEGF$_{165}$R/NP-1 is the only VEGF receptor associated with these cells. The tumor cells are therefore useful for testing whether VEGF$_{165}$R/NP-1 is a functional receptor for VEGF$_{165}$ in the absence of a KDR background. To date, we have not been able to show that VEGF$_{165}$R/NP-1 mediates a VEGF$_{165}$ signal in tumor-derived cells as measured by receptor tyrosine phopshorylation. Nevertheless, VEGF$_{165}$ might have an effect on tumor cells by inducing some as yet undetermined activity such as enhanced survival, differentiation, or motility. A recent report has demonstrated that glioma cells express a 190 kDa protein that binds VEGF$_{165}$ but not VEGF$_{121}$ efficiently (Omura et al., *J. Biol. Chem.* 272, 23317–23322 (1997)). No stimulation of tyrosine phosphorylation could be demonstrated upon binding of VEGF$_{165}$ to this receptor. Whether the 190 kDa isoform-specific receptor is related to VEGF$_{165}$R/NP-1 is not known presently.

VEGF$_{165}$R/NP-1 may have a storage and sequestration function for VEGF$_{165}$. One might envision that VEGF$_{165}$ is produced by a tumor cell and binds to VEGF$_{165}$R/NP-1 on that cell via the exon 7-encoded domain (Soker et al., *J. Biol. Chem.* 271, 5761–5767 (1996)). The stored VEGF$_{165}$ could be then released to stimulate tumor angiogenesis in a paracrine manner. Alternatively, VEGF$_{165}$R/NP-1 may mediate a juxtacrine effect in which VEGF$_{165}$ is bound to VEGF$_{165}$R/NP-1 on a tumor cell via the exon 7-encoded domain and is also bound to KDR on a neighboring EC via the exon 4-encoded domain (Keyt et al., *J. Biol. Chem.* 271, 5638–5646 (1996b)). Such a mechanism could result in a more efficient way for tumor cells to attract EC, thereby enhancing tumor angiogenesis.

In summary, we have demonstrated by independent purification and expression cloning methods that the VEGF isoform specific receptor, VEGF$_{165}$R, is identical to NP-1, a cell surface protein previously identified as playing a role in embryonic development of the nervous system and as being a receptor for the collapsins/semaphorins. Furthermore, binding to VEGF$_{165}$R/NP-1 enhances the binding of VEGF$_{165}$ to KDR on EC and tumor cells.

Experimental Rationale

We have discovered that tumor cell neuropilin-1 mediates tumor cell motility and thereby metastasis. In a Boyden chamber motility assay, $VEGF_{165}$ (50 ng/ml) stimulates 231 breast carcinoma cell motility in a dose-response manner, with a maximal 2-fold stimulation (FIG. 15A). On the other hand, $VEGF_{121}$ has no effect on motility of these cells (FIG. 15B). Since 231 cells do not express KDR or Flt-1, these results suggest that tumor cells are directly responsive to $VEGF_{165}$ and that $VEGF_{165}$ might signal tumor cells via neuropilin-1. Possible candidates for mediating $VEGF_{165}$-induced motility of carcinoma cells are P13-kinase (P13-K) (Carpenter, et al. (1996) Curr. Opin. Cell Biol. 8: 153–158.). Since 231 cells do not express KDR or Flt-1, these results suggest that tumor cells are directly responsive to $VEGF_{165}$ and that $VEGF_{165}$ might signal tumor cells via neuropilin-1.

The other type of evidence is that neuropilin-1 expression might be associated with tumor cell motility. We have analyzed two variants of Dunning rat prostate carcinoma cells, AT2.1 cells, which are of low motility and low metastatic potential, and AT3.1 cells, which are highly motile, and metastatic. Cross-linking and Northern blot analysis show that AT3.1 cells express abundant neuropilin-I, capable of binding $VEGF_{165}$, while AT2.1 cells don't express neuropilin-1 (FIG. 16). Immunostaining of tumor sections confirms the expression of neuropilin-1 in AT3.1, but not AT2.1 tumors (FIG. 17). Furthermore, the immunostaining shows that in subcutaneous AT3.1 and PC3 tumors, the tumor cells expressing neuropilin-1 are found preferentially at the invading front of the tumor/dermis boundary (FIG. 17). To determine more directly whether neuropilin-1 expression is correlated with enhanced motility, neuropilin-1 was overexpressed in AT2.1 cells (FIG. 18). Three stable clones of AT2.1 cells overexpressing neuropilin-1 had enhanced motility in the Boyden chamber assay. These results indicate that expression of neuropilin-1 in AT2.1 cells enhances their motility. Taken together, it appears that neuropilin-1 expression on tumor cells is associated with the motile, metastatic phenotype.

The references cited throughout the specification are incorporated herein by reference.

The present invention has been described with reference to specific embodiments. However, this application is intended to cover those changes and substitutions which may be made by those skilled in the art without departing from the spirit and the scope of the appended claims.

What is claimed:

1. A method for determining prognosis for prostate cancer in an individual comprising:

a. obtaining a tumor sample from said individual;

b. measuring VEGF$_{165}$R/NP-1 (SEQ ID NO: 1) receptor amounts to obtain a receptor level in said sample;

c. correlating said receptor level with a baseline level, wherein the baseline level is determined by measuring levels of VEGF165R/NP-1 in a sample of disease free individuals; and d. correlating levels of receptor greater than the baseline with an indication of unfavorable prognosis and levels of receptor at the baseline or less with a favorable prognosis, whereby the prognosis of said patient is determined.

2. The method of claim 1, wherein the level of mRNA from the tumor sample expressing VEGF$_{165}$R/NP-1 (SEQ ID NO: 1) is measured.

3. The method of claim 2, wherein the mRNA is detected by use of an RNA dependent polymerase chain reaction.

4. The method of claim 2, wherein the mRNA is detected by Northern blot analysis by hybridizing mRNA from said tumor sample to a VEGF$_{165}$R/NP-1 (SEQ ID NO: 1) nucleotide probe.

* * * * *

SEQUENCE LISTING

<160> NUMBER OF SEQ ID NOS: 11

<210> SEQ ID NO 1
<211> LENGTH: 5653
<212> TYPE: DNA
<213> ORGANISM: Homo sapiens

<400> SEQUENCE: 1

```
aagggagagg aagccggagc taaatgacag gatgcaggcg acttgagaca caaaaagaga      60
agcgttcctc tcggatccag gcattgcctc gctgctttct tttctccaag acgggctgag     120
gattgtacag ctctaggcgg agttggggct cttcggatcg cttagattct cctctttgct     180
gcatttcccc ccacgtcctc gttctcccgc gtctgcctgc ggacccggag aagggagaat     240 ggagagggg ctgccgctcc tctgcgccgt gctcgccctc gtcctcgccc cggccggcgc     300
ttttcgcaac gataaatgtg gcgatactat aaaaattgaa agcccgggt accttacatc       360 tcctggttat cctcattctt atcacccaag tgaaaaatgc gaatggctga ttcaggctcc      420
ggacccatac cagagaatta tgatcaactt caaccctcac ttcgatttgg aggacagaga     480
ctgcaagtat gactacgtgg aagtgttcga tggagaaaat gaaaatggac attttagggg     540
aaagttctgt ggaaagatag cccctcctcc tgttgtgtct tcagggccat ttcttttat       600 caaatttgtc tctgactacg aaacacatgg tgcaggattt tccatacgtt atgaaatttt      660
caagagaggt cctgaatgtt cccagaacta cacaacacct agtggagtga taaagtcccc      720
cggattccct gaaaaatatc ccaacagcct tgaatgcact tatattgtct ttgcgccaaa      780
gatgtcagag attatcctgg aatttgaaag ctttgacctg gagcctgact caaatcctcc      840
aggggggatg ttctgtcgct acgaccggct agaaatctgg gatggattcc ctgatgttgg      900
ccctcacatt gggcgttact gtggacagaa aacaccaggt cgaatccgat cctcatcggg      960
cattctctcc atggttttttt acaccgacag cgcgatagca aaagaaggtt tctcagcaaa    1020
ctacagtgtc ttgcagagca gtgtctcaga agatttcaaa tgtatggaag ctctgggcat     1080
ggaatcagga gaaattcatt ctgaccagat cacagcttct tcccagtata gcaccaactg     1140
```

-continued

```
gtctgcagag cgctcccgcc tgaactaccc tgagaatggg tggactcccg gagaggattc    1200
ctaccgagag tggatacagg tagacttggg ccttctgcgc tttgtcacgg ctgtcgggac    1260
acagggcgcc atttcaaaag aaaccaagaa gaaatattat gtcaagactt acaagatcga    1320
cgttagctcc aacggggaag actggatcac cataaaagaa ggaaacaaac ctgttctctt    1380
tcagggaaac accaaccccca cagatgttgt ggttgcagta ttccccaaac cactgataac    1440
tcgatttgtc cgaatcaagc ctgcaacttg ggaaactggc atatctatga gatttgaagt    1500
atacggttgc aagataacag attatccttg ctctggaatg ttgggtatgg tgtctggact    1560
tatttctgac tcccagatca catcatccaa ccaaggggac agaaactgga tgcctgaaaa    1620
catccgcctg gtaaccagtc gctctggctg ggcacttcca cccgcacctc attcctacat    1680
caatgagtgg ctccaaatag acctggggga ggagaagatc gtgagggca tcatcattca    1740 gggtgggaag caccgagaga acaaggtgtt catgaggaag ttcaagatcg ggtacagcaa    1800
caacggctcg gactggaaga tgatcatgga tgacagcaaa cgcaaggcga agtcttttga    1860
gggcaacaac aactatgata cacctgagct gcggactttt ccagctctct ccacgcgatt    1920
catcaggatc taccccgaga gagccactca tggcggactg gggctcagaa tggagctgct    1980
gggctgtgaa gtggaagccc ctacagctgg accgaccact cccaacggga acttggtgga    2040
tgaatgtgat gacgaccagg ccaactgcca cagtggaaca ggtgatgact ccagctcac    2100 aggtggcacc actgtgctgg ccacagaaaa gcccacggtc atagacagca ccatacaatc    2160
agagtttcca acatatggtt ttaactgtga atttggctgg ggctctcaca agaccttctg    2220
ccactgggaa catgacaatc acgtgcagct caagtggagt gtgttgacca gcaagacggg    2280
acccattcag gatcacacag gagatggcaa cttcatctat tcccaagctg acgaaaatca    2340
gaagggcaaa gtggctcgcc tggtgagccc tgtggtttat tcccagaact ctgcccactg    2400
catgaccttc tggtatcaca tgtctgggtc ccacgtcggc acactcaggg tcaaactgcg    2460
ctaccgaaag ccagaggagt acgatcagct ggtctggatg gccattggac accaaggtga    2520
ccactggaag gaagggcgtg tcttgctcca caagtctctg aaactttatc aggtgatttt    2580
cgagggcgaa atcggaaaag gaaaccttgg tgggattgct gtggatgaca ttagtattaa    2640
caaccacatt tcacaagaag attgtgcaaa accagcagac ctggataaaa agaacccaga    2700
aattaaaatt gatgaaacag ggagcacgcc aggatacgaa ggtgaaggag aaggtgacaa    2760
gaacatctcc aggaagccag gcaatgtgtt gaagacctta gatcccatcc tcatcaccat    2820
catagccatg agtgccctgg gggtcctcct gggggctgtc tgtgggtcg tgctgtactg    2880 tgcctgttgg cataatggga tgtcagaaag aaacttgtct gccctggaga actataactt    2940
tgaacttgtg gatggtgtga agttgaaaaa agacaaactg aatacacaga gtacttattc    3000
ggaggcatga aggcagacag agatgaaaag acagtcaaag gacggaagtg gaaggacggg    3060
agtgagctgg ggagctgttg atctttcact atacaggctg ggaagtgtgt tgatgaccac    3120
tgagccaggc ttttctcagg agcttcaatg agtatggccg acagacatgg acaaggagct    3180
gtgttcacca tcggactcat gtgcagtcag cttttttcct gttggtttca tttgaataat    3240
cagatgctgt tgttgagacc aagtatgatt gacataatca ttcatttcga ccctcctgc    3300 ccctctctct ctctctcctc tccccttttgt ggattctttt tggaaactga gcgaaatcca    3360
agatgctggc accaagcgta ttccgtgtgg cccttttggat ggacatgcta cctgaaaccc    3420
agtgcccaga atatactaga atcaccgcat ttcagtggac tcctgaagtt gtacttgtgt    3480
```

-continued

```
ataattgccc gcgtcgtgca taggcaaaga aggattaggc tgttttcttt ttaaagtact   3540
gtagcctcag tactggtgta gtgtgtcagc tctgtttacg aagcaatact gtccagtttt   3600
cttgctgttt ttccggtgtt gtactaaacc tcgtgcttgt gaactccata cagaaaacgg   3660
tgccatccct gaacacggct ggccactggg tatactgctg acaaccgcaa caacaaaaac   3720
acaaatcctt ggcactggct agtctatgtc ctctcaagtg cctttttgtt tgtactggtt   3780
cattgtgtta cattaacgac ccactctgct tcttgctggt gaaagccctg ctctttaatc   3840
aaactctggt ggcccactga ctaagaagaa agtttatttt cgtgtgagat gccagcccct   3900
ccgggcaggc aagggctctg aagatttggc aacgtggctt aattgttctg cttttctgt    3960 agttcaattt catgtttctt gacccttttg tataaagcta caatattctc tcttattgtt   4020
ctttcatatg gaatgtattt tcaaatgtaa actctcttct ctttctctct cctatctctc   4080 tgtcttttt ctctcttaga attggaggat ttgccattgt ccaggaaaga aacttgcagc    4140
tttaacctgc tgggaatggc aaacgatttt actagacttt atgtttaaaa ataaataaat   4200
aagggaaatt cctaactttg ccctccaaag tctaactttg gttttcttgt taactggtta   4260
aagtgacagt atcttttttc cttatctatt ctattcaaaa tgacctttga tagaaatgtt   4320
ggcatttagt agaaatagtg ataagttgag gaaagaaata atacaaattg gctttcaagt   4380
gagacccaaa ggaagaactg gataaaatct tccaaatcca aaagcatgag atttttctat   4440
ccaaatatgc aaaaatgacc caagagaact ttcttatttt gctactgagt cacacaaggg   4500
aagtggaagg aagaacagtt aatttaagaa tgaaactata atcctgatg cctggggtc     4560 aagtatttta agataagagg gggaaaaaca cataaagtca acaaatgtt ttaaaaattc     4620 ataacagcaa ccttgaaaaa atagacttaa atgaatgctt ctagaaactt ccagcggctc   4680
acaaagaata agcctgcctt agggctggca acatctaagc ctctaacagc acagggaagc   4740
aaatatctta ccaggcagcc tatgaattaa cccaaagaag ctttggttgg ttttggtgga   4800
tttttatcat gccatgttgg acatgagatt ttttagatct tccttcccca cattgctaga   4860
cgtctcactc aaagacattt gttgggagtc acatttgcat catagacgag acagtccatt   4920
catcttagtt aaattggatt gagaatgcct tttgtttcca ggaaaatatt gatcaccatg   4980
aaagaagaat agtttttgt ccccagagac attcatttag ttgatataat cctaccagaa     5040
ggaaagcact aagaaacact cgtttgttgt ttttaaaggc aacagactta aagttgtcct   5100
cagccaagga aaaatgatac tgcaacttta aaatttaaag tatcttgcac tgataaatat   5160
atttaaaaat tatatgtttta taagttatt aatttgtaaa ggcagtgtta caaatgttc     5220 agtttatatt gttttagatt gttttgtaat ttttaaaggt gtaaaataac atataaatat   5280
atttaaaaat tatatgttta taagttatt aatttgtaaa ggcagtgtta caaatgttc     5340 agtttatatt gttttagatt gttttgtaat ttttaaaggt gtaaaataac atattttttc   5400
tttatggaaa tctataaaac tttctgtagt aaaatgtttt cattttactg gtatattatt   5460
gcttcatgtt ttgtaccatc ataagatttt gtgcagattt tttttacaga aattattatt   5520
ttctatgaca atatgacact tgtaaattgt tgtttcaaaa tgaacagcga agccttaact   5580
ttaaatgaca tttgtattct cagacactga gtagcataaa aaccacatga actgaactgt   5640
aacttaaatt ctt                                                       5653
```

<210> SEQ ID NO 2
<211> LENGTH: 923
<212> TYPE: PRT
<213> ORGANISM: Homo sapiens

<400> SEQUENCE: 2

```
Met Glu Arg Gly Leu Pro Leu Cys Ala Val Leu Ala Leu Val Leu
 1               5                  10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Glu Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
```

-continued

```
                405                 410                 415
Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
            755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830
```

```
Tyr Glu Gly Glu Gly Gly Asp Lys Asn Ile Ser Arg Lys Pro Gly
            835                 840                 845

Asn Val Leu Lys Thr Leu Asp Pro Ile Leu Ile Thr Ile Ile Ala Met
        850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
            885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
            915                 920

<210> SEQ ID NO 3
<211> LENGTH: 3404
<212> TYPE: DNA
<213> ORGANISM: Homo sapiens

<400> SEQUENCE: 3
gaattcggca cgaggggaaa ataaaagaga gaaaaacaca aagatttaaa caagaaacct      60
acgaacccag ctctggaaag agccaccttc tccaaaatgg atatgtttcc tctcacctgg     120
gttttcttag ccctctactt ttcaagacac caagtgagag ccaaccaga cccaccgtgc      180 ggaggtcgtt tgaattccaa agatgctggc tatatcacct ctcccggtta cccccaggac     240 taccctccc accagaactg cgagtggatt gtttacgccc ccgaacccaa ccagaagatt      300
gtcctcaact tcaaccctca ctttgaaatc gagaagcacg actgcaagta tgactttatc     360
gagattcggg atggggacag tgaatccgca gacctcctgg gcaaacactg tgggaacatc     420
gccccgccca ccatcatctc ctcgggctcc atgctctaca tcaagttcac ctccgactac     480
gcccggcagg gggcaggctt ctctctgcgc tacgagatct tcaagacagg ctctgaagat     540
tgctcaaaaa acttcacaag ccccaacggg accatcgaat ctcctgggtt tcctgagaag     600
tatccacaca acttggactg caccttacc atcctggcca aacccaagat ggagatcatc      660
ctgcagttcc tgatctttga cctggagcat gacccttttgc aggtgggaga ggggactgc    720 aagtacgatt ggctggacat ctgggatggc attccacatg ttggccccct gattggcaag     780
tactgtggga ccaaaacacc ctctgaactt cgttcatcga cggggatcct ctccctgacc     840
tttcacacgg acatggcggt ggccaaggat ggcttctctg cgcgttacta cctggtccac     900
caagagccac tagagaactt tcagtgcaat gttcctctgg gcatggagtc tggccggatt     960
gctaatgaac agatcagtgc ctcatctacc tactctgatg gaggtggac ccctcaacaa    1020 agccggctcc atggtgatga caatggctgg accccaact tggattccaa caaggagtat    1080
ctccaggtgg acctgcgctt tttaaccatg ctcacggcca tcgcaacaca gggagcgatt    1140
tccagggaaa cacagaatgg ctactacgtc aaatcctaca agctggaagt cagcactaat    1200
ggagaggact ggatggtgta ccggcatggc aaaaaccaca aggtatttca agccaacaac    1260
gatgcaactg aggtggttct gaacaagctc cacgctccac tgctgacaag gtttgttaga    1320
atccgccctc agacctggca ctcaggtatc gccctccggc tggagctctt cggctgccgg    1380
gtcacagatg ctccctgctc caacatgctg gggatgctct caggcctcat gcagactcc    1440 cagatctccg cctcttccac ccaggaatac ctctggagcc cagtgcagc ccgcctggtc    1500 agcagccgct cgggctggtt ccctcgaatc cctcaggccc agcccggtga ggagtggctt    1560
```

-continued

```
caggtagatc tgggaacacc caagacagtg aaaggtgtca tcatccaggg agcccgcgga    1620
ggagacagta tcactgctgt ggaagccaga gcatttgtgc gcaagttcaa agtctcctac    1680
agcctaaacg gcaaggactg gaatacatt caggaccccca ggaccagca gccaaagctg     1740 ttcgaaggga acatgcacta tgacacccct gacatccgaa ggtttgaccc cattccggca    1800
cagtatgtgc gggtataccc ggagaggtgg tcgccggcgg ggattgggat gcggctggag    1860
gtgctgggct gtgactggac agactccaag cccacggtag agacgctggg acccactgtg    1920
aagagcgaag agacaaccac ccctacccc accgaagagg aggccacaga gtgtggggag     1980
aactgcagct ttgaggatga caaagatttg cagctcccct cgggattcaa ttgcaacttc    2040
gatttcctcg aggagccctg tggttggatg tatgaccatg ccaagtggct ccggaccacc    2100
tgggccagca gctccagccc aaacgaccgg acgtttccag atgacaggaa tttcttgcgg    2160
ctgcagagtg acagccagag agagggccag tatgcccggc tcatcagccc ccctgtccac    2220
ctgccccgaa gcccggtgtg catggagttc cagtaccagg ccacgggcgg ccgcggggtg    2280
gcgctgcagg tggtgcggga agccagccag gagagcaagt tgctgtgggt catccgtgag    2340
gaccagggcg gcgagtggaa gcacgggcgg atcatcctgc ccagctacga catggagtac    2400
cagattgtgt tcgagggagt gataggaaa ggacgttccg gagagattgc cattgatgac      2460
attcggataa gcactgatgt cccactggag aactgcatga acccatctc ggcttttgca     2520 ggtgagaatt taaagtgga catcccagaa atacatgaga gagaaggata tgaagatgaa      2580
attgatgatg aatacgaggt ggactggagc aattcttctt ctgcaacctc agggtctggc    2640 gcccctcga ccgacaaaga aaagagctgg ctgtacaccc tggatcccat cctcatcacc      2700
atcatcgcca tgagctcact gggcgtcctc ctggggggcca cctgtgcagg cctcctgctc    2760
tactgcacct gttcctactc gggcctgagc tcccgaagct gcaccacact ggagaactac    2820
aacttcgagc tctacgatgg ccttaagcac aaggtcaaga tgaaccacca aaagtgctgc    2880
tccgaggcat gacggattgc acctgaatcc tatctgacgt tcattccag caagaggggc      2940 tggggaagat tacattttttt tttccttttgg aaactgaatg ccataatctc gatcaaaccg   3000
atccagaata ccgaaggtat ggacaggaca gaaaagcgag tcgcaggagg aagggagatg    3060
cagccgcaca ggggatgatt accctcctag gaccgcggtg gctaagtcat tgcaggaacg    3120
gggctgtgtt ctctgctggg acaaaacagg agctcatctc tttggggtca cagttctatt    3180
ttgtttgtga gtttgtatta ttattattat tattattat atatttttatt tctttggtct    3240 gtgagcaact caaagaggca gaagaggaga atgacttttc cagaatagaa gtggagcagt    3300
gatcattatt ctccgctttc tctttctaat caacacttga aaagcaaagt gtctttttcag   3360 cctttccatc tttacaaata aaactcaaaa aagctgtcca gctt                    3404
```

<210> SEQ ID NO 4
<211> LENGTH: 931
<212> TYPE: PRT
<213> ORGANISM: Homo sapiens

<400> SEQUENCE: 4

```
Met Asp Met Phe Pro Leu Thr Trp Val Phe Leu Ala Leu Tyr Phe Ser
 1               5                  10                  15

Arg His Gln Val Arg Gly Gln Pro Asp Pro Pro Cys Gly Gly Arg Leu
            20                  25                  30

Asn Ser Lys Asp Ala Gly Tyr Ile Thr Ser Pro Gly Tyr Pro Gln Asp
        35                  40                  45
```

-continued

```
Tyr Pro Ser His Gln Asn Cys Glu Trp Ile Val Tyr Ala Pro Glu Pro
 50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
                100                 105                 110

Ile Ile Ser Ser Gly Ser Met Leu Tyr Ile Lys Phe Thr Ser Asp Tyr
             115                 120                 125

Ala Arg Gln Gly Ala Gly Phe Ser Leu Arg Tyr Glu Ile Phe Lys Thr
 130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                 165                 170                 175

Phe Thr Ile Leu Ala Lys Pro Lys Met Glu Ile Ile Leu Gln Phe Leu
             180                 185                 190

Ile Phe Asp Leu Glu His Asp Pro Leu Gln Val Gly Glu Gly Asp Cys
         195                 200                 205

Lys Tyr Asp Trp Leu Asp Ile Trp Asp Gly Ile Pro His Val Gly Pro
 210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                 245                 250                 255

Lys Asp Gly Phe Ser Ala Arg Tyr Tyr Leu Val His Gln Glu Pro Leu
             260                 265                 270

Glu Asn Phe Gln Cys Asn Val Pro Leu Gly Met Glu Ser Gly Arg Ile
         275                 280                 285

Ala Asn Glu Gln Ile Ser Ala Ser Ser Thr Tyr Ser Asp Gly Arg Trp
 290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                 325                 330                 335

Thr Met Leu Thr Ala Ile Ala Thr Gln Gly Ala Ile Ser Arg Glu Thr
             340                 345                 350

Gln Asn Gly Tyr Tyr Val Lys Ser Tyr Lys Leu Glu Val Ser Thr Asn
         355                 360                 365

Gly Glu Asp Trp Met Val Tyr Arg His Gly Lys Asn His Lys Val Phe
 370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                 405                 410                 415

Gly Ile Ala Leu Arg Leu Glu Leu Phe Gly Cys Arg Val Thr Asp Ala
             420                 425                 430

Pro Cys Ser Asn Met Leu Gly Met Leu Ser Gly Leu Ile Ala Asp Ser
         435                 440                 445

Gln Ile Ser Ala Ser Ser Thr Gln Glu Tyr Leu Trp Ser Pro Ser Ala
 450                 455                 460

Ala Arg Leu Val Ser Ser Arg Ser Gly Trp Phe Pro Arg Ile Pro Gln
```

-continued

```
465                 470                 475                 480
Ala Gln Pro Gly Glu Glu Trp Leu Gln Val Asp Leu Gly Thr Pro Lys
                485                 490                 495

Thr Val Lys Gly Val Ile Ile Gln Gly Arg Gly Gly Asp Ser Ile
                500                 505                 510

Thr Ala Val Glu Ala Arg Ala Phe Val Arg Lys Phe Lys Val Ser Tyr
                515                 520                 525

Ser Leu Asn Gly Lys Asp Trp Glu Tyr Ile Gln Asp Pro Arg Thr Gln
530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Glu Thr Leu Gly Pro Thr Val
                595                 600                 605

Lys Ser Glu Glu Thr Thr Thr Pro Tyr Pro Thr Glu Glu Ala Thr
                610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
                660                 665                 670

Ser Ser Pro Asn Asp Arg Thr Phe Pro Asp Asp Arg Asn Phe Leu Arg
                675                 680                 685

Leu Gln Ser Asp Ser Gln Arg Glu Gly Gln Tyr Ala Arg Leu Ile Ser
690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Gly Glu Asn Phe Lys Val Asp Ile
                805                 810                 815

Pro Glu Ile His Glu Arg Glu Gly Tyr Glu Asp Glu Ile Asp Asp Glu
                820                 825                 830

Tyr Glu Val Asp Trp Ser Asn Ser Ser Ala Thr Ser Gly Ser Gly
                835                 840                 845

Ala Pro Ser Thr Asp Lys Glu Lys Ser Trp Leu Tyr Thr Leu Asp Pro
850                 855                 860

Ile Leu Ile Thr Ile Ile Ala Met Ser Ser Leu Gly Val Leu Leu Gly
865                 870                 875                 880

Ala Thr Cys Ala Gly Leu Leu Leu Tyr Cys Thr Cys Ser Tyr Ser Gly
                885                 890                 895
```

```
Leu Ser Ser Arg Ser Cys Thr Thr Leu Glu Asn Tyr Asn Phe Glu Leu
            900                 905                 910
Tyr Asp Gly Leu Lys His Lys Val Lys Met Asn His Gln Lys Cys Cys
            915                 920                 925
Ser Glu Ala
    930
```

<210> SEQ ID NO 5
<211> LENGTH: 18
<212> TYPE: PRT
<213> ORGANISM: Homo sapiens

<400> SEQUENCE: 5

```
Phe Arg Asn Asp Glu Cys Gly Asp Thr Ile Lys Ile Glu Asn Pro Gly
 1               5                  10                  15
Tyr Leu
```

<210> SEQ ID NO 6
<211> LENGTH: 18
<212> TYPE: PRT
<213> ORGANISM: Homo sapiens

<400> SEQUENCE: 6

```
Phe Arg Ser Asp Lys Cys Gly Gly Thr Ile Lys Ile Glu Ser Pro Gly
 1               5                  10                  15
Tyr Leu
```

<210> SEQ ID NO 7
<211> LENGTH: 24
<212> TYPE: DNA
<213> ORGANISM: Homo sapiens

<400> SEQUENCE: 7
tttcgcaacg ataaatgtgg cgat                                    24

<210> SEQ ID NO 8
<211> LENGTH: 20
<212> TYPE: DNA
<213> ORGANISM: Homo sapiens

<400> SEQUENCE: 8
tatcactcca ctaggtgttg                                         20

<210> SEQ ID NO 9
<211> LENGTH: 20
<212> TYPE: DNA
<213> ORGANISM: Homo sapiens

<400> SEQUENCE: 9
ccaaccagaa gattgtcctc                                         20

<210> SEQ ID NO 10
<211> LENGTH: 20
<212> TYPE: DNA
<213> ORGANISM: Homo sapiens

<400> SEQUENCE: 10
gtaggtagat gaggcactga                                         20

<210> SEQ ID NO 11
<211> LENGTH: 44

```
<212> TYPE: PRT
<213> ORGANISM: Homo sapiens

<400> SEQUENCE: 11

Pro Cys Gly Pro Cys Ser Glu Arg Arg Lys His Leu Phe Val Gln Asp
 1               5                  10                  15

Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys Arg
            35                  40
```